(12) United States Patent
Kemp et al.

(10) Patent No.: US 11,091,488 B2
(45) Date of Patent: Aug. 17, 2021

(54) 1-CYANO-PYRROLIDINE DERIVATIVES AS INHIBITORS OF USP30

(71) Applicant: MISSION THERAPEUTICS LIMITED, Cambridge (GB)

(72) Inventors: Mark Ian Kemp, Cambridge (GB); Martin Lee Stockley, Cambridge (GB); Andrew Madin, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 422 days.

(21) Appl. No.: 15/776,149

(22) PCT Filed: Nov. 29, 2016

(86) PCT No.: PCT/GB2016/053742
§ 371 (c)(1),
(2) Date: May 15, 2018

(87) PCT Pub. No.: WO2017/093718
PCT Pub. Date: Jun. 8, 2017

(65) Prior Publication Data
US 2020/0262838 A1 Aug. 20, 2020

(30) Foreign Application Priority Data

Nov. 30, 2015 (GB) .................................. 1521109

(51) Int. Cl.
| | | |
|---|---|---|
| *C07D 487/04* | (2006.01) | |
| *A61P 25/28* | (2006.01) | |
| *A61P 35/00* | (2006.01) | |
| *C07D 401/12* | (2006.01) | |
| *C07D 403/12* | (2006.01) | |
| *C07D 413/12* | (2006.01) | |
| *C07D 417/04* | (2006.01) | |
| *C07D 417/14* | (2006.01) | |
| *C07D 513/04* | (2006.01) | |

(52) U.S. Cl.
CPC ............ *C07D 487/04* (2013.01); *A61P 25/28* (2018.01); *A61P 35/00* (2018.01); *C07D 401/12* (2013.01); *C07D 403/12* (2013.01); *C07D 413/12* (2013.01); *C07D 417/04* (2013.01); *C07D 417/14* (2013.01); *C07D 513/04* (2013.01)

(58) Field of Classification Search
USPC ...................................................... 514/210.2
See application file for complete search history.

(56) References Cited

FOREIGN PATENT DOCUMENTS

| WO | 9508534 A1 | 3/1995 |
|---|---|---|
| WO | 2009026197 A1 | 2/2009 |
| WO | 2009129365 A1 | 10/2009 |
| WO | 2009129370 A1 | 10/2009 |
| WO | 2009129371 A1 | 10/2009 |
| WO | 2015054555 A1 | 4/2015 |
| WO | 2016/046530 A1 | 3/2016 |
| WO | 2016156816 A1 | 10/2016 |
| WO | 2017/009650 A1 | 1/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |
| WO | 2017/158381 A1 | 9/2017 |
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |

OTHER PUBLICATIONS

The International Search Report and Written Opinion, dated Jan. 19, 2017, in the corresponding PCT Appl. No. PCT/GB2016/053742.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.
Clague et al., "Deubiquitylases from genes to organism", Physiol. Rev. 93:1289-1315, 2013.
Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.
Deaton et al, "Novel and potent cyclic cyanamide-based cathepsin K inhibitors", Bioorganic & Medicinal Chemistry Letters 15 (2005) 1815-1819.
Oballa et al, "A generally applicable method for assessing the electrophilicity and reactivity of diverse nitrile-containing compounds", Bioorganic & Medicinal Chemistry Letters 17 (2007) 998-1002.
Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

(Continued)

*Primary Examiner* — Kathrien A Cruz

(57) ABSTRACT

The present invention relates to novel compounds and methods for the manufacture of inhibitors of deubiquitylatin-enzymes (DUBs). In particular, the invention relates to the inhibition of ubiquitin C-terminal hydrolase 30 or Ubiquitin Specific Peptidase 30 (USP30). The invention further relates to the use of DUB inhibitors in the treatment of conditions involving mitochondrial dysfunction and cancer. Compounds of the invention include compounds having the formula (I) (I) or a pharmaceutically acceptable salt thereof, wherein $R^1$, $R^2$, $R^3$, m, L and X are as defined herein.

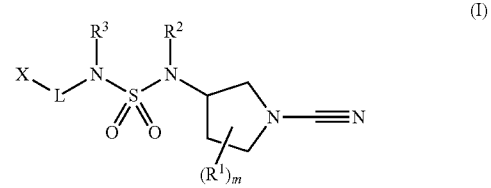

18 Claims, 1 Drawing Sheet

(56) References Cited

OTHER PUBLICATIONS

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.
Bingol et al, "The mitochondrial deubiquitinase USP30 opposes parkin-mediated mitophagy", Nature vol. 510, 370-375, 2014.
Liang et al, "USP30 deubiquitylates mitochondrial Parkin substrates and restricts apoptotic cell death", EMBO Reports, 1-10, 2015; DOI 10.15252/embr.201439820.
Bedford et al., "Ubiquitin-like protein conjugation and the ubiquitin—proteasome system as drug targets," Nat Rev Drug Discov. Jan. 2011;10(1):29-46.
Ward et al., "Quantitative Chemical Proteomic Profiling of Ubiquitin Specific Proteases in Intact Cancer Cells," ACS Chem. Biol. 2016, 11, 3268-3272.

USP30 kinetic assay for high throughput screening of compounds using an isopeptide linked substrate
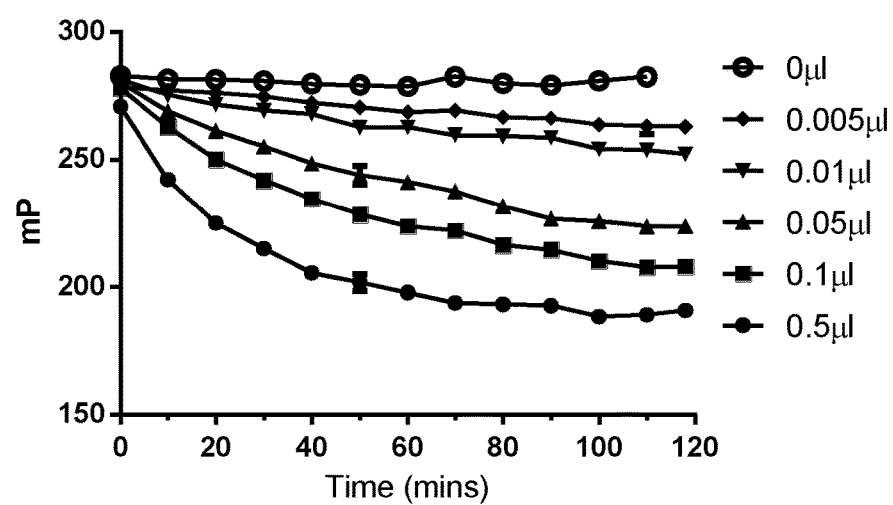

1-CYANO-PYRROLIDINE DERIVATIVES AS INHIBITORS OF USP30

CROSS-REFERENCE TO RELATED APPLICATIONS

This application is a National Stage Application of PCT/GB2016/053742 filed Nov. 29, 2016, which claims priority from UK Patent Application No. 1521109.7, filed on Nov. 30, 2015. The priority of said PCT and UK Patent Application are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of ubiquitin C-terminal hydrolase 30 or Ubiquitin Specific Peptidase 30 (USP30). The invention further relates to the use of DUB inhibitors in the treatment of conditions involving mitochondrial dysfunction and in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis (Clague et al., Physiol Rev 93:1289-1315, 2013).

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy (Bingol et al., Nature 510:370-5, 2014).

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death (Liang et al., EMBO Reports 2015 DOI: 10.15252/embr.201439820). USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011). Thus, there is a need for compounds and pharmaceutical compositions to inhibit DUBs such as USP30 for the treatment of indications where DUB activity is observed, including, although not limited to, conditions involving mitochondrial dysfunction and cancer.

SUMMARY OF THE INVENTION

In accordance with a first aspect of the invention there is provided a compound of formula (I)

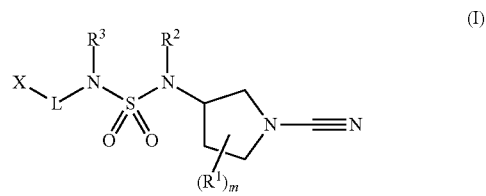

or a pharmaceutically acceptable salt thereof, wherein:
m is an integer from 0 to 3;
each occurrence of $R^1$ is independently selected from the group consisting of fluorine, cyano, hydroxyl, amino, optionally substituted $C_1$-$C_6$ alkyl, optionally substituted $C_1$-$C_6$ alkoxy or an optionally substituted 3 to 6 membered ring;

$R^2$ represents hydrogen, optionally substituted $C_1$-$C_6$ alkyl, an optionally substituted ring, or $R^2$ together with $R^3$ forms an optionally further substituted ring;

$R^3$ represents hydrogen, optionally substituted $C_1$-$C_6$ alkyl, an optionally substituted ring, or $R^3$ together with $R^2$ forms an optionally further substituted ring, or $R^3$ together with X forms an optionally substituted ring;

L represents a bond, an optionally substituted $C_1$-$C_6$ alkylene or optionally substituted —$C_2$-$C_6$ alkenylene linker or forms part of a ring with X and $R^3$;

X represents hydrogen, optionally substituted $C_1$-$C_6$ alkyl, an optionally substituted ring, or X together with $R^3$ forms an optionally substituted ring.

In one aspect, the invention also relates to pharmaceutical compositions comprising the compounds of the present invention and one or more pharmaceutically acceptable excipients.

In another aspect, the compounds of the invention are useful for the treatment of cancer or a disease or condition involving mitochondrial dysfunction.

BRIEF DESCRIPTION OF THE FIGURES

FIG. 1 is a graph showing proteolytic activity of USP30 measured using a fluorescence polarisation assay. Various volumes of purified USP30 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of formula (I)), includes reference to formula (I) and formula (II) including any sub-generic embodiments thereof, e.g. formula (IA), (IB) or (IC) (including all sub-generic embodiments thereof).

Where any group of the compounds of formula (I) or (II) have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, alkenylene or alkynyl substituent (or linker) group or an alkyl, alkenyl moiety in a substituent group may be linear or branched. Alkyl, alkylene, alkenyl and alkenylene chains may also include intervening heteroatoms such as oxygen, $C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group.

For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^1$, $R^2$, $R^3$, R', R'', R''', $R^a$, $R^b$, $R^c$, $R^d$, $R^e$, $R^f$, $R^g$, $R^h$ and $R^i$, $Q^1$, $Q^2$, $Q^3$, X, and within the definition of substituents for $R^4$, $R^5$ and $R^6$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of R', R'', R''', $R^a$, $R^b$, $R^c$, $R^d$, $R^e$, $R^f$, $R^g$, $R^h$ and $R^i$, $Q^1$, $Q^2$, $Q^3$, L, and within the definition of substituents for $R^4$, $R^5$ and $R^6$, may be unsubstituted or substituted with one or more of the substituents defined herein.

$C_2$-$C_6$ alkenyl refers to a linear or branched hydrocarbon chain radical containing at least two carbon atoms and at least one double bond. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl within the definitions of $Q^1$, $Q^2$, $Q^3$, and within the definition of substituents for $R^4$, $R^5$ and $R^6$, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^1$, $Q^2$, $Q^3$, $Q^4$, $Q^5$, $Q^6$ and L, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl within the definitions of $Q^1$, $Q^2$, $Q^3$, and within the definition of substituents for $R^4$, $R^5$ and $R^6$, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —OC$_{1-6}$ alkyl. In one instance, the alkoxy is linked through oxygen to the remainder of the molecule but the alkoxy group contains a further oxygen atom, for example —OCH$_2$CH$_2$OCH$_3$. Unless specified otherwise, C$_1$-C$_6$ alkoxy and C$_1$-C$_3$ alkoxy within the definitions R$^1$, R$^2$, R$^3$, R', R'', R''', Q$^1$, Q$^2$, Q$^3$ and X may be unsubstituted or substituted with one or more of the substituents defined herein. Examples of substituted C$_1$-C$_6$ alkoxy therefore include OCF$_3$, OCHF$_2$, OCH$_2$CF$_3$ and OCH$_2$COCH$_3$. For example, OCF$_3$, OCH$_2$CF$_3$ and OCH$_2$COCH$_3$.

The term "halogen" or "halo" refers to chlorine, bromine, fluorine or iodine atoms, in particular chlorine or fluorine atoms.

The term "oxo" means =O.

The term "amino" means —NH$_2$.

For the avoidance of doubt it will be understood that the cycloalkyl, heterocyclyl, aryl and heteroaryl rings disclosed herein and within the definitions of R$^1$, R$^2$, R$^3$, R$^4$, R$^5$, R$^6$, R$^a$, R$^b$, R$^c$, R$^d$, R$^e$, R$^f$, R$^g$, R$^h$ and R$^i$, X, ring A, ring B, ring C, and within the definition of substituents for R$^4$, R$^5$ and R$^6$, do not include any unstable ring structures or, in the case of heteroaryl and heterocyclic ring systems, any O—O, O—S or S—S bonds. The ring systems may be monocyclic, bicyclic or tricyclic. Bicyclic and tricyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example C$_3$-C$_{10}$ cycloalkyl refers to a monocyclic or bicyclic hydrocarbon ring containing 3 to 10 carbon atoms.

Examples of C$_3$-C$_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of R$^1$, R$^2$, R$^3$, R$^4$, R$^5$, R$^6$, R$^a$, R$^b$, R$^c$, R$^d$, R$^e$, R$^f$, R$^g$, R$^h$ and R$^i$, X, ring C, and within the definition of substituents for R$^4$, R$^5$ and R$^6$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of R$^1$, R$^2$, R$^3$, R$^4$, R$^5$, R$^6$, R$^a$, R$^b$, R$^c$, R$^d$, R$^e$, R$^f$, R$^g$, R$^h$ and R$^i$, X, ring C, and within the definition of substituents for R$^4$, R$^5$ and R$^6$, may be unsubstituted or substituted with one or more of the substituents defined herein.

"Heteroaryl" as used herein means a polyunsaturated, monocyclic, bicyclic or tricyclic 5 to 14 membered, or 4 to 10 membered, or 5 to 10 membered, aromatic moiety containing at least one and up to 5 heteroatoms, particular 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternised. A heteroaryl ring can be a single aromatic ring or a fused bicyclic ring where the bicyclic ring system can be aromatic, or one of the fused rings is aromatic and the other is at least partially saturated. In such instances, attachment of the bicyclic ring to the group it is a substituent of, e.g. with respect to the cyanopyrrolidine core, is via the aromatic ring of the bicycle. In one example, a bicyclic heteroaryl is one in which the entire fused ring system is aromatic. A bicyclic heteroaryl can have the at least one heteroatom in either of the fused rings, i.e. it can be attached to the group it is a substituent of either via a heteroatom containing ring or a carbon only containing ring. The point of attachment of heteroaryl to the group it is a substituent of can be via a carbon atom or a heteroatom (e.g. nitrogen). In instances where ring B of formula (IB) is a heteroaryl, the ring incorporating the sulphamide nitrogen is an aromatic ring which may be fused to a further aromatic or partially saturated ring. In instances where ring C of formula (IC) is a heteroaryl, the ring is an aromatic ring which may be fused to a further aromatic or partially saturated ring. Examples of heteroaryl rings include pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, quinoxalinyl and carbazolyl. Unless specified otherwise, heteroaryl within the definitions of R$^1$, R$^2$, R$^3$, R$^4$, R$^5$, R$^6$, R$^a$, R$^b$, R$^c$, R$^d$, R$^e$, R$^f$, R$^g$, R$^h$ and R$^i$, X, ring B, ring C, and within the definition of substituents for R$^4$, R$^5$ and R$^6$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring, a bicyclic saturated or partially unsaturated ring, wherein the bicyclic ring system is non-aromatic, or a tricyclic partially unsaturated ring, the mono-, bi- or tricyclic ring having, for example, 3 to 14 members, or 3 to 10 members, or 4 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocyclyl is a bicyclic ring, attachment to the group it is a substituent of relative to the cyanopyrrolidine core is via the non-aromatic ring, wherein the non-aromatic ring may be fused to a further ring which may be aromatic or non-aromatic. For example, R$^2$ and R$^3$ may together form a heterocylic ring which incorporates the sulphamide nitrogens and sulphur, and which is also referred to as ring A in formula (IA). In the case where the heterocylcyl is a bicyclic ring, the second ring (i.e. the ring portion that does not include —N—S(O$_2$)—N—) can be aromatic, e.g. a fused phenyl, pyridyl, pyrazolyl, or the like. In the case of a tricyclic heterocyclic ring, the heterocyclic ring may form the central ring and be fused to two further ring systems which are preferably aromatic. The heterocyclyl may be linked through carbon or a heteroatom to the remainder of the molecule and the link may be via the central heterocyclyl or either of the fused terminal rings. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydrothiazolopyridinyl, tetrahydroquinolinyl, benzomorpholinyl, tetrahydroisoquinolinyl and carbazolyl. Unless specified otherwise, heterocyclyl within the definitions of $R^1$, $R^2$, $R^3$, $R^4$, $R^5$, $R^6$, $R^a$, $R^b$, $R^c$, $R^d$, $R^e$, $R^f$, $R^g$, $R^h$ and $R^i$, X, ring A, ring B, ring C, and within the definition of substituents for $R^4$, $R^5$ and $R^6$, may be unsubstituted or substituted with one or more of the substituents defined herein. Substituted heterocyclyl rings include for example 4,5-dihydro-1H-maleimido, tetramethylenesulfoxide and hydantoinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl and $C_1$-$C_3$ alkyl), $C_1$-$C_6$ alkoxy (including $C_1$-$C_4$ alkoxy and $C_1$-$C_3$ alkoxy), —$C_2$-$C_6$ alkenyl and —$C_2$-$C_6$ alkynyl, for example within the definitions of $R^1$, $R^2$, $R^3$, R', R", R''', $R^a$, $R^b$, $R^c$, $R^d$, $R^e$, $R^f$, $R^g$, $R^h$ and $R^i$, $Q^1$, $Q^2$, $Q^3$, X, and within the definition of substituents for $R^4$, $R^5$ and $R^6$, and $C_1$-$C_6$ alkylene (including $C_1$-$C_3$ alkylene) and $C_2$-$C_6$ alkenylene, for example within the definitions of R', R", R''', $R^a$, $R^b$, $R^c$, $R^d$, $R^e$, $R^f$, $R^g$, $R^h$ and $R^i$, $Q^1$, $Q^2$, $Q^3$ and L, include $C_1$-$C_6$ alkoxy, halogen, hydroxyl, thiol, cyano, amino, nitro and $SF_5$ (a known mimetic of nitro), in particular, halogen (preferably fluorine or chlorine), hydroxyl and cyano. For example, suitable substituents include halogen, hydroxyl, thiol, cyano, amino, nitro and $SF_5$, in particular, halogen (preferably fluorine or chlorine), hydroxyl and cyano.

Examples of suitable substituents for "substituted" and "optionally substituted" rings, i.e. cycloalkyl, heterocyclyl, aryl and heteroaryl rings, for example within the definitions of $R^1$, $R^2$, $R^3$, $R^4$, $R^5$, $R^6$, $R^a$, $R^b$, $R^c$, $R^d$, $R^e$, $R^f$, $R^g$, $R^h$ and $R^i$, X, ring A, ring B, ring C, and within the definition of substituents for $R^4$, $R^5$ and $R^6$, include halogen, $C_1$-$C_6$ alkyl or $C_1$-$C_3$ alkyl, hydroxy, $C_1$-$C_6$ alkoxy or $C_1$-$C_3$ alkoxy, cyano, amino, nitro or $SF_5$ (a known mimetic of nitro), aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halo. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Examples of suitable substituents for "substituted" and "optionally substituted" rings include in particular, fluorine, chlorine, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents independently selected from halogen, hydroxyl, thiol, cyano, amino, nitro and $SF_5$. In particular, suitable substituents for "substituted" and "optionally substituted" rings disclosed herein include fluorine, chlorine, oxo, cyano, $C_1$-$C_3$ alkyl, $C_1$-$C_3$ alkoxy, wherein the alkyl or alkoxy is optionally substituted with one or more (e.g. one, two or three) substituents selected from halogen, hydroxyl, thiol, cyano, amino, nitro and $SF_5$, in particular, one or more fluorine.

Substituted groups thus include for example Br, Cl, F, CN, Me, Et, Pr, OMe, OEt, OPr, C(CH$_3$)$_3$, CH(CH$_3$)$_2$, CF$_3$, OCF$_3$, C(O)NHCH$_3$, cyclopropyl, phenyl, etc. In the case of aryl groups, the substitutions may be in the form of rings from adjacent carbon atoms in the aryl ring, for example cyclic acetals such as O—CH$_2$—O.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Included herein is the compound according to formula (II)

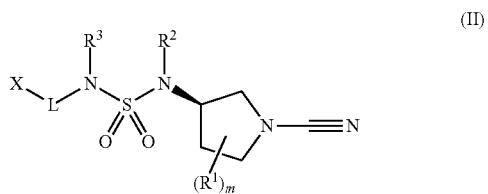

(II)

or a pharmaceutically acceptable salt thereof, wherein m is an integer from 0 to 3; each occurrence of $R^1$ is independently selected from the group consisting of fluorine, cyano, hydroxyl, amino, optionally substituted $C_1$-$C_6$ alkyl, optionally substituted $C_1$-$C_6$ alkoxy or an optionally substituted 3 to 6 membered ring;

$R^2$ represents hydrogen, optionally substituted $C_1$-$C_6$ alkyl, an optionally substituted ring, or $R^2$ together with $R^3$ forms an optionally further substituted ring;

$R^3$ represents hydrogen, optionally substituted $C_1$-$C_6$ alkyl, an optionally substituted ring, or $R^3$ together with $R^2$ forms an optionally further substituted ring, or $R^3$ together with X forms an optionally substituted ring;

L represents a bond, an optionally substituted $C_1$-$C_6$ alkylene or optionally substituted —$C_2$-$C_6$ alkenylene linker or forms part of a ring with X and $R^3$;

X represents hydrogen, optionally substituted $C_1$-$C_6$ alkyl, an optionally substituted ring, or X together with $R^3$ forms an optionally substituted ring.

In particular, $R^1$ is independently selected from the group consisting of fluorine, cyano, hydroxyl, amino, optionally substituted $C_1$-$C_6$ alkyl and optionally substituted $C_1$-$C_6$ alkoxy.

Also included herein is the compound according to formula (IIA)

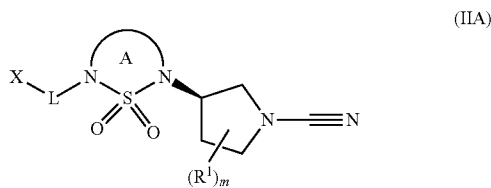

(IIA)

or a pharmaceutically acceptable salt thereof, wherein:
m is an integer from 0 to 3;
each occurrence of $R^1$ is independently selected from the group consisting of fluorine, cyano, hydroxyl, amino, optionally substituted $C_1$-$C_6$ alkyl, optionally substituted $C_1$-$C_6$ alkoxy or an optionally substituted 3 to 6 membered ring;

ring A represents an optionally further substituted 4 to 10 membered heterocyclyl ring;

L represents a bond, an optionally substituted $C_1$-$C_6$ alkylene or an optionally substituted —$C_2$-$C_6$ alkenylene linker;

X represents hydrogen, optionally substituted $C_1$-$C_6$ alkyl or an optionally substituted ring.

In particular, $R^1$ is independently selected from the group consisting of fluorine, cyano, hydroxyl, amino, optionally substituted $C_1$-$C_6$ alkyl and optionally substituted $C_1$-$C_6$ alkoxy.

It will be understood from the structure of formulas (II) and (IIA), that the bond attaching the hydrogen, or $R^1$ as the case may be, to the C3 position of the pyrrolidine ring will be represented by a dash bond, i.e. the compound will have (R) configuration.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

The compounds described herein are characterised by a cyanopyrrolidine core with a sulphamide group attached to the cyanopyrrolidine ring, wherein the sulphamide group may be substituted with an optionally substituted ring.

In accordance with a first aspect of the invention there is provided a compound of formula (I)

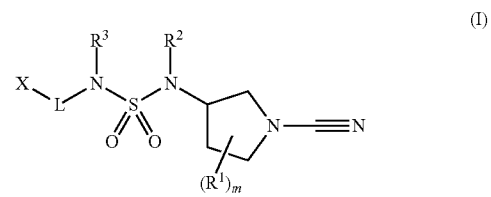

or a pharmaceutically acceptable salt thereof, wherein:
m is an integer from 0 to 3;
each occurrence of $R^1$ is independently selected from the group consisting of fluorine, cyano, hydroxyl, amino, optionally substituted $C_1$-$C_6$ alkyl, optionally substituted $C_1$-$C_6$ alkoxy or an optionally substituted 3 to 6 membered ring;
$R^2$ represents hydrogen, optionally substituted $C_1$-$C_6$ alkyl, an optionally substituted ring, or $R^2$ together with $R^3$ forms an optionally further substituted heterocyclyl ring;
$R^3$ represents hydrogen, optionally substituted $C_1$-$C_6$ alkyl, an optionally substituted ring, or $R^3$ together with $R^2$ forms an optionally further substituted ring, or $R^3$ together with X forms an optionally substituted heterocyclyl or heteroaryl ring;
L represents a covalent bond, an optionally substituted $C_1$-$C_6$ alkylene or optionally substituted —$C_2$-$C_6$ alkenylene linker or forms part of a ring with X and $R^3$;
X represents hydrogen, optionally substituted $C_1$-$C_6$ alkyl, an optionally substituted ring, or X together with $R^3$ forms an optionally substituted ring.

m is an integer from 0 to 3 (i.e., 0, 1, 2 or 3). Preferably, m is 0, 1 or 2. In particular, m is 0 or 1.

More particularly, m is 0. When m is 0, $R^1$ is absent.

Each occurrence of $R^1$ may be selected from the group consisting of fluorine, cyano, hydroxyl, amino, optionally substituted $C_1$-$C_6$ alkyl, optionally substituted $C_1$-$C_6$ alkoxy or an optionally substituted 3 to 6 membered cycloalkyl, heterocyclyl, aryl or heteroaryl ring. The 3 to 6 membered cycloalkyl, heterocyclyl, aryl or heteroaryl ring may be defined according to the definitions of cycloalkyl, heterocyclyl, aryl or heteroaryl found herein. In particular, $R^1$ may be selected from the group consisting of fluorine, cyano, hydroxyl, amino, optionally substituted $C_1$-$C_6$ alkyl or optionally substituted $C_1$-$C_6$ alkoxy. Preferably, $R^1$ is fluorine, $C_1$-$C_4$ alkyl or $C_1$-$C_3$ alkyl wherein the alkyl is optionally substituted with one or more (e.g. one, two or three) fluorine or $C_1$-$C_3$ alkoxy optionally substituted with one or more (e.g. one, two or three) fluorine. In particular, $R_1$ is methyl.

The compounds may be in the form where m is 0 and $R^1$ is therefore absent. In such cases the compounds may be of formula (IAA):

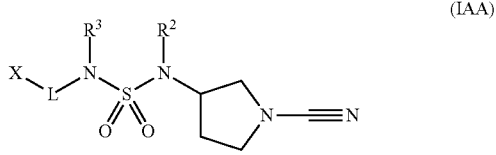

(IAA)

or a pharmaceutically acceptable salt thereof, wherein:
$R^2$ represents hydrogen, optionally substituted $C_1$-$C_6$ alkyl, an optionally substituted ring, or $R^2$ together with $R^3$ forms an optionally substituted heterocyclyl ring;
$R^3$ represents hydrogen, optionally substituted $C_1$-$C_6$ alkyl, an optionally substituted ring, or $R^3$ together with $R^2$ forms an optionally substituted ring, or $R^3$ together with X forms an optionally substituted ring;
L represents a covalent bond, an optionally substituted $C_1$-$C_6$ alkylene or optionally substituted —$C_2$-$C_6$ alkenylene linker or forms part of a ring with X and $R^3$;
X represents hydrogen, optionally substituted $C_1$-$C_6$ alkyl, an optionally substituted ring, or X together with $R^3$ forms an optionally substituted heterocyclyl or heteroaryl ring.

$R^2$ and $R^3$ may together form a 4 to 10 membered (e.g. 4, 5, 6, 7, 8, 9 or 10 membered) heterocyclic ring which may be optionally further substituted with one or more -$Q^2$-$(R^5)_p$. The 4 to 10 membered heterocyclic ring may be defined according to the definition of heterocyclic ring found herein. The heterocyclic ring may be monocyclic or bicyclic. Alternatively, $R^2$ and $R^3$ each independently represent hydrogen, optionally substituted $C_1$-$C_6$ alkyl, e.g. $C_1$-$C_4$ alkyl or $C_1$-$C_3$ alkyl, or an optionally substituted 3 to 10 membered (e.g. 3, 4, 5, 6, 7, 8, 9, or 10 membered) cycloalkyl, heterocyclyl, aryl or heteroaryl ring. The 3 to 10 membered cycloalkyl, heterocyclyl, aryl or heteroaryl ring may be defined according to the definitions of cycloalkyl, heterocyclyl, aryl and heteroaryl ring found herein. The 3 to 10 membered ring may be monocyclic or bicyclic. Alternatively, $R^2$ represents hydrogen or an optionally substituted $C_1$-$C_6$ alkyl, e.g. $C_1$-$C_4$ alkyl or $C_1$-$C_3$ alkyl, and $R^3$ together with X forms a 4 to 10 membered heterocyclyl or heteroaryl ring which may be optionally substituted with one or more -$Q^3$-$(R^8)_q$. The 4 to 10 membered cycloalkyl, heterocyclyl, aryl or heteroaryl ring may be defined according to the definitions of cycloalkyl, heterocyclyl, aryl or heteroaryl ring found herein. The 4 to 10 membered ring may be monocyclic or bicyclic.

When $R^2$ and $R^3$ together with the nitrogen atoms to which they are attached form a monocyclic or bicyclic 4 to 10 membered heterocyclyl ring, the ring is optionally further substituted (i.e. in addition to the dioxo substitution on the sulphur atom) with one or more (e.g. one, two, three or four) of -$Q^2$-$(R^5)_p$, in particular, the ring is either unsubstituted or substituted with one or two of -$Q^2$-$(R^5)_p$ wherein each -$Q^2$-$(R^5)_p$ is the same or different. The 4 to 10 membered heterocyclyl may be defined according to the definitions of heterocyclyl ring found herein. In particular, the 4 to 10 membered heterocyclyl may be referred to as "ring A" and may be selected from 1-dioxido-1,2,5-thiadiazolidin-2-yl, 1,1-dioxido-1,2,6-thiadiazinan-2-yl, 2,2-dioxidobenzo[c][1,2,5]thiadiazol-1(3H)-yl and 1,4-dihydro-3H-benzo[c][1,2,6]thiadiazin-3-yl.

L represents a covalent bond, an optionally substituted $C_1$-$C_6$ alkylene or optionally substituted —$C_2$-$C_6$ alkenylene linker or forms part of a heterocyclyl or heteroaryl ring with X and $R^3$. Preferably, L represents a covalent bond or $C_1$-$C_3$ alkylene, wherein the $C_1$-$C_3$ alkylene is optionally substituted with one or more (e.g. one, two or three) substituents selected from halogen, hydroxyl, thiol, cyano, amino, nitro and $SF_5$. When $R^3$ together with X forms an optionally substituted heterocyclyl or heteroaryl ring, L forms part of the ring and preferably represents a covalent bond.

X represents hydrogen, optionally substituted $C_1$-$C_6$ alkyl (e.g. $C_1$-$C_4$ alkyl or $C_1$-$C_3$ alkyl), a 3 to 14 membered cycloalkyl, heterocyclyl, aryl or heteroaryl ring which may be optionally substituted with one or more -$Q^1$-$(R^4)_n$, or X together with $R^3$ and a sulphamide nitrogen forms a 4 to 10 membered heterocylyl or heteroaryl ring which may be optionally substituted with one or more -$Q^3$-$(R^6)_q$.

When X together with $R^3$, and the sulphamide nitrogen to which they are attached, form a 4 to 10 membered heterocyclyl or heteroaryl ring, the ring may be unsubstituted or substituted with one or more (e.g. one, two, three or four) of -$Q^3$-$(R^6)_q$, in particular, the ring is either unsubstituted or substituted with one or two of -$Q^3$-$(R^6)_q$ wherein each -$Q^3$-$(R^6)_q$ is the same or different. The 4 to 10 membered heterocyclyl or heteroaryl ring may be defined according to the definitions of heterocyclyl and heteroaryl found herein and may be monocyclic or bicyclic. In particular, the 4 to 10 membered heterocyclyl or heteroaryl ring may be referred to as "ring B" and may be selected from piperidinyl, piperazinyl, indolinyl, benzopiperidinyl, dihydroisoquinolinyl and dihydropyrazolo[1,5-a]pyrimidinyl.

When X represents a 3 to 14 membered cycloalkyl, heterocyclyl, aryl or heteroaryl ring, the ring is optionally substituted with one or more (e.g. one, two, three or four) of -$Q^1$-$(R^4)_n$, in particular, the ring is either unsubstituted or substituted with one or two of -$Q^1$-$(R^4)_n$ wherein each -$Q^1$-$(R^4)_n$ is the same or different. The 3 to 14 membered cycloalkyl, heterocyclyl, aryl or heteroaryl ring may be defined according to the definitions of cycloalkyl, heterocyclyl, aryl or heteroaryl ring found herein and may be monocyclic, bicyclic or tricyclic. In particular, the 3 to 14 membered cycloalkyl, heterocyclyl, aryl or heteroaryl ring may be referred to as "ring C" and may be selected from phenyl and benzimidazole.

In all cases described herein, n, p and q each independently represent 0 or 1.

$Q^1$, $Q^2$ and $Q^3$ each independently represent halogen, cyano, oxo, nitro, —OR', —SR', —NR'R'', —CONR'R'', —NR'COR'', —NR'CONR''R''', —COR', —C(O)OR', —SO$_2$R', —SO$_2$NR'R'', —NR'SO$_2$R'', NR'SO$_2$NR''R''', —NR'C(O)OR'', optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —SO$_2$—, —CO—, —C(O)O—, —CONR'—, —NR'—, —NR'CO—, —NR'CONR''—, —SO$_2$NR'—, —NR'SO$_2$—, —NR'SO$_2$NR''—, —NR'C(O)O—, —NR'C (O)OR''', optionally substituted $C_1$-$C_6$ alkylene, or optionally substituted —$C_2$-$C_6$ alkenylene.

R', R'' and R''' each independently represent hydrogen, optionally substituted $C_1$-$C_6$ alkyl, optionally substituted $C_1$-$C_6$ alkoxy or optionally substituted $C_1$-$C_6$ alkylene.

When n, p or q is 1, then $R^4$, $R^5$ and $R^6$ respectively represent an optionally substituted 3 to 10 membered heterocyclyl, cycloalkyl, heteroaryl or aryl ring (when n is 0, $Q^1$ is present and $R^4$ is absent; when p is 0, $Q^2$ is present and $R^5$ is absent; when q is 0, $Q^3$ is present and $R^6$ is absent).

In particular, $Q^1$, $Q^2$ and $Q^3$ each independently represent halogen, $C_1$-$C_6$ alkyl, preferably a $C_1$-$C_4$ alkyl or $C_1$-$C_3$ alkyl, a covalent bond or $C_1$-$C_6$ alkylene, preferably a $C_1$-$C_4$ alkylene or $C_1$-$C_3$ alkylene, wherein the alkyl or alkylene may be optionally substituted with one or more (e.g. one, two or three) fluorine.

In particular, R', R'' and R''' each independently represent hydrogen, $C_1$-$C_4$ alkyl or $C_1$-$C_3$ alkyl, $C_1$-$C_4$ alkoxy or $C_1$-$C_3$ alkoxy, or $C_1$-$C_3$ alkylene, wherein the alkyl, alkoxy and alkylene are optionally substituted with one or more (e.g. one, two or three) fluorine.

$R^4$, $R^5$ and $R^6$ each independently represent an optionally substituted 3 to 10 membered heterocyclyl, cycloalkyl, heteroaryl or aryl ring. The ring may be monocyclic or bicyclic. The ring may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, benzomorpholinyl and tetrahydroisoquinolinyl.

$R^4$, $R^5$ and $R^6$ may each independently represent an optionally substituted 4, 5 or 6 membered heterocyclyl, cycloalkyl, heteroaryl or aryl ring.

Alternatively, $R^4$, $R^5$ and $R^6$ may each independently represent an optionally substituted 9 or 10 membered bicyclic heterocyclyl, cycloalkyl, heteroaryl or aryl ring.

In particular, $R^4$, $R^5$ and $R^6$ each independently represent a 3 to 10 membered cycloalkyl, heterocyclyl, aryl or heteroaryl ring such as azetidinyl, morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolyl, isoindolinyl, pyrimidinyl, isoxazolyl, dihydroindenyl, dihydroisoquinolinyl, tetrahydropyranyl, phenyl, oxadiazolyl, triazolyl, isoquinolinyl, indazolyl, pyrazolopyridinyl, pyrazolopyrimidinyl, imidazolpyridinyl, imidazopyrimidinyl, imidazopyrazinyl, oxazolyl and quinolinyl, which may be optionally substituted.

More particularly, $R^4$, $R^5$ and $R^6$ each independently represent an optionally substituted 4, 5 or 6 membered cycloalkyl, heterocyclyl, aryl or heteroaryl ring. Each $R^4$, $R^5$ and $R^6$ ring may be independently selected from the group consisting of phenyl, pyridinyl, pyrazolyl, morpholinyl, isoxazolyl, azetidinyl, pyrrolidinyl and piperazinyl. In particular, each $R^4$, $R^5$ and $R^6$ ring may be independently a substituted or unsubstituted phenyl or pyridinyl.

In all cases described herein, $R^4$ may be substituted with one or more (e.g. one, two or three) substituents independently selected from halogen, cyano, oxo, nitro —$OR^a$, —$SR^a$, —$NR^aR^b$, —$CONR^aR^b$, —$NR^aCOR^b$, —$NR^a$-$CONR^bR^c$, —$COR^a$, —$C(O)OR^a$, —$SO_2R^a$, —$SO_2NR^aR^b$, —$NR^aSO_2R^b$, $NR^aSO_2NR^bR^c$, —$NR^aC(O)OR^b$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^4$-$R^a$, -$Q^4$-$NR^aCONR^bR^c$, -$Q^4$-$NR^aR^b$, $Q^4$-$COR^a$, -$Q^4$-$NR^aCOR^b$, -$Q^4$-$NR^aC(O)OR^b$, -$Q^4$-$SO_2R^a$, $Q^4CONR^aR^b$, -$Q^4$-$CO_2R^a$-$Q^4$-$SO_2NR^aR^b$, -$Q^4$-$NR^aSO_2R^b$ and -$Q^4$-$NR^aSO_2NR^bR^c$, wherein the alkyl, alkoxy, alkenyl or alkynyl are optionally substituted with one or more substituents selected from halogen, hydroxyl, thiol, cyano, amino, nitro and $SF_5$.

In all cases described herein, $R^5$ may be substituted with one or more (e.g. one, two or three) substituents independently selected from halogen, cyano, oxo, nitro —$OR^d$, —$SR^d$, —$NR^dR^e$, —$CONR^dR^e$, —$NR^dCOR^e$, —$NR^dCONR^eR^f$, —$COR^d$, —$C(O)OR^d$, —$SO_2R^d$, —$SO_2NR^dR^e$, —$NR^dSO_2R^e$, $NR^dSO_2NR^eR^f$, —$NR^dC(O)OR^e$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^5$-$R^d$, -$Q^5$-$NR^dCONR^eR^f$, -$Q^5$-$NR^dR^e$, -$Q^5$-$COR^d$, -$Q^5$-$NR^dCOR^e$, -$Q^5$-$NR^dC(O)OR^e$, -$Q^5$-$SO_2R^d$, $Q^5$-$CONR^dR^e$, -$Q^5$- $CO_2R^d$, -$Q^5$-$SO_2NR^dR^e$, -$Q^5$-$NR^dSO_2R^e$ and -$Q^5$-$NR^dSO_2NR^eR^f$, wherein the alkyl, alkoxy, alkenyl or alkynyl are optionally substituted with one or more substituents selected from halogen, hydroxyl, thiol, cyano, amino, nitro and $SF_5$.

In all cases described herein, $R^6$ may be substituted with one or more (e.g. one, two or three) substituents independently selected from halogen, cyano, oxo, nitro —$OR^g$, —$SR^g$, —$NR^gR^h$, —$CONR^gR^h$, —$NR^gCOR^h$, —$NR^g$-$CONR^hR^i$, —$COR^g$, —$C(O)OR^g$, —$SO_2R^g$, —$SO_2NR^gR^h$, —$NR^gS_2R^h$, $NR^gSO_2NR^hR^i$, —$NR^gC(O)OR^h$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^6$-$R^g$, -$Q^6$-$NR^gCONR^hR^i$, -$Q^6$-$NR^gR^h$, -$Q^6$-$COR^g$, -$Q^6$-$NR^gCOR^h$, -$Q^6$-$NR^gC(O)OR^h$, -$Q^6$-$SO_2R^g$, -$Q^6$-$CONR^gR^h$, -$Q^6$- $CO_2R^g$, -$Q^6$-$SO_2NR^gR^h$, -$Q^6$-$NR^gSO_2R^h$ and -$Q^6$-$NR^gSO_2NR^hR^i$, wherein the alkyl, alkoxy, alkenyl or alkynyl are optionally substituted with one or more substituents selected from halogen, hydroxyl, thiol, cyano, amino, nitro and $SF_5$.

$Q^4$, $Q^5$ and $Q^6$ each independently represent a covalent bond, an oxygen atom, a sulphur atom, —SO—, —$SO_2$—, —CO—, optionally substituted $C_1$-$C_6$ alkylene or optionally substituted $C_2$-$C_6$ alkenylene; and $R^a$, $R^b$, $R^c$, $R^d$, $R^e$, $R^f$, $R^g$, $R^h$ and $R^i$ each independently represent hydrogen, $C_1$-$C_6$ alkyl, optionally substituted heterocyclyl, optionally substituted heteroaryl, optionally substituted aryl, or an optionally substituted cycloalkyl, wherein the alkyl is optionally substituted with one or more (e.g. one, two or three) substituents selected from halogen, hydroxyl, thiol, cyano, amino, nitro and $SF_5$ and wherein the heterocyclyl, cycloalkyl, heteroaryl or aryl are optionally substituted in accordance with the definitions provided herein.

The present invention further relates to compounds of formula (I), or a pharmaceutically acceptable salt thereof, wherein:

m is 0 or 1;

$R^1$ is fluorine, $C_1$-$C_3$ alkyl or $C_1$-$C_3$ alkoxy, wherein the alkyl or alkoxy is optionally substituted with one or more fluorine;

R² is hydrogen, C₁-C₃ alkyl or together with R³ forms a 4 to 10 membered heterocyclyl optionally further substituted with one or two -Q²-(R⁵)$_p$ which can be the same of different;

R³ is hydrogen, C₁-C₃ alkyl or together with R² forms a 4 to 10 membered heterocyclyl optionally further substituted with one or two -Q²-(R⁵)$_p$ which can be the same or different, or R³ together with X forms a 5 to 10 membered heterocyclyl optionally substituted with one or two -Q¹-(R⁴)$_n$ which can be the same or different;

L is a covalent bond, C₁-C₃ alkylene or together with X and R³ forms a 5 to 10 membered heterocyclyl optionally substituted with one or two -Q¹-(R⁴)$_n$ which can be the same or different;

X represents hydrogen, C₁-C₃ alkyl, a 5 to 14 membered heterocyclyl, cycloalkyl, heteroaryl or aryl ring optionally substituted with one or two -Q¹-(R⁴)$_n$ which can be the same or different, or X together with R³ forms a 5 to 10 membered heterocyclyl optionally substituted with one or two -Q³-(R⁶)$_q$ which can be the same or different.

n, p, q each independently represent 0 or 1;

Q¹, Q², Q³, R⁴, R⁵, R⁶ are as defined above. In particular, Q¹, Q² and Q³ are independently selected from halogen, oxo, cyano, C₁-C₃ alkyl, C₁-C₃ alkoxy, covalent bond, an oxygen atom and C₁-C₃ alkylene, wherein the alkyl and alkoxy are optionally substituted with one or more substituents selected from fluorine and hydroxy. In particular, R⁴, R⁵ and R⁶ are each independently selected from a 4, 5 or 6 membered heterocyclyl, cycloalkyl, heteroaryl or aryl ring optionally substituted with halogen, C₁-C₃ alkyl or C₁-C₃ alkoxy wherein the alkyl or alkoxy is optionally substituted with one or more fluorine.

In each of formulas (IA), (IB) and (IC) below, m is an integer from 0 to 3 and each occurrence of R¹ is independently selected from the group consisting of fluorine, cyano, hydroxyl, amino, optionally substituted C₁-C₆ alkyl, optionally substituted C₁-C₆ alkoxy or an optionally substituted 3 to 6 membered ring. In particular, m is an integer from 0 to 3 and each occurrence of R¹ is independently selected from the group consisting of fluorine, cyano, hydroxyl, amino, optionally substituted C₁-C₆ alkyl or optionally substituted C₁-C₆ alkoxy.

m may be 0, 1 or 2. In particular, m is 0 or 1. More particularly, m is 0. When m is 0, R¹ is absent.

Each R¹ may be independently selected from the group consisting of fluorine, cyano, hydroxyl, amino, optionally substituted C₁-C₆ alkyl or optionally substituted C₁-C₆ alkoxy. Each R¹ may independently be fluorine, C₁-C₃ alkyl optionally substituted with one or more (e.g. one, two or three) fluorine or C₁-C₃ alkoxy optionally substituted with one or more (e.g. one, two or three) fluorine. In particular, R₁ is methyl.

In one aspect of the invention, when R² and R³ together form a 4 to 10 membered heterocyclic ring, the compound of formula (I) may be represented as the formula (IA):

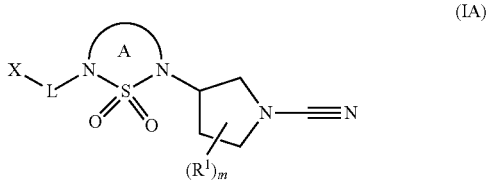

(IA)

or a pharmaceutically acceptable salt thereof, wherein:
L represents a bond, an optionally substituted C₁-C₆ alkylene or optionally substituted —C₂-C₆ alkenylene linker;

X represents hydrogen, optionally substituted C₁-C₆ alkyl or an optionally substituted ring; ring A represents an optionally further substituted 4 to 10 membered heterocyclic ring.

L represents a bond or an optionally substituted C₁-C₆ alkylene or optionally substituted —C₂-C₆ alkenylene. Preferably, L represents a bond or C₁-C₆ alkylene, for example, C₁-C₃ alkylene (e.g. methylene, ethylene, propylene), wherein the alkylene is optionally substituted with one or more (e.g. one, two or three) fluorine. In particular, L represents a bond or methylene.

In particular, X may represent an optionally substituted 3 to 14 membered cycloalkyl, heterocyclyl, aryl or heteroaryl ring.

When X represents a 3 to 14 membered ring it may be substituted with one or more (e.g. one, two, three or four) -Q¹-(R⁴)$_n$, wherein each -Q¹-(R⁴)$_n$ is the same or different and wherein:

n is 0 or 1;

Q¹ represents halogen, cyano, oxo, nitro, —OR', —SR', —NR'R'', —CONR'R'', —NR'COR'', —NR'CONR''R''', —COR', —C(O)OR', —SO₂R', —SO₂NR'R'', —NR'SO₂R'', NR'SO₂NR''R''', —NR'C(O)OR'', optionally substituted —C₁-C₆ alkyl, optionally substituted —C₁-C₆ alkoxy, optionally substituted —C₂-C₆ alkenyl, optionally substituted —C₂-C₆ alkynyl, a covalent bond, an oxygen atom, a sulphur atom, —SO—, —SO₂—, —CO—, —C(O)O—, —CONR'—, —NR'—, —NR'CO—, —NR'CONR''—, —SO₂NR'—, —NR'SO₂—, —NR'SO₂NR''—, —NR'C(O)O—, —NR'C(O)OR'', optionally substituted C₁-C₆ alkylene, or optionally substituted —C₂-C₆ alkenylene;

R', R'' and R''' each independently represent hydrogen, optionally substituted C₁-C₆ alkyl, optionally substituted C₁-C₆ alkoxy, or optionally substituted C₁-C₆ alkylene.

When n is 1, R⁴ represents an optionally substituted 3 to 10 membered heterocyclyl, cycloalkyl, heteroaryl or aryl ring (when n is 0, Q¹ is present and R⁴ is absent).

In particular, Q¹ may be selected from the group consisting of a covalent bond, halogen, oxo, C₁-C₆ alkyl or C₁-C₆ alkoxy wherein the alkyl or alkoxy is optionally substituted with one or more (e.g. one, two or three) substituents independently selected from halogen, hydroxyl, thiol, cyano, amino, nitro and SF₅, in particular fluorine. R⁴ may be an optionally substituted 5 or 6 membered cycloalkyl, heterocyclyl, aryl or heteroaryl ring. In particular, R⁴ is selected from phenyl, pyridinyl, pyrazolyl, morphinyl and isoxaxolyl.

X may be a 3 to 14 membered cycloalkyl, heterocyclyl, aryl or heteroaryl ring as defined under the definitions of 3 to 14 membered cycloalkyl, heterocyclyl, aryl and heteroaryl ring found herein. In particular, the 3 to 14 membered ring is selected from phenyl, 9H-carbazole, isoxazole, pyrazole, pyridine, benzimidazole, pyrimidine, benzomorpholine and pyrrolidine.

Preferably, the 3 to 14 membered cycloalkyl, heterocyclyl, aryl or heteroaryl ring is either unsubstituted or substituted with one, two, three or four of Q¹-(R⁴)$_n$. In particular, the 3 to 14 membered cycloalkyl, heterocyclyl, aryl or heteroaryl ring is either unsubstituted or substituted with one or two of Q¹-(R⁴)$_n$. Each occurrence of Q¹-(R⁴)$_n$ may be the same or different.

Preferably, when n is 1, Q¹ is a bond or C₁-C₆ alkylene, for example C₁-C₃ alkylene, and R⁴ is an optionally substituted 3 to 10 membered cycloalkyl, heterocyclyl, aryl or heteroaryl ring. In particular, R⁴ is a 4, 5 or 6 membered cycloalkyl, heterocyclyl, aryl or heteroaryl ring, for example, phenyl, pyridinyl, pyrazolyl, azetidinyl, pyrrolidinyl, morphinyl or isoxaxolyl.

Preferably, when n is 0, $Q^1$ is halogen, oxo or optionally substituted $C_1$-$C_6$ alkyl or $C_1$-$C_6$ alkoxy. In particular, $Q^1$ is halogen, oxo, $C_1$-$C_3$ alkyl or $C_1$-$C_3$ alkoxy, wherein the alkyl or alkoxy is either unsubstituted or substituted with one or more fluorine, e.g. $Q^1$ is $CF_3$.

In all cases described herein, $R^4$ may be substituted with one or more (e.g. one, two or three) substituents selected from halogen, cyano, oxo, nitro —$OR^a$, —$SR^a$, —$NR^aR^b$, —$CONR^aR^b$, —$NR^aCOR^b$, —$NR^aCONR^bR^c$, —$COR^a$, —$C(O)OR^a$, —$SO_2R^a$, —$SO_2NR^aR^b$, —$NR^aSO_2R^b$, $NR^aSO_2NR^bR^c$, —$NR^aC(O)OR^b$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^4$-$R^a$, -$Q^4$-$NR^aCONR^bR^c$, $Q^4$-$NR^aR^b$, -$Q^4$-$COR^a$, -$Q^4$-$NR^aCOR^b$, -$Q^4$-$NR^aC(O)OR^b$, -$Q^4$-$SO_2R^a$, $Q^4$-$CONR^aR^b$, -$Q^4$-$CO_2R^a$, -$Q^4$-$SO_2NR^aR^b$, -$Q^4$-$NR^aSO_2R^b$ and -$Q^4$-$NR^aSO_2NR^bR^c$, wherein the alkyl, alkoxy, alkenyl or alkynyl are optionally substituted with one or more substituents selected from halogen, hydroxyl, thiol, cyano, amino, nitro and $SF_5$.

$Q^4$ represents a covalent bond, an oxygen atom, a sulphur atom, —SO—, —$SO_2$—, —CO—, optionally substituted $C_1$-$C_6$ alkylene or optionally substituted $C_2$-$C_6$ alkenylene; and $R^a$, $R^b$ and $R^c$ each independently represent hydrogen, $C_1$-$C_6$ alkyl, optionally substituted heterocyclyl, optionally substituted heteroaryl, optionally substituted aryl, or an optionally substituted cycloalkyl, wherein the alkyl is optionally substituted with one or more substituents selected from halogen, hydroxyl, thiol, cyano, amino, nitro and $SF_5$ and wherein the heterocyclyl, cycloalkyl, heteroaryl or aryl are optionally substituted in accordance with the definitions provided herein.

For compounds of formula (IA), the 3 to 10 membered heterocyclyl, cycloalkyl, heteroaryl or aryl ring of $R^4$ may be unsubstituted or substituted with $C_1$-$C_6$ alkyl or $C_1$-$C_6$ alkoxy, in particular, $C_1$-$C_3$ alkyl or $C_1$-$C_3$ alkoxy, wherein the alkyl or alkoxy may be optionally substituted with one or more substituents selected from halogen, hydroxyl, thiol, cyano, amino, nitro and $SF_5$.

Ring A may be a monocyclic or bicyclic heterocyclic ring.

The 4 to 10 membered heterocyclic ring (ring A of formula (IA)) may be selected from saturated monocyclic rings such as 1,1-dioxido-1,2,5-thiadiazolidin-2-yl or 1,1-dioxido-1,2,6-thiadiazinan-2-yl or partially saturated bicyclic rings such as 2,2-dioxidobenzo[c][1,2,5]thiadiazol-1(3H)-yl, 1,4-dihydro-3H-pyrido[3,4-c][1,2,6]thiadiazin-3-yl or 1,4-dihydro-3H-benzo[c][1,2,6]thiadiazin-3-yl. In particular, the heterocyclic ring is a 5 to 10 membered ring and may be selected from, 1-dioxido-1,2,5-thiadiazolidin-2-yl, 1,1-dioxido-1,2,6-thiadiazinan-2-yl, 2,2-dioxidobenzo[c][1,2,5]thiadiazol-1(3H)-yl, 1,4-dihydro-3H-pyrido[3,4-c][1,2,6]thiadiazin-3-yl and 1,4-dihydro-3H-benzo[c][1,2,6]thiadiazin-3-yl.

The 4 to 10 membered saturated or partially saturated heterocyclic ring (ring A) may be substituted with one or more (e.g. 1, 2, 3 or 4) of $Q^2$-$(R^5)_p$, wherein each $Q^2$-$(R^5)_p$ is the same or different and wherein:
p is 0 or 1;
$Q^2$ represents halogen, cyano, oxo, nitro, —OR', —SR', —NR'R'', —CONR'R'', —NR'COR'', —NR'CONR''R''', —COR', —C(O)OR', —$SO_2$R', —$SO_2$NR'R'', —NR'$SO_2$R'', —NR'$SO_2$NR''R''', —NR'C(O)OR'', optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, C(O)O, —CONR'—, —NR'—, —NR'CO—, —NR'CONR''—, —$SO_2$NR'—, NR'$SO_2$—, —NR'$SO_2$NR''—, —NR'C(O)O—, —NR'C(O)OR'', optionally substituted $C_1$-$C_6$ alkylene, or optionally substituted —$C_2$-$C_6$ alkenylene;

R', R'' and R''' each independently represent hydrogen, optionally substituted $C_1$-$C_6$ alkyl or optionally substituted $C_1$-$C_6$ alkylene.

When p is 1, $R^5$ represents an optionally substituted 3 to 10 membered heterocyclyl, cycloalkyl, heteroaryl or aryl ring (when p is 0, $Q^2$ is present and $R^5$ is absent).

If substituted with $Q^2$-$(R^5)_p$, the heterocyclic ring is preferably substituted with one or two, more preferably with one, of $Q^2$-$(R^5)_p$ which may be the same or different. In one embodiment, when the heterocyclic ring is monocyclic, the ring is not substituted with $Q^2$-$(R^5)$. In another embodiment, when the heterocyclic ring is bicyclic, the ring is either not substituted with $Q^2$-$(R^5)_p$ or is substituted with only one $Q^2$-$(R^5)$. Preferably p is 1, $Q^2$ is a covalent bond and $R^5$ is a 5 or 6 membered heterocyclyl, cycloalkyl, heteroaryl or aryl ring, e.g. phenyl, pyrazole or morpholinyl.

Substitution with one or more $Q^2$-$(R^5)_p$ is in addition to the -L-X-substitution at the terminal nitrogen of the sulphamide, e.g. when L is a covalent bond and X is $C_1$-$C_6$ alkyl, and the dioxo substitution at the sulphur of the sulphamide. In some instances, ring A will be substituted only with the dioxo substitution at the sulphur of the sulphamide, i.e. when L is a covalent bond, X is hydrogen and ring A is not substituted with $Q^2$-$(R^5)$.

In all cases described herein, $R^5$ may be substituted with one or more (e.g. one, two or three) substituents selected from halogen, cyano, oxo, nitro —$OR^d$, —$SR^d$, —$NR^dR^e$, —$CONR^dR^e$, —$NR^dCOR^e$, —$NR^dCONR^eR^f$, —$COR^d$, —$C(O)OR^d$, —$SO_2R^d$, —$SO_2NR^eR^e$, —$NR^dSO_2R^e$, —$NR^dSO_2NR^eR^f$, —$NR^dC(O)OR^e$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^5$-$R^d$, -$Q^5$-$NR^dCONR^eR^f$, -$Q^5$-$NR^dR^e$, -$Q^5$-$COR^d$, -$Q^5$-$NR^dCOR^e$, -$Q^5$-$NR^dC(O)OR^e$, -$Q^5$-$SO_2R^d$, $Q^5$-$CONR^dR^e$, -$Q^5$-$CO_2R^d$, -$Q^5$-$SO_2NR^dR^e$, -$Q^5$-$NR^dSO_2R^e$ and -$Q^5$-$NR^dSO_2NR^eR^f$, wherein the alkyl, alkoxy, alkenyl or alkynyl are optionally substituted with one or more substituents selected from halogen, hydroxyl, thiol, cyano, amino, nitro and $SF_5$.

$Q^5$ represents a covalent bond, an oxygen atom, a sulphur atom, —SO—, —$SO_2$—, —CO—, optionally substituted $C_1$-$C_6$ alkylene or optionally substituted $C_2$-$C_6$ alkenylene; and $R^d$, $R^e$ and $R^f$ each independently represent hydrogen, $C_1$-$C_6$ alkyl, optionally substituted heterocyclyl, optionally substituted heteroaryl, optionally substituted aryl, or an optionally substituted cycloalkyl, wherein the alkyl is optionally substituted with one or more substituents selected from halogen, hydroxyl, thiol, cyano, amino, nitro and $SF_5$ and wherein the heterocyclyl, cycloalkyl, heteroaryl or aryl are optionally substituted in accordance with the definitions provided herein.

For compounds of formula (IA), the 3 to 10 membered heterocyclyl, cycloalkyl, heteroaryl or aryl ring of $R^5$ may be unsubstituted or substituted with $C_1$-$C_6$ alkyl or $C_1$-$C_6$ alkoxy, in particular, $C_1$-$C_3$ alkyl or $C_1$-$C_3$ alkoxy, wherein the alkyl or alkoxy may be optionally substituted with one or more substituents selected from halogen, hydroxyl, thiol, cyano, amino, nitro and $SF_5$.

In one embodiment, the present invention relates to compounds of formula (IA) wherein X is a 3 to 14 membered ring optionally substituted with one or more (e.g. one, two, three or four) -Q$^1$-(R$^4$)$_n$, and L, m, R$^1$ and ring A are as defined herein.

In another embodiment, the present invention relates to compounds of formula (IA) wherein L is a bond or optionally substituted C$_1$-C$_3$ alkylene, X is a 3 to 14 membered ring optionally substituted with one or two -Q$^1$-(R$^4$)$_n$, and m, R$^1$ and ring A are as defined herein.

In a further embodiment, the present invention relates to compounds of formula (IA) wherein L is a bond or optionally substituted C$_1$-C$_3$ alkylene, X is a 3 to 14 membered ring In another aspect of the invention, when R$^3$ together with X forms a heterocyclic ring, the compound may be represented by formula (IB):

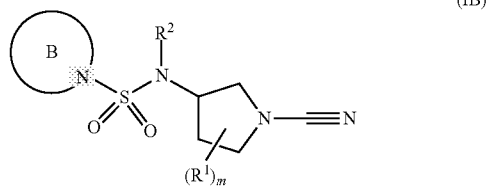

(IB)

or a pharmaceutically acceptable salt thereof, wherein:
R$^2$ represents hydrogen, optionally substituted C$_1$-C$_6$ alkyl or an optionally substituted 3 to 6 membered ring; and ring B is an optionally substituted 4 to 10 membered heterocyclyl or heteroaryl ring.

R$^2$ may represent hydrogen or optionally substituted C$_1$-C$_3$ alkyl. In particular, R$^2$ is hydrogen.

The heterocyclic ring (ring B) may be a 4 to 10 membered heterocyclyl or heteroaryl ring which may be unsubstituted or substituted with one or more Q$^3$-(R$^6$)$_q$, wherein each Q$^3$-(R$^6$)$_q$ is the same or different and wherein:
q is 0 or 1;
Q$^3$ represents halogen, cyano, oxo, nitro, —OR', —SR', —NR'R", —CONR'R", —NR'COR", —NR'CONR"R"', —COR', —C(O)OR', —SO$_2$R', —SO$_2$NR'R", —NR'SO$_2$R", —NR'SO$_2$NR"R"', —NR'C(O)OR", optionally substituted —C$_1$-C$_6$ alkyl, optionally substituted —C$_1$-C$_6$ alkoxy, optionally substituted —C$_2$-C$_6$ alkenyl, optionally substituted —C$_2$-C$_6$ alkynyl, a covalent bond, an oxygen atom, a sulphur atom, —SO—, —SO$_2$—, —CO—, C(O)O, —CONR'—, —NR'—, —NR'CO—, —NR'CONR"—, —SO$_2$NR'—, NR'SO$_2$—, —NR'SO$_2$NR"—, —NR'C(O)O—, —NR'C(O)OR", optionally substituted C$_1$-C$_6$ alkylene, or optionally substituted —C$_2$-C$_6$ alkenylene;
R', R" and R"' each independently represent hydrogen, optionally substituted C$_1$-C$_6$ alkyl, optionally substituted C$_1$-C$_6$ alkoxy or optionally substituted C$_1$-C$_6$ alkylene.

When q is 1, R$^6$ represents an optionally substituted 3 to 10 membered heterocyclyl, cycloalkyl, heteroaryl or aryl ring (when q is 0, Q$^3$ is present and R$^6$ is absent).

Preferably, ring B is an optionally substituted 4 to 10 membered monocyclic or bicyclic heterocyclyl or heteroaryl ring. The heterocyclyl and heteroaryl ring may be defined according to the definition of heterocyclyl and heteroaryl found herein.

In particular, ring B is a 5 to 10 membered monocyclic or bicyclic heterocyclic or heteroaryl ring. Ring B may be a 5 or 6 membered heterocyclyl or heteroaryl ring, and in particular, a heterocyclyl ring. Alternatively, ring B may be a 9 or 10 membered heterocyclyl or heteroaryl ring. More particularly, ring B is selected from piperidinyl, piperazinyl, indolinyl, benzopiperidinyl, dihydroisoquinolinyl and dihydropyrazolo[1,5-a]pyrimidinyl.

Preferably, ring B is either unsubstituted or substituted with one, two, three or four of Q$^3$-(R$^6$)$_q$. In particular, ring B is either unsubstituted or substituted with one or two of Q$^3$-(R$^6$)$_q$. Each occurrence of Q$^3$-(R$^6$)$_q$ may be the same or different. More particularly, ring B is either unsubstituted or substituted with one of Q$^3$-(R$^6$)$_q$. Q$^3$, R$^6$ and q are as defined herein.

Preferably, when q is 1, Q$^3$ is a bond or C$_1$-C$_6$ alkylene, for example C$_1$-C$_3$ alkylene, and R$^6$ is an optionally substituted 3 to 10 membered ring. In particular, R$^6$ is a 5 or 6 membered aryl or heteroaryl. R$^6$ may be a 6 membered aryl or heteroaryl ring. More particularly, R$^6$ is phenyl.

Preferably, when q is 0, Q$^3$ is optionally substituted C$_1$-C$_6$ alkyl or optionally substituted C$_1$-C$_6$ alkoxy. In particular, Q$^3$ is C$_1$-C$_3$ alkyl, C$_1$-C$_3$ alkoxy wherein the alkyl or alkoxy is optionally substituted with one or more (e.g. one, two or three) fluorine. More particularly, Q$^3$ is methoxy.

In all cases described herein, R$^6$ may be substituted with one or more (e.g. one, two or three) substituents selected from halogen, cyano, oxo, nitro —OR$^g$, —SR$^g$, —NR$^g$R$^h$, —CONR$^g$R$^h$, —NR$^g$COR$^h$, —NR$^g$CONR$^h$R$^i$, —COR$^g$, —C(O)OR$^g$, —SO$_2$R$^g$, —SO$_2$NR$^g$R$^h$, —NR$^g$SO$_2$R$^h$, —NR$^g$SO$_2$NR$^h$R$^i$, —NR$^g$C(O)OR$^h$, optionally substituted —C$_1$-C$_6$ alkyl, optionally substituted —C$_1$-C$_6$ alkoxy, optionally substituted —C$_2$-C$_6$ alkenyl, optionally substituted —C$_2$-C$_6$ alkynyl, -Q$^6$-R$^g$, -Q$^6$-NR$^g$CONR$^h$R$^i$, -Q$^6$-NR$^g$R$^h$, -Q$^6$-COR$^g$, -Q$^6$-NR$^g$COR$^h$, -Q$^6$-NR$^g$C(O)OR$^h$, -Q$^6$-SO$_2$R$^g$, Q$^6$-CONR$^g$R$^h$, -Q$^6$-CO$_2$R$^g$, -Q$^6$-SO$_2$NR$^g$R$^h$, -Q$^6$-NR$^g$SO$_2$R$^h$ and -Q$^6$-NR$^g$SO$_2$NR$^h$R$^i$, wherein the alkyl, alkoxy, alkenyl or alkynyl are optionally substituted with one or more substituents selected from halogen, hydroxyl, thiol, cyano, amino, nitro and SF$_5$.

Q$^6$ represents a covalent bond, an oxygen atom, a sulphur atom, —SO—, —SO$_2$—, —CO—, optionally substituted C$_1$-C$_6$ alkylene or optionally substituted C$_2$-C$_6$ alkenylene; and R$^g$, R$^h$ and R$^i$ each independently represent hydrogen, C$_1$-C$_6$ alkyl, optionally substituted heterocyclyl, optionally substituted heteroaryl, optionally substituted aryl, or an optionally substituted cycloalkyl, wherein the alkyl is optionally substituted with one or more substituents selected from halogen, hydroxyl, thiol, cyano, amino, nitro and SF$_5$ and wherein the heterocyclyl, cycloalkyl, heteroaryl or aryl are optionally substituted in accordance with the definitions provided herein.

For compounds of formula (IB), the 3 to 10 membered heterocyclyl, cycloalkyl, heteroaryl or aryl ring of R$^6$ may be unsubstituted or substituted with C$_1$-C$_6$ alkyl or C$_1$-C$_6$ alkoxy, in particular, C$_1$-C$_3$ alkyl or C$_1$-C$_3$ alkoxy, wherein the alkyl or alkoxy may be optionally substituted with one or more substituents selected from halogen, hydroxyl, thiol, cyano, amino, nitro and SF$_5$. In particular, R$^6$ is unsubstituted.

In one embodiment, the present invention relates to compounds of formula (IB) wherein R$^2$ is hydrogen or optionally substituted C$_1$-C$_3$ alkyl and m, R$^1$ and ring B are as defined herein.

In another embodiment, the present invention relates to compounds of formula (IB) wherein R$^2$ is hydrogen or optionally substituted $C_1$-$C_6$ alkyl, ring B is a 4 to 10 membered monocyclic or bicyclic heterocyclic ring, and m and $R^1$ are as defined herein.

In another embodiment, the present invention relates to compounds of formula (IB) wherein $R^2$ is hydrogen or optionally substituted $C_1$-$C_3$ alkyl, ring B is a 5 to 10 membered monocylic or bicyclic heterocyclyl or heteroaryl ring which is unsubstituted or substituted with one or two, preferably one, of $Q^3$-$(R^6)_q$ which can be the same or different, wherein q is 0 or 1, $Q^3$ is a covalent bond, an oxygen atom, optionally substituted $C_1$-$C_6$ alkylene, optionally substituted $C_2$-$C_6$ alkenylene, optionally substituted $C_1$-$C_6$ alkyl, optionally substituted $C_1$-$C_6$ alkoxy, $R^6$ is an optionally substituted 5 or 6 membered aryl or heteroaryl ring, and m and $R^1$ are as defined herein.

In yet another embodiment, the present invention relates to compounds of formula (IB) wherein $R^2$ is hydrogen or optionally substituted $C_1$-$C_3$ alkyl, ring B is a 5 to 10 membered monocylic or bicyclic heterocyclyl or heteroaryl ring which is unsubstituted or substituted with one of $Q^3$-$(R^6)_p$, wherein q is 0 or 1, $Q^3$ is a covalent bond, optionally substituted $C_1$-$C_3$ alkyl or optionally substituted $C_1$-$C_3$ alkoxy, $R^6$ is an optionally substituted 5 or 6 membered aryl or heteroaryl ring, and m and $R^1$ are as defined herein.

In a further aspect of the invention, when X represents an optionally substituted ring, the compound may be represented by formula (IC):

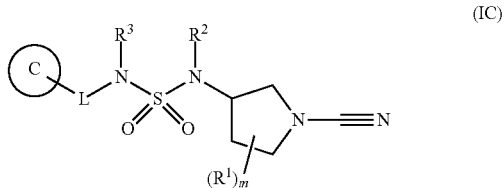

(IC)

or a pharmaceutically acceptable salt thereof, wherein:
$R^2$ and $R^3$ each independently represent hydrogen, optionally substituted $C_1$-$C_6$ alkyl or an optionally substituted 3 to 10 membered ring;
L is a covalent bond or an optionally substituted $C_1$-$C_6$ alkylene or optionally substituted —$C_2$-$C_6$ alkenylene linker;
ring C is an optionally substituted 3 to 14 membered ring.

$R^2$ and $R^3$ each independently represent hydrogen, optionally substituted $C_1$-$C_6$ alkyl or an optionally substituted 3 to 10 membered ring. Preferably, $R^2$ and $R^3$ each independently represent hydrogen or optionally substituted $C_1$-$C_3$ alkyl. In particular, $R^2$ and $R^3$ each independently represent hydrogen or methyl. More particularly, $R^2$ and $R^3$ are both hydrogen or are both methyl.

Ring C represents a 3 to 14 membered ring which may be unsubstituted or substituted with one or more $Q^1$-$(R^4)_n$, wherein each $Q^1$-$(R^4)$R is the same or different and wherein: n is 0 or 1;
$Q^1$ represents halogen, cyano, oxo, nitro, —OR', —SR', —NR'R", —CONR'R", —NR'COR", —NR'CONR"R'", —COR', —C(O)OR', —SO$_2$R', —SO$_2$NR'R", —NR'SO$_2$R", NR'SO$_2$NR"R'", —NR'C(O)OR", optionally substituted —$C_1$-$C_6$ alkyl, optionally substituted —$C_1$-$C_6$ alkoxy, optionally substituted —$C_2$-$C_6$ alkenyl, optionally substituted alkynyl, a covalent bond, an oxygen atom, a sulphur atom, —SO—, —SO$_2$—, —CO—, C(O)O, —CONR'—, —NR'—, —NR'CO—, —NR'CONR"—, —SO$_2$NR'—, NR'SO$_2$—, —NR'SO$_2$NR"—, —NR'C(O)O—, —NR'C(O)OR", optionally substituted $C_1$-$C_6$ alkylene, or optionally substituted —$C_2$-$C_6$ alkenylene;
R', R" and R'" each independently represent hydrogen, optionally substituted $C_1$-$C_6$ alkyl, optionally substituted $C_1$-$C_6$ alkoxy or optionally substituted $C_1$-$C_6$ alkylene.

When n is 1, $R^4$ represents an optionally substituted 3 to 10 membered heterocyclyl, cycloalkyl, heteroaryl or aryl ring (when n is 1, $Q^4$ is present and $R^4$ is absent).

Preferably, ring C is a 3 to 14 membered ring selected from an optionally substituted cycloalkyl, an optionally substituted heteroalkyl, an optionally substituted aryl or an optionally substituted heteroaryl. The cycloalkyl, heteroalkyl, aryl and heteroaryl may be defined according to the definitions of alkyl, heteroalkyl, aryl and heteroaryl found herein. The 3 to 14 membered ring may be monocyclic, bicyclic or tricyclic.

In particular, ring C is a 3 to 14 membered aryl or heteroaryl ring. Ring C may be a 5 to 10 membered ring, for example, a 5 or 6 membered aryl or heteroaryl ring. Alternatively, ring C may be a 9 or 10 membered aryl or heteroaryl ring. More particularly, ring C is selected from phenyl or benzimidazole.

Preferably, ring C is either unsubstituted or substituted with one, two, three or four of $Q^1$-$(R^4)_n$. In particular, ring C is either unsubstituted or substituted with one or two of $Q^1$-$(R^4)_n$. Each occurrence of $Q^1$-$(R^4)_n$ may be the same or different. More particularly, ring C is either unsubstituted or substituted with one of $Q^1$-$(R^4)_n$. $Q^1$, $R^4$ and n are as defined herein.

Preferably, when n is 1, $Q^1$ is a bond or $C_1$-$C_6$ alkylene, for example $C_1$-$C_3$ alkylene, and $R^4$ is an optionally substituted 3 to 10 membered ring. In particular, $R^4$ is a 5 or 6 membered aryl or heteroaryl. More particularly, $R^4$ is phenyl.

Preferably, when n is 0, $Q^1$ is halogen, oxo, optionally substituted $C_1$-$C_6$ alkyl or optionally substituted $C_1$-$C_6$ alkoxy. In particular, $Q^1$ is $C_1$-$C_3$ alkyl or $C_1$-$C_3$ alkoxy wherein the alkyl or alkoxy is optionally substituted with one or more halogen, hydroxyl, thiol, cyano, amino, nitro and SF$_5$, in particular fluorine. More particularly, $Q^1$ is CF$_3$.

In all cases described herein, $R^4$ may be substituted with one or more (e.g. one, two or three) substituents selected from halogen, cyano, oxo, nitro —OR$^a$, —SR$^a$, —NR$^a$R$^b$, —CONR$^a$R$^b$, —NR$^a$COR$^b$, —NR$^a$CONR$^b$R$^c$, —COR$^a$, —C(O)OR$^a$, —SO$_2$R$^a$, —SO$_2$NR$^a$R$^b$, —NR$^a$SO$_2$R$^b$, NR$^a$SO$_2$NR$^b$R$^c$, —NR$^a$C(O)OR$^b$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -Q$^4$-R$^a$, -Q$^4$-NR$^a$CONR$^b$R$^c$, -Q$^4$-NR$^a$R$^b$, -Q$^4$-COR$^a$, -Q$^4$-NR$^a$COR$^b$, -Q$^4$-NR$^a$C(O)OR$^b$, -Q$^4$-SO$_2$R$^a$, -Q$^4$-CONR$^a$R$^b$, -Q$^4$-CO$_2$R$^a$, -Q$^4$-SO$_2$NR$^a$R$^b$, -Q$^4$-NR$^a$SO$_2$R$^b$ and -Q$^4$-NR$^a$SO$_2$NR$^b$R$^c$, wherein the alkyl, alkoxy, alkenyl or alkynyl are optionally substituted with one or more substituents selected from halogen, hydroxyl, thiol, cyano, amino, nitro and SF$_5$.

$Q^4$ represents a covalent bond, an oxygen atom, a sulphur atom, —SO—, —SO$_2$—, —CO—, optionally substituted $C_1$-$C_6$ alkylene or optionally substituted $C_2$-$C_6$ alkenylene; and
$R^a$, $R^b$ and $R^c$ each independently represent hydrogen, $C_1$-$C_6$ alkyl, optionally substituted heterocyclyl, optionally substituted heteroaryl, optionally substituted aryl, or an optionally substituted cycloalkyl, wherein the alkyl is optionally substituted with one or more substituents selected from halogen, hydroxyl, thiol, cyano, amino, nitro and SF$_5$ and wherein the heterocyclyl, cycloalkyl, heteroaryl or aryl are optionally substituted in accordance with the definitions provided herein.

For compounds of formula (IC), the 3 to 10 membered heterocyclyl, cycloalkyl, heteroaryl or aryl ring of $R^4$ may be unsubstituted or substituted with $C_1$-$C_6$ alkyl or $C_1$-$C_6$ alkoxy, in particular, $C_1$-$C_3$ alkyl or $C_1$-$C_3$ alkoxy, wherein the alkyl or alkoxy may be optionally substituted with one or more substituents selected from halogen, hydroxyl, thiol, cyano, amino, nitro and $SF_5$. In particular, $R^4$ is unsubstituted.

In one embodiment, the present invention relates to compounds of formula (IC), wherein $R^2$ and $R^3$ each independently represent hydrogen or optionally substituted $C_1$-$C_3$ alkyl and m, $R^1$, L and ring C are as defined herein. In particular, each $R^1$ is independently selected from fluorine, cyano, hydroxyl, amino, optionally substituted $C_1$-$C_6$ alkyl and optionally substituted $C_1$-$C_6$ alkoxy.

In another embodiment, the present invention relates to compounds of formula (IC), wherein $R^2$ and $R^3$ each independently represent hydrogen, optionally substituted $C_1$-$C_6$ alkyl or an optionally substituted ring, L is a covalent bond or optionally substituted $C_1$-$C_3$ alkyl and m, $R^1$ and ring C are as defined herein.

In another embodiment the present invention relates to compounds of formula (IC), wherein $R^2$ and $R^3$ each independently represent hydrogen, optionally substituted $C_1$-$C_6$ alkyl or an optionally substituted ring, ring C is a 3 to 14 membered ring selected from an optionally substituted cycloalkyl, an optionally substituted heteroalkyl, an optionally substituted aryl or an optionally substituted heteroaryl, and L, m and $R^1$ are as defined herein.

In another embodiment, the present invention relates to compounds of formula (IC), wherein $R^2$ and $R^3$ each independently represent hydrogen or optionally substituted $C_1$-$C_3$ alkyl, and L is a covalent bond or optionally substituted $C_1$-$C_3$ alkyl, ring C is a 3 to 14 membered ring selected from an optionally substituted cycloalkyl, an optionally substituted heteroalkyl, an optionally substituted aryl or an optionally substituted heteroaryl, and m and $R^1$ are as defined herein.

In yet another embodiment, the present invention relates to compounds of formula (IC), wherein $R^2$ and $R^3$ each independently represent hydrogen or optionally substituted $C_1$-$C_3$ alkyl, L is a covalent bond or optionally substituted $C_1$-$C_3$ alkyl and ring C is a 5 to 10 membered aryl or heteroaryl ring wherein the aryl or heteroaryl ring is either unsubstituted or substituted with one or two, preferably one, of $Q^1$-$(R^4)_n$ which are the same or different, wherein n is 0 or 1, $Q^1$ is a covalent bond, an oxygen atom, optionally substituted $C_1$-$C_6$ alkylene, optionally substituted $C_2$-$C_6$ alkenylene, optionally substituted $C_1$-$C_6$ alkyl, optionally substituted $C_1$-$C_6$ alkoxy, $R^4$ is an optionally substituted 5 or 6 membered aryl or heteroaryl ring, and m and $R^1$ are as defined herein.

In yet another embodiment, the present invention relates to compounds of formula (IC), wherein $R^2$ and $R^3$ each independently represent hydrogen or optionally substituted $C_1$-$C_3$ alkyl, L is a covalent bond, ring C is a 5 to 10 membered aryl or heteroaryl ring wherein the aryl or heteroaryl ring is either unsubstituted or substituted with one of $Q^1$-$(R^4)_n$, wherein n is 0 or 1, $Q^1$ is a covalent bond, optionally substituted $C_1$-$C_3$ alkylene or $C_1$-$C_3$ alkyl optionally substituted with one or more fluorine, $R^4$ is an optionally substituted 5 membered aryl or heteroaryl ring, and m and $R^1$ are as defined herein.

Examples of novel compounds of formula (I) include:
(S)-3-(5-(3-(isoxazol-5-yl)phenyl)-1,1-dioxido-1,2,5-thiadiazolidin-2-yl)pyrrolidine-1-carbonitrile
(R)-3-(5-(4-methyl-3-oxo-3,4-dihydro-2H-benzo[b][1,4]oxazin-7-yl)-1,1-dioxido-1,2,5-thiadiazolidin-2-yl)pyrrolidine-1-carbonitrile
(R)-3-(1,1-dioxido-5-(3-oxo-3,4-dihydro-2H-benzo[b][1,4]oxazin-7-yl)-1,2,5-thiadiazolidin-2-yl)pyrrolidine-1-carbonitrile
(R)-3-(5-(4-methyl-3-oxo-3,4-dihydro-2H-benzo[b][1,4]oxazin-6-yl)-1,1-dioxido-1,2,5-thiadiazolidin-2-yl)pyrrolidine-1-carbonitrile
(R)-3-(1,1-dioxido-5-(3-oxo-3,4-dihydro-2H-benzo[b][1,4]oxazin-6-yl)-1,2,5-thiadiazolidin-2-yl)pyrrolidine-1-carbonitrile
(R)-3-(5-(4-(2-hydroxyethyl)-3-oxo-3,4-dihydro-2H-benzo[b][1,4]oxazin-6-yl)-1,1-dioxido-1,2,5-thiadiazolidin-2-yl)pyrrolidine-1-carbonitrile
3-(5-(4-methyl-3-oxo-3,4-dihydro-2H-benzo[b][1,4]oxazin-6-yl)-1,1-dioxido-1,2,5-thiadiazolidin-2-yl)pyrrolidine-1-carbonitrile
(R)-3-(5-(4-methoxy-3-morpholinophenyl)-1,1-dioxido-1,2,5-thiadiazolidin-2-yl)pyrrolidine-1-carbonitrile
(3R)-3-(1,1-dioxido-5-(1-(pyridin-2-yl)pyrrolidin-3-yl)-1,2,5-thiadiazolidin-2-yl)pyrrolidine-1-carbonitrile
(R)-3-(5-(2'-methoxy-[1,1'-biphenyl]-3-yl)-1,1-dioxido-1,2,5-thiadiazolidin-2-yl)pyrrolidine-1-carbonitrile
(R)-3-(5-([1,1'-biphenyl]-4-yl)-1,1-dioxido-1,2,5-thiadiazolidin-2-yl)pyrrolidine-1-carbonitrile
(R)-3-(6-([1,1'-biphenyl]-4-yl)-1,1-dioxido-1,2,6-thiadiazinan-2-yl)pyrrolidine-1-carbonitrile
(R)-3-(5-([1,1'-biphenyl]-3-yl)-1,1-dioxido-1,2,5-thiadiazolidin-2-yl)pyrrolidine-1-carbonitrile
(R)-3-(6-([1,1'-biphenyl]-3-yl)-1,1-dioxido-1,2,6-thiadiazinan-2-yl)pyrrolidine-1-carbonitrile
(R)-3-(5-(4-methoxy-[1,1'-biphenyl]-3-yl)-1,1-dioxido-1,2,5-thiadiazolidin-2-yl)pyrrolidine-1-carbonitrile
(R)-3-(5-(3'-methoxy-[1,1'-biphenyl]-3-yl)-1,1-dioxido-1,2,5-thiadiazolidin-2-yl)pyrrolidine-1-carbonitrile
(R)-3-(5-(2'-methoxy-[1,1'-biphenyl]-4-yl)-1,1-dioxido-1,2,5-thiadiazolidin-2-yl)pyrrolidine-1-carbonitrile
(R)-3-(1,1-dioxido-5-(4-(pyridin-4-yl)phenyl)-1,2,5-thiadiazolidin-2-yl)pyrrolidine-1-carbonitrile
(R)-3-(1,1-dioxido-5-(3-(pyridin-4-yl)phenyl)-1,2,5-thiadiazolidin-2-yl)pyrrolidine-1-carbonitrile
(R)-3-(5-(3-(1-methyl-1H-pyrazol-4-yl)phenyl)-1,1-dioxido-1,2,5-thiadiazolidin-2-yl)pyrrolidine-1-carbonitrile
(R)-3-(6-(3-(1-methyl-1H-pyrazol-4-yl)phenyl)-1,1-dioxido-1,2,6-thiadiazinan-2-yl)pyrrolidine-1-carbonitrile
(R)-3-(5-(4-morpholinophenyl)-1,1-dioxido-1,2,5-thiadiazolidin-2-yl)pyrrolidine-1-carbonitrile
(R)-3-(5-(3-chloro-4-morpholinophenyl)-1,1-dioxido-1,2,5-thiadiazolidin-2-yl)pyrrolidine-1-carbonitrile
(R)-3-(5-(3-morpholinophenyl)-1,1-dioxido-1,2,5-thiadiazolidin-2-yl)pyrrolidine-1-carbonitrile
(R)-3-(6-(3-morpholinophenyl)-1,1-dioxido-1,2,6-thiadiazinan-2-yl)pyrrolidine-1-carbonitrile
(R)-3-(1,1-dioxido-5-(3-phenylisoxazol-5-yl)-1,2,5-thiadiazolidin-2-yl)pyrrolidine-1-carbonitrile
(R)-3-(1,1-dioxido-6-(3-phenylisoxazol-5-yl)-1,2,6-thiadiazinan-2-yl)pyrrolidine-1-carbonitrile
(R)-3-(1,1-dioxido-5-(3-phenyl-1H-pyrazol-5-yl)-1,2,5-thiadiazolidin-2-yl)pyrrolidine-1-carbonitrile
(R)-3-(1,1-dioxido-6-(3-phenyl-1H-pyrazol-5-yl)-1,2,6-thiadiazinan-2-yl)pyrrolidine-1-carbonitrile
(R)—N-(1-cyanopyrrolidin-3-yl)-2-phenyl-6,7-dihydropyrazolo[1,5-a]pyrimidine-4(5H)-sulfonamide (S)-3-(1,1-dioxido-5-phenyl-1,2,5-thiadiazolidin-2-yl)pyrrolidine-1-carbonitrile
(S)-3-(1,1-dioxido-5-(4-(pyridin-4-yl)phenyl)-1,2,5-thiadiazolidin-2-yl)pyrrolidine-1-carbonitrile
(S)-3-(1,1-dioxido-5-(3-(pyridin-4-yl)phenyl)-1,2,5-thiadiazolidin-2-yl)pyrrolidine-1-carbonitrile
(S)-3-(5-([1,1'-biphenyl]-4-yl)-1,1-dioxido-1,2,5-thiadiazolidin-2-yl)pyrrolidine-1-carbonitrile
(S)-3-(5-([1,1'-biphenyl]-3-yl)-1,1-dioxido-1,2,5-thiadiazolidin-2-yl)pyrrolidine-1-carbonitrile
(S)-3-(1,1-dioxido-5-(6-phenylpyridin-2-yl)-1,2,5-thiadiazolidin-2-yl)pyrrolidine-1-carbonitrile
3-(1,1-dioxido-5-phenyl-1,2,5-thiadiazolidin-2-yl)pyrrolidine-1-carbonitrile
3-(1,1-dioxido-6-phenyl-1,2,6-thiadiazinan-2-yl)pyrrolidine-1-carbonitrile
(3R,4S)-3-(5-([1,1'-biphenyl]-4-yl)-1,1-dioxido-1,2,5-thiadiazolidin-2-yl)-4-methylpyrrolidine-1-carbonitrile
(3S,4R)-3-methyl-4-(5-(3-(4-methylpiperazin-1-yl)phenyl)-1,1-dioxido-1,2,5-thiadiazolidin-2-yl)pyrrolidine-1-carbonitrile
(3S,4R)-3-methyl-4-(5-(3-morpholinophenyl)-1,1-dioxido-1,2,5-thiadiazolidin-2-yl)pyrrolidine-1-carbonitrile
(R)-3-(5-(6-methoxy-[1,1'-biphenyl]-3-yl)-1,1-dioxido-1,2,5-thiadiazolidin-2-yl)pyrrolidine-1-carbonitrile
(R)-3-(5-(2-methoxy-[1,1'-biphenyl]-4-yl)-1,1-dioxido-1,2,5-thiadiazolidin-2-yl)pyrrolidine-1-carbonitrile
(R)-3-(1,1-dioxido-5-(2-(trifluoromethyl)-1H-benzo[d]imidazol-5-yl)-1,2,5-thiadiazolidin-2-yl)pyrrolidine-1-carbonitrile
(R)-3-(1,1-dioxido-6-(2-(trifluoromethyl)-1H-benzo[d]imidazol-6-yl)-1,2,6-thiadiazinan-2-yl)pyrrolidine-1-carbonitrile
(R)-3-(1,1-dioxido-6-(2-(trifluoromethyl)-1H-benzo[d]imidazol-6-yl)-1,2,6-thiadiazinan-2-yl)pyrrolidine-1-carbonitrile
(S)-3-(1,1-dioxido-5-(3-(pyridin-2-yl)phenyl)-1,2,5-thiadiazolidin-2-yl)pyrrolidine-1-carbonitrile
(S)-3-(1,1-dioxido-5-(3-(pyridin-3-yl)phenyl)-1,2,5-thiadiazolidin-2-yl)pyrrolidine-1-carbonitrile
(R)-3-(5-(9-methyl-9H-carbazol-3-yl)-1,1-dioxido-1,2,5-thiadiazolidin-2-yl)pyrrolidine-1-carbonitrile
(R)-3-(5-(2-morpholinopyridin-4-yl)-1,1-dioxido-1,2,5-thiadiazolidin-2-yl)pyrrolidine-1-carbonitrile
(R)-3-(5-(4-morpholinopyrimidin-2-yl)-1,1-dioxido-1,2,5-thiadiazolidin-2-yl)pyrrolidine-1-carbonitrile
(R)-3-(5-(2-(4-methylpiperazin-1-yl)pyridin-4-yl)-1,1-dioxido-1,2,5-thiadiazolidin-2-yl)pyrrolidine-1-carbonitrile
(R)-3-(5-(3-((R)-3-methoxypyrrolidin-1-yl)phenyl)-1,1-dioxido-1,2,5-thiadiazolidin-2-yl)pyrrolidine-1-carbonitrile
(R)-3-(5-(2-((R)-3-methoxypyrrolidin-1-yl)pyridin-4-yl)-1,1-dioxido-1,2,5-thiadiazolidin-2-yl)pyrrolidine-1-carbonitrile
(R)-3-(5-(2-(3-methoxyazetidin-1-yl)pyridin-4-yl)-1,1-dioxido-1,2,5-thiadiazolidin-2-yl)pyrrolidine-1-carbonitrile
(R)-3-(5-(2-(bis(2-methoxyethyl)amino)pyridin-4-yl)-1,1-dioxido-1,2,5-thiadiazolidin-2-yl)pyrrolidine-1-carbonitrile
N-biphenyl-3-yl-N'-(1-cyanopyrrolidin-3-yl)sulfuric diamide
N-biphenyl-4-yl-N'-(1-cyanopyrrolidin-3-yl)sulfuric diamide
N-(1-cyanopyrrolidin-3-yl)-4-phenylpiperidine-1-sulfonamide
N-(1-cyanopyrrolidin-3-yl)-4-phenylpiperazine-1-sulfonamide
N-(1-cyanopyrrolidin-3-yl)indoline-1-sulfonamide
(R)—N-(1-cyanopyrrolidin-3-yl)-3,4-dihydroisoquinoline-2(1H)-sulfonamide
(R)—N-(1-cyanopyrrolidin-3-yl)-5-phenylindoline-1-sulfonamide
(R)—N-(1-cyanopyrrolidin-3-yl)-4-phenylindoline-1-sulfonamide
(R)—N-(1-cyanopyrrolidin-3-yl)-6-methoxy-3,4-dihydroisoquinoline-2(1H)-sulfonamide
(R)-3-(3-methyl-2,2-dioxidobenzo[c][1,2,5]thiadiazol-1(3H)-yl)pyrrolidine-1-carbonitrile
(R)-3-(3-benzyl-2,2-dioxidobenzo[c][1,2,5]thiadiazol-1(3H)-yl)pyrrolidine-1-carbonitrile
(R)-3-(2,2-dioxido-3-(pyridin-3-ylmethyl)benzo[c][1,2,5]thiadiazol-1(3H)-yl)pyrrolidine-1-carbonitrile
(R)-3-(1-benzyl-2,2-dioxido-1,4-dihydro-3H-benzo[c][1,2,6]thiadiazin-3-yl)pyrrolidine-1-carbonitrile
(R)-3-(1-methyl-2,2-dioxido-1,4-dihydro-3H-benzo[c][1,2,6]thiadiazin-3-yl)pyrrolidine-1-carbonitrile
(R)-3-(7-(1-methyl-1H-pyrazol-4-yl)-2,2-dioxido-1,4-dihydro-3H-benzo[c][1,2,6]thiadiazin-3-yl)pyrrolidine-1-carbonitrile
(R)-3-(2,2-dioxido-7-phenyl-1,4-dihydro-3H-benzo[c][1,2,6]thiadiazin-3-yl)pyrrolidine-1-carbonitrile
(R)-3-(1-methyl-2,2-dioxido-7-phenyl-1,4-dihydro-3H-benzo[c][1,2,6]thiadiazin-3-yl)pyrrolidine-1-carbonitrile
(R)-3-(1-methyl-2,2-dioxido-6-phenyl-1,4-dihydro-3H-benzo[c][1,2,6]thiadiazin-3-yl)pyrrolidine-1-carbonitrile
(R)-3-(2,2-dioxido-6-phenyl-1,4-dihydro-3H-benzo[c][1,2,6]thiadiazin-3-yl)pyrrolidine-1-carbonitrile
N-(1-cyanopyrrolidin-3-yl)-N,N'-dimethyl-N'-phenylsulfuric diamide
(R)-3-(8-morpholino-2,2-dioxido-1,4-dihydro-3H-benzo[c][1,2,6]thiadiazin-3-yl)pyrrolidine-1-carbonitrile
(R)-3-(8-morpholino-2,2-dioxido-1,4-dihydro-3H-pyrido[3,4-c][1,2,6]thiadiazin-3-yl)pyrrolidine-1-carbonitrile
or pharmaceutically acceptable salts thereof.

It should be noted that each of the chemical compounds listed above represents a particular and independent aspect of the invention.

According to a further aspect of the invention there is provided a process for the preparation of a compound of formula (I) or a pharmaceutically acceptable salt thereof comprising the steps of reacting an amine of formula (III) with a compound X-L-NH$_2$ and sulphuryl chloride to form a sulphamide:

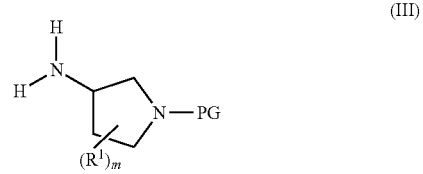

(III)

Wherein R$^1$, X, L and m, are as defined elsewhere and PG is an amine protecting group. The protecting group may be but is not limited to BOC. It is clear to a person skilled in the art to combine or adjust such a protecting chemical group. After coupling of X-L-NH$_2$ to form a sulphamide where R$^2$ and R$^3$ of formula (IV) are both hydrogen, a further alkylation may be undertaken to form compounds where R$^2$ and R$^3$ in formula (IV) are other than hydrogen. The protecting group may be removed to leave the free amine according to formula (V) which can then be treated with cyanogen bromide to form compounds according to formula (I):

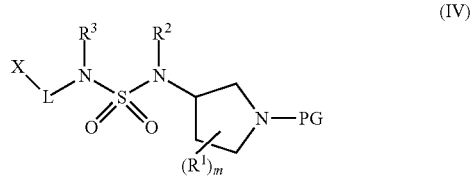

Wherein $R^1$, $R^2$, $R^3$, X, L and m are as defined elsewhere.

According to a further aspect of the invention there is provided a process for the preparation of a compound of formula (I) or a pharmaceutically acceptable salt thereof comprising the steps of reacting an amine of formula (V) with cyanogen bromide to form N—CN compounds:

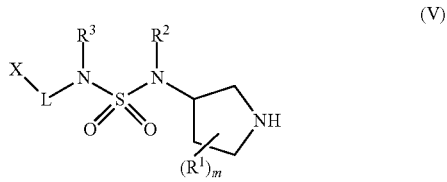

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle.

Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention can be used in the treatment of disorders and diseases related to USP30 inhibition.

Conditions Involving Mitochondrial Dysfunction

The compounds of the invention can be used in the treatment of disorders or diseases having a component relating to mitochondrial dysfunction, particularly disorders or diseases linked to DUB activity. More particularly, disorders or diseases link to USP30 activity.

The compounds described herein may be used in the manufacture of a medicament for the treatment of conditions involving mitochondrial dysfunction.

In a further aspect of the invention there is provided a method of treatment or prevention of a condition involving mitochondrial dysfunction, the method comprising administering a pharmaceutically effective amount of a compound of the invention or a pharmaceutical composition thereof to an individual diagnosed with a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemperal dementia.

In a particular embodiment, the compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

Cancer

Compounds of the invention also have use in the treatment of cancer and more particularly in the treatment of cancer linked to DUB activity, especially USP30 activity.

The compounds as described herein may also be used in the manufacture of a medicament for the treatment of a cancer. In a further aspect of the invention there is provided a method of treatment or prevention of a cancer, the method comprising administering a pharmaceutically effective amount of a compound of the invention or a pharmaceutical composition thereof to an individual suffering from a cancer.

The compounds of the invention also have use in the treatment of cancer linked to mitochondrial dysfunction.

In one embodiment, the compounds of the invention have use in the treatment of cancer where apoptotic pathways are dysregulated and more particularly where proteins of the BCL-2 family are mutated, or over or under expressed.

References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds of the invention or pharmaceutical compositions thereof as described herein may be combined with one or more additional agents when used for the treatment of cancer. The compounds may be combined with an additional anti-tumour therapeutic agent, for example chemotherapeutic drugs or inhibitors of other regulatory proteins. In one embodiment the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

Dosage Forms

For treating a mitochondrial dysfunction disorder, the pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

For treating a CNS disorder, the compounds of the invention must have the ability to pass across the blood-brain barrier. As such, such compounds have the ability to enter the central nervous system of a patient. Alternatively, the pharmaceutical compositions of the present invention can bypass the blood brain barrier through use of compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla. Further dosage forms include those suitable for oral delivery including, but not limited to tablets, dragees, powders, elixirs, syrups, liquid preparations including suspensions, sprays, inhalants, tablets, lozenges, emulsions, solutions, cachets, granules and capsules. For parenteral administration, preparations include sterile aqueous, aqueous-organic, and organic solutions, suspensions and emulsions.

For treating a cancer, the pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration.

These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 μg to about 100 mg per kg body weight of a human and non-human animal and in general may be around 10 μg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by liquid chromatography-mass spectroscopy (LCMS) and $^1$H NMR.

Synthetic Schemes

Abbreviations

BINAP 2,2'-bis(diphenylphosphino)-1,1'-binaphthyl
BOC Tert-butoxycarbonyl
br Broad (NMR signal)
d Doublet (NMR signal)
DBU 1,8-Diazabicyclo[5.4.0]undec-7-ene
DCM Dichloromethane
DMF N,N'-Dimethylformamide
DMSO Dimethylsulphoxide
ES Electrospray
EtOAc Ethyl acetate
h Hour(s)
m Multiplet (NMR signal)
MeCN Acetonitrile
MeOH Methanol
rt Room temperature
s Singlet (NMR signal)
t Triplet (NMR signal)
TEA Triethylamine
TFA Trifluoroacetic acid
THF Tetrahydrofuran
LCMS Methods

| Method A | |
|---|---|
| Column | X-bridge C18, 50*4.6 mm, 3.5 µm or equivalent |
| Mobile Phase | (A) 0.1% Ammonia in Water<br>(B) 0.1% Ammonia in Acetonitrile |
| Flow Rate | 1.0 mL/min |
| Gradient | Time      % B |
| | 0.01      5 |
| | 5.00      90 |
| | 5.80      95 |
| | 7.20      95 |
| | 7.21      5 |
| | 10.00      5 |

| Method B | |
|---|---|
| Column | BEH C18, 50*2.1 mm, 1.7 µm or equivalent |
| Mobile Phase | (A) 5 mM Ammonium Acetate + 0.1% Formic Acid in Water<br>(B) 0.1% Formic Acid in Acetonitrile |
| Flow Rate | 0.45 mL/min |
| Gradient | Time      % B |
| | 0.01      2 |
| | 0.50      2 |
| | 5.00      90 |
| | 6.00      95 |
| | 7.00      95 |
| | 7.01      2 |
| | 8.00      2 |

| Method C | |
|---|---|
| Column | BEH C18, 50*2.1 mm, 1.7 µm or equivalent |
| Mobile Phase | (A) 5 mM Ammonium Acetate + 0.1% Formic Acid in Water<br>(B) 0.1% Formic Acid in Acetonitrile |
| Flow Rate | 0.55 mL/min |
| Gradient | Time      % B |
| | 0.01      5 |
| | 0.40      5 |
| | 0.80      35 |
| | 1.20      55 |
| | 2.50      100 |
| | 3.30      100 |
| | 3.31      5 |
| | 4.00      5 |

General Scheme 1

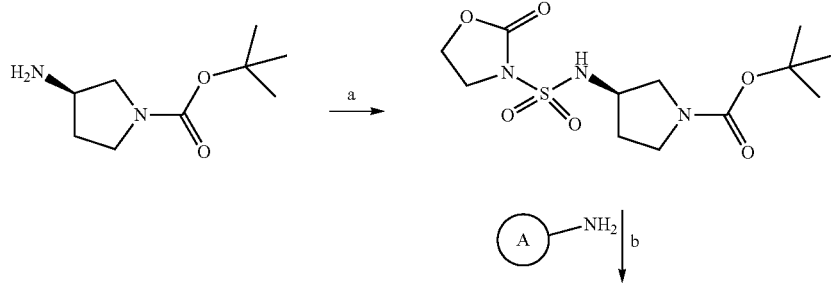

-continued

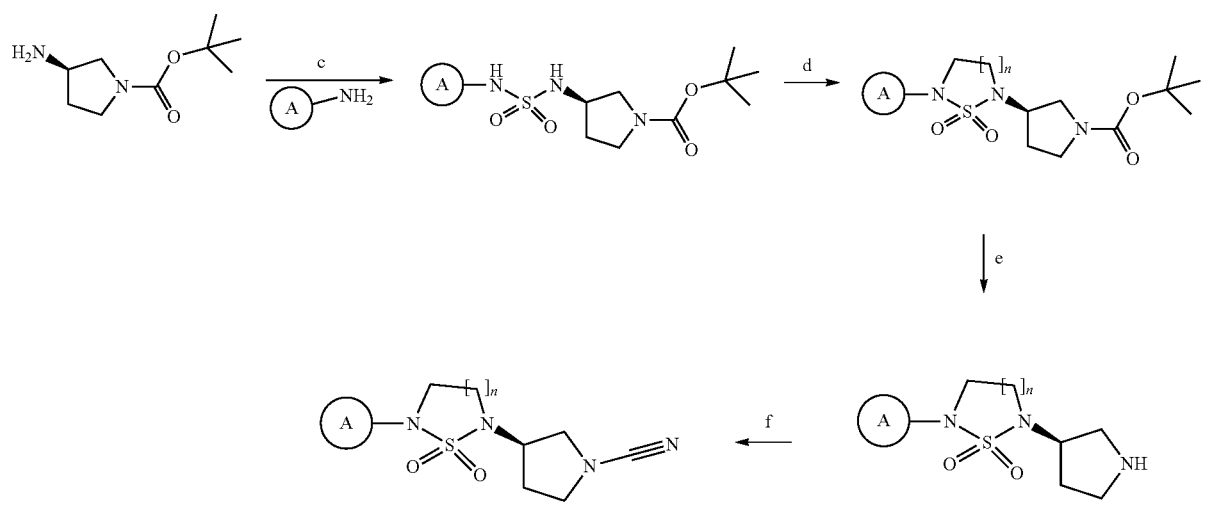

Reagents and conditions: a) chlorosulphonyl isocyanate, 2-bromoethanol, TEA, DCM, 0° C. to rt, 1 h b) TEA, MeCN, 70° C., 15 h c) imidazole, SO₂Cl₂, TEA, DCM, -78° C. to rt, 4 h d) 1,2-dibromoethane (n = 1) or 1,3-dibromopropane (n = 2), K₂CO₃, DMF, 100° C., 3 h e) TFA, DCM, rt, 1-2 h f) cyanogen bromide, K₂CO₃, THF, rt 1-2 h.

General Scheme 2

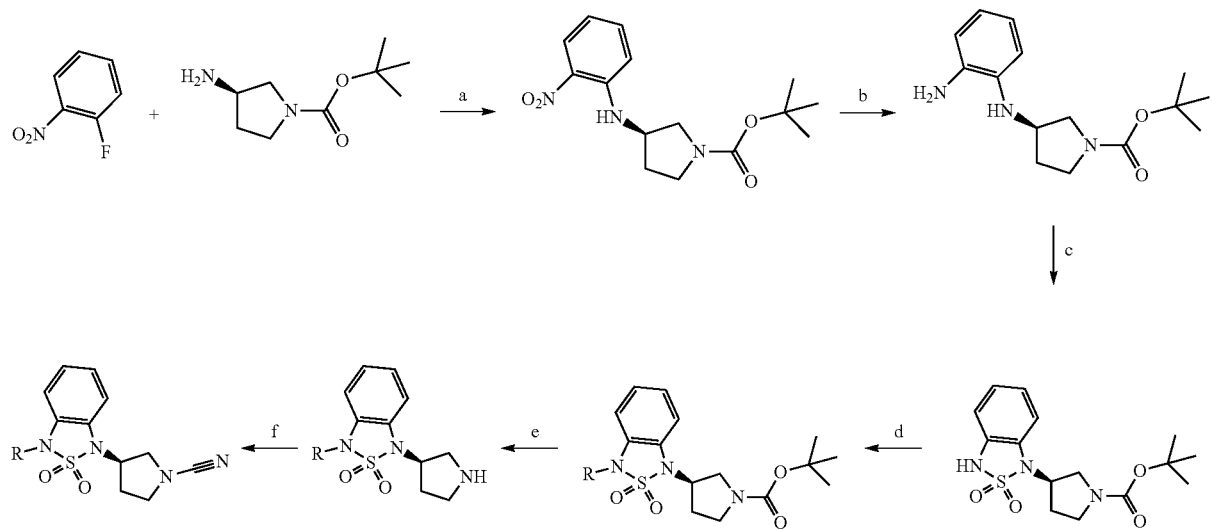

Reagents and conditions: a) K₂CO₃, DMF, 80° C. 15 h b) Pd/C, H₂, ethanol, rt, 15 h c) SO₂(NH₂)₂, pyridine, 100-130° C., 4-12 h d) NaH, R—Br, THF, rt, 3 h e) TFA, DCM, rt, 1-2 h f) cyanogen bromide, K₂CO₃, THF, rt 1-2 h.

General Scheme 3

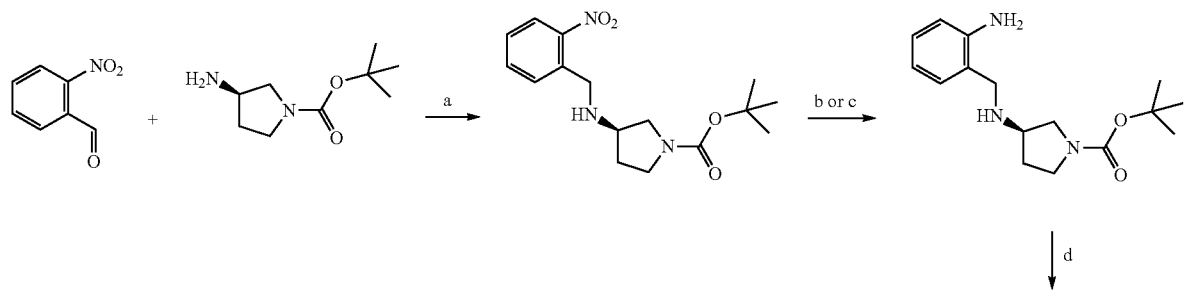

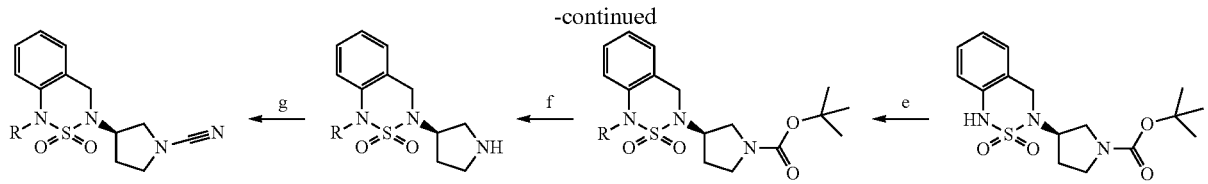

Reagents and conditions: a) NaBH₄, MeOH, rt, 15 h b) Pd/C, H₂, methanol, rt, 3 h c) iron powder, AcOH, THF, H₂O, 75° C., 1 h d) SO₂(NH₂)₂, pyridine, 100-130° C., 4-36 h e) NaH, R—Br, THF, 50° C., rt, 15 h f) TFA, DCM, rt, 1-2 h g) cyanogen bromide, K₂CO₃, THF, rt 1-2 h.

Example 1 (S)-3-(5-(3-(isoxazol-5-yl)phenyl)-1,1-dioxido-1,2,5-thiadiazolidin-2-yl)pyrrolidine-1-carbonitrile Synthesis According to Scheme 1 Steps a, b, d, e, f.

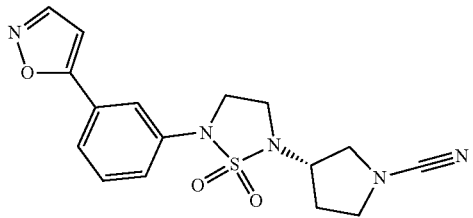 [SMILES: N#CN1CC[C@H](N2CCN(c3cccc(-c4ccno4)c3)S2(=O)=O)C1]

Step a. In a glass vial-1, to a solution of chlorosulfonyl isocyanate (1.00 g, 7.06 mmol) in DCM (10 ml) was added 2-bromoethanol (0.50 ml, 7.06 mmol) at 0° C. and stirred for 1 h.

Simultaneously in a glass vial-2, to a solution of tert-butyl (S)-3-aminopyrrolidine-1-carboxylate (1.57 g, 8.48 mmol) in DCM (10 ml) was added TEA (1.98 ml, 14.13 mmol) at 0° C. and stirred for 1 h.

After 1 h, the reaction mixture of vial-2 was added to the reaction mixture in vial-1 at 0° C. The resulting reaction mixture was stirred at rt for 2 h. The resulting reaction mixture was poured into water (50 ml) and extracted with DCM (2×50 ml). The combined organic phase was dried over Na₂SO₄, filtered and concentrated under reduced pressure. yielding tert-butyl (S)-3-((2-oxooxazolidine)-3-sulfonamido)pyrrolidine-1-carboxylate (1.85 g, 5.52 mmol). This material was used directly for the next step without further purification. LCMS: Method C, 1.89 min, MS: ES+ 336.3.

Step b. To a solution of 3-(isoxazol-5-yl)aniline (0.25 g, 1.56 mmol) in MeCN (15 ml) was added TEA (0.65 ml, 4.68 mmol) at rt. The reaction mixture was stirred at rt for 15 min and then treated with tert-butyl (S)-3-((2-oxooxazolidine)-3-sulfonamido)pyrrolidine-1-carboxylate (1.30 g, 3.90 mmol). The reaction mixture was heated at 70° C. for 2 h. The resulting reaction mixture was poured into water (50 ml) and extracted with EtOAc (3×20 ml). The combined organic phase was dried over Na₂SO₄, filtered and concentrated under reduced pressure. The resulting residue was purified by column chromatography (27% EtOAc in hexane) yielding tert-butyl (S)-3-((N-(3-(isoxazol-5-yl)phenyl)sulfamoyl)amino) pyrrolidine-1-carboxylate (0.22 g, 0.54 mmol). LCMS: Method C, 2.17 min, MS: ES+ 409.7.

Step d. To a solution of tert-butyl (S)-3-((N-(3-(isoxazol-5-yl)phenyl)sulfamoyl)amino) pyrrolidine-1-carboxylate (0.22 g, 0.539 mmol) in DMF (7 ml) was added K₂CO₃ (0.29 g, 2.16 mmol) at rt. The reaction mixture was stirred at rt for 15 min and then treated with 1,2-dibromoethane (0.12 g, 0.65 mmol). The reaction mixture was stirred at 100° C. for 1 h. The resulting reaction mixture was poured into water (50 ml) and extracted with EtOAc (3×30 ml). The combined organic phase was dried over Na₂SO₄, filtered and concentrated under reduced pressure. The resulting residue was purified by column chromatography (45% EtOAc in hexane) yielding tert-butyl (S)-3-(5-(3-(isoxazol-5-yl)phenyl)-1,1-dioxido-1,2,5-thiadiazolidin-2-yl)pyrrolidine-1-carboxylate (0.09 g, 0.21 mmol). LCMS: Method C, 2.26 min, MS: ES+ 435.5, 335.3

Step e. To a solution of tert-butyl (S)-3-(5-(3-(isoxazol-5-yl)phenyl)-1,1-dioxido-1,2,5-thiadiazolidin-2-yl)pyrrolidine-1-carboxylate (0.09 g, 0.21 mmol) in DCM (10 ml) was added TFA (0.9 ml) at 0° C. The reaction mixture was stirred at rt for 1 h. The resulting reaction mixture was concentrated under reduced pressure. yielding (S)-2-(3-(isoxazol-5-yl)phenyl)-5-(pyrrolidin-3-yl)-1,2,5-thiadiazolidine 1,1-dioxide TFA salt (0.09 g, 0.20 mmol) This material was used directly for the next step without further purification. LCMS: Method C, 1.67 min, MS: ES+ 335.49.

Step f. To a solution of (S)-2-(3-(isoxazol-5-yl)phenyl)-5-(pyrrolidin-3-yl)-1,2,5-thiadiazolidine 1,1-dioxide TFA salt (0.09 g, 0.20 mmol) in THF (5 ml) was added K₂CO₃ (0.11 g, 0.80 mmol) at rt. The reaction mixture was stirred at rt for 15 min. Cyanogen bromide (0.026 g, 0.24 mmol) was added to the reaction mixture at 0° C. and stirred at rt for 1 h. The resulting reaction mixture was poured into water (15 ml) and extracted with EtOAc (2×15 ml). The combined organic phase was dried over Na₂SO₄, filtered and concentrated under reduced pressure. The resulting residue was purified by column chromatography (65% EtOAc in hexane) yielding the title compound (0.02 g, 0.05 mmol). LCMS: Method B, 3.74 min, MS: ES+ 360.46; ¹H NMR (400 MHz, DMSO-d6) δ ppm 8.70 (d, J=2 Hz, 1H), 7.66-7.70 (m, 2H), 7.59 (t, J=7.6 Hz, 1H), 7.37-7.40 (m, 1H), 7.11 (d, J=2 Hz, 1H), 3.95-4.02 (m, 3H), 3.58-3.66 (m, 4H), 3.44-3.55 (m, 2H), 2.17-2.23 (m, 2H).

Example 2 (R)-3-(5-(4-methyl-3-oxo-3,4-dihydro-2H-benzo[b][1,4]oxazin-7-yl)-1,1-dioxido-1,2,5-thiadiazolidin-2-yl)pyrrolidine-1-carbonitrile

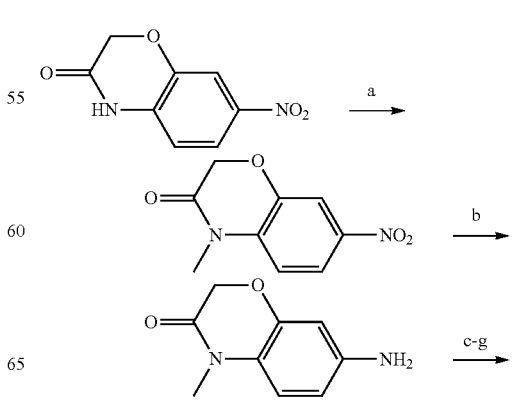

-continued

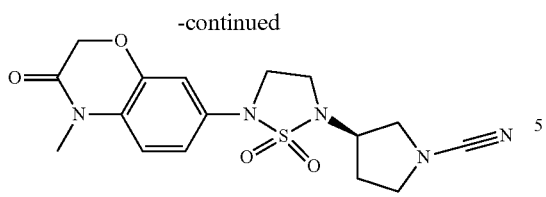

Step a. To a solution of 7-nitro-2H-1,4-benzoxazin-3(4H)-one (0.75 g, 3.86 mmol) in DMF (15 ml) was added $K_2CO_3$ (1.60 g, 11.59 mmol) at rt. The reaction mixture was stirred at rt for 30 min and then treated with methyl iodide (0.28 ml, 4.63 mmol) at 0° C. The reaction mixture was stirred at rt for 5 h and then poured into water (100 ml) and extracted with EtOAc (3×50 ml). The combined organic layer was washed with brine solution (50 ml). The organic phase was collected, dried over $Na_2SO_4$, filtered and concentrated under reduced pressure. The resulting residue was purified by column chromatography (40% EtOAc in hexane) yielding 4-methyl-7-nitro-2H-benzo[b][1,4]oxazin-3(4H)-one (0.85 g, quantitative). LCMS: Method C, 1.98 min, MS: ES+ 209.28.

Step b. To a solution of 4-methyl-7-nitro-2H-benzo[b][1,4]oxazin-3(4H)-one (0.85 g, 4.08 mmol) in MeOH:$H_2O$ (25.5 ml:12.7 ml) were added Fe powder (1.14 g, 20.42 mmol) and $NH_4Cl$ (2.18 g, 40.83 mmol) at rt. The reaction mixture was heated at 80° C. for 12 h. The resulting reaction mixture was filtered through celite hyflow and the celite cake was washed with MeOH (50 ml). The filtrate was concentrated under reduced pressure. The obtained residue was quickly poured into water (100 ml) and extracted with EtOAc (2×100 ml). The combined organic layer was washed with brine solution (100 ml), dried over $Na_2SO_4$, filtered and concentrated under reduced pressure yielding 7-amino-4-methyl-2H-benzo[b][1,4]oxazin-3(4H)-one (0.54 g, 3.03 mmol). This material was used directly for the next step without further purification. LCMS: Method C, 0.59 min, MS: ES+ 179.16.

Steps c-g. The remainder of the synthesis followed a procedure similar to that described for Example 1 steps a, b, d, e and f. LCMS: Method A, 3.45 min, MS: ES+ 378.0. $^1$H NMR (400 MHz, DMSO-d6) δ ppm 7.20 (d, J=8 Hz, 1H), 6.96 (dd, J=2.4 Hz, 8.8 Hz 1H), 6.91 (d, J=2.4 Hz, 1H), 4.68 (s, 2H), 3.91-3.97 (m, 1H), 3.82 (t, J=6.4 Hz, 2H), 3.59-3.63 (m, 1H), 3.50-3.57 (m, 4H), 3.42-3.48 (m, 1H), 3.26 (s, 3H), 2.12-2.20 (m, 2H).

Example 3 (R)-3-(1,1-dioxido-5-(3-oxo-3,4-dihydro-2H-benzo[b][1,4]oxazin-7-yl)-1,2,5-thiadiazolidin-2-yl)pyrrolidine-1-carbonitrile

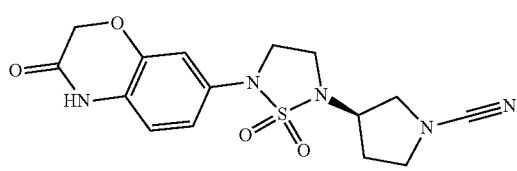 [SMILES: N#CN1CC[C@@H](N2CCN(c3ccc4c(c3)OCC(=O)N4)S2(=O)=O)C1]

Synthesised using a procedure similar to that described for Example 2, omitting step a. LCMS: Method B, 3.06 min, MS: ES+ 364.65. $^1$H NMR (400 MHz, DMSO-d6) δ ppm 10.74 (s, 1H), 6.85-6.92 (m, 3H), 4.59 (s, 2H), 3.90-3.94 (m, 1H), 3.76-3.80 (t, J=6.0 Hz, 2H), 3.42-3.60 (m, 6H), 2.13-2.19 (m, 2H).

Example 4 (R)-3-(5-(4-methyl-3-oxo-3,4-dihydro-2H-benzo[b][1,4]oxazin-6-yl)-1,1-dioxido-1,2,5-thiadiazolidin-2-yl)pyrrolidine-1-carbonitrile

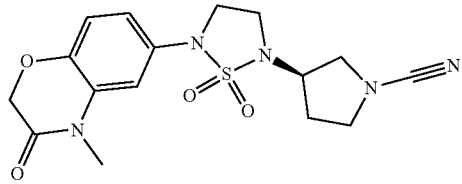 [SMILES: CN1C(=O)COc2ccc(N3CCN([C@@H]4CCN(C#N)C4)S3(=O)=O)cc21]

Synthesised using a procedure similar to that described for Example 2, using 6-nitro-2H-1,4-benzoxazin-3(4H)-one. LCMS: Method B, 3.38 min, MS: ES+ 378.6. $^1$H NMR (400 MHz, DMSO-d6) δ ppm 7.06 (d, J=8.40 Hz, 1H), 6.99 (d, J=2.40 Hz, 1H), 6.96 (dd, J=8.80, 2.80 Hz, 1H), 4.66 (s, 2H), 3.92-3.95 (m, 1H), 3.85-3.88 (m, 2H), 3.39-3.64 (m, 6H), 3.27 (s, 3H), 2.15-2.21 (m, 2H).

Example 5 (R)-3-(1,1-dioxido-5-(3-oxo-3,4-dihydro-2H-benzo[b][1,4]oxazin-6-yl)-1,2,5-thiadiazolidin-2-yl)pyrrolidine-1-carbonitrile

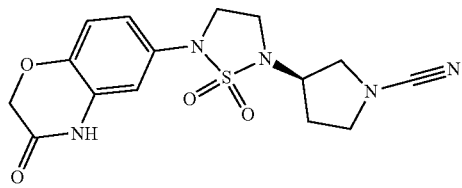 [SMILES: N#CN1CC[C@@H](N2CCN(c3ccc4c(c3)NC(=O)CO4)S2(=O)=O)C1]

Synthesised using a procedure similar to that described for Example 2, using 6-nitro-2H-1,4-benzoxazin-3(4H)-one and omitting step a. LCMS: Method B, 3.18 min, MS: ES+ 364.50. $^1$H NMR (400 MHz, DMSO-d6) δ ppm 10.79 (s, 1H), 7.00 (d, J=8.80 Hz, 1H), 6.90 (d, J=2.80 Hz, 1H), 6.80 (dd, J=8.40, 2.40 Hz, 1H), 4.57 (s, 2H), 3.90-3.96 (m, 1H), 3.75-3.78 (m, 2H), 3.59-3.63 (m, 1H), 3.34-3.56 (m, 5H), 2.12-2.21 (m, 2H).

Example 6 (R)-3-(5-(4-(2-hydroxyethyl)-3-oxo-3,4-dihydro-2H-benzo[b][1,4]oxazin-6-yl)-1,1-dioxido-1,2,5-thiadiazolidin-2-yl)pyrrolidine-1-carbonitrile

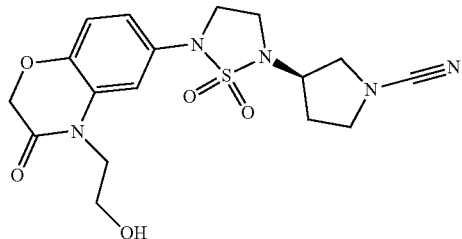 [SMILES: N#CN1CC[C@@H](N2CCN(c3ccc4c(c3)N(CCO)C(=O)CO4)S2(=O)=O)C1]

Synthesised as a by-product in the preparation of Example 5, upon addition of 2-bromoethanol in step d. LCMS: Method B, 3.11 min, MS: ES+ 408.60. $^1$H NMR (400 MHz, DMSO-d6) δ ppm 7.15 (d, J=2.4 Hz, 1H), 7.06 (d, J=8.4 Hz, 1H), 6.94 (dd, J=2.4, 8.8 Hz, 1H), 4.92-4.93 (m, 1H), 4.64 (s, 2H), 3.85-3.97 (m, 3H), 3.82-3.85 (m, 2H), 3.47-3.64 (m, 7H), 2.14-2.20 (m, 2H).

Example 7 3-(5-(4-methyl-3-oxo-3,4-dihydro-2H-benzo[b][1,4]oxazin-6-yl)-1,1-dioxido-1,2,5-thiadiazolidin-2-yl)pyrrolidine-1-carbonitrile

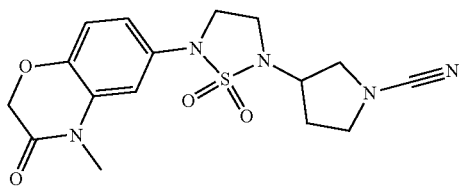 [SMILES: CN1C(=O)COc2ccc(N3CCN(C4CCN(C#N)C4)S3(=O)=O)cc21]

Synthesised using a procedure similar to that described for Example 4, using 6-nitro-2H-1,4-benzoxazin-3(4H)-one and (rac) tert-butyl 3-aminopyrrolidine-1-carboxylate as starting materials. LCMS: Method B, 3.39 min, MS: ES+ 378.7. $^1$H NMR (400 MHz, DMSO-$d_6$) δ ppm 7.06 (d, J=8.40 Hz, 1H), 6.99 (d, J=2.40 Hz, 1H), 6.96 (dd, J=8.40, 2.40 Hz, 1H), 4.66 (s, 2H), 3.92-3.95 (m, 1H), 3.85-3.88 (m, 2H), 3.39-3.64 (m, 6H), 3.27 (s, 3H), 2.15-2.21 (m, 2H).

Example 8 (R)-3-(5-(4-methoxy-3-morpholinophenyl)-1,1-dioxido-1,2,5-thiadiazolidin-2-yl)pyrrolidine-1-carbonitrile

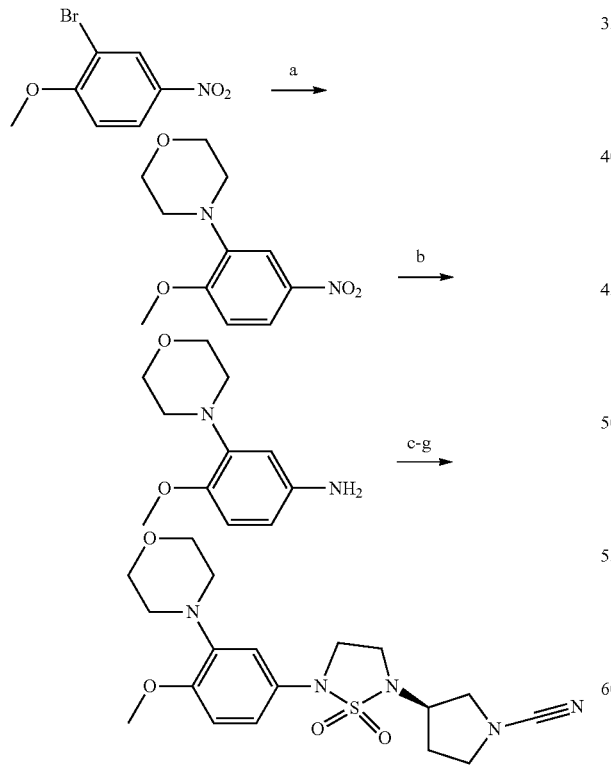

Step a. To a solution of 2-bromo-4-nitroanisole (2.15 g, 9.26 mmol) in toluene (30 ml) were added morpholine (1.21 g, 13.90 mmol) and sodium tert-butoxide (1.33 g, 13.9 mmol) at rt. The reaction mixture was degassed for 20 min. BINAP (0.05 g, 0.092 mmol), Pd$_2$(dba)$_3$ (0.25 g, 0.28 mmol), and DBU (0.11 g, 0.74 mmol) were added to the reaction mixture at rt. The reaction mixture was heated at 100° C. for 17 h. The resulting reaction mixture was concentrated under reduced pressure. The resulting residue was purified by column chromatography (10% EtOAc in hexane) yielding 4-(2-methoxy-5-nitrophenyl)morpholine (0.97 g, 4.07 mmol). LCMS: Method C, 1.98 min, MS: ES+ 239.20.

Step b. To a solution of 4-(2-methoxy-5-nitrophenyl) morpholine (0.50 g, 2.10 mmol) in MeOH (10 ml) was added 10% dry Pd/C (0.025 g) at rt. The reaction mixture was purged with H$_2$ gas at rt for 2 h. The resulting mixture was carefully filtered through celite hyflow, washed with EtOAc (20 ml) and concentrated under reduced pressure yielding 4-methoxy-3-morpholinoaniline (0.43 g, 2.07 mmol). This material was used directly for the next step without further purification. LCMS: Method C, 1.24 min, MS: ES+ 209.19.

Steps c-g. The remainder of the synthesis followed a procedure similar to that described for Example 1, steps a, b, d, e and f. LCMS: Method B, 3.42 min, MS: ES+ 408.65. $^1$H NMR (400 MHz, CDCl$_3$) δ ppm 6.93-6.96 (m, 2H), 6.88 (d, J=8.4 Hz, 1H), 3.97-3.98 (m, 1H), 3.88-3.91 (m, 7H), 3.80-3.83 (m, 2H), 3.70-3.74 (m, 1H), 3.60-3.64 (m, 2H), 3.47-3.57 (m, 3H), 3.10 (t, J=4.4 Hz, 4H), 2.33 (q, J=7.2 Hz, 2H).

Example 9 (3R)-3-(1,1-dioxido-5-(1-(pyridin-2-yl) pyrrolidin-3-yl)-1,2,5-thiadiazolidin-2-yl)pyrrolidine-1-carbonitrile

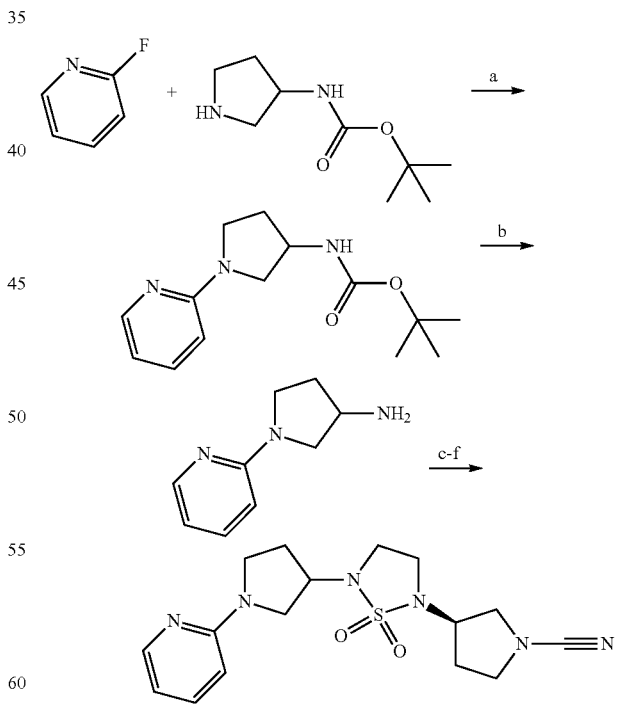

Step a. A neat mixture of 2-fluoropyridine (2.00 g, 20.60 mmol) and 3(R)-(tert-butoxycarbonylamino)-pyrrolidine (3.80 g, 20.60 mmol) was heated at 120° C. for 2 h. The resulting reaction mixture was concentrated under reduced pressure yielding tert-butyl (1-(pyridin-2-yl)pyrrolidin-3-yl)

carbamate (4.50 g, 17.10 mmol). This material was used directly for the next step without further purification. LCMS: Method C, 1.63 min, MS: ES+ 264.0.

Step b. To a solution of tert-butyl (1-(pyridin-2-yl)pyrrolidin-3-yl)carbamate (2.00 g, 7.60 mmol) in DCM (20 ml) was added TFA (20 ml) at 0° C. The reaction mixture was stirred at 0° C. to rt for 2 h. The resulting reaction mixture was concentrated under reduced pressure yielding 1-(pyridin-2-yl)pyrrolidin-3-amine TFA salt (2.00 g, 7.22 mmol). This material was used directly for the next step without further purification. LCMS: Method C, 0.27 min, MS: ES+ 164.2.

Steps c-g. The remainder of the synthesis followed a procedure similar to that described for Example 1, steps a, b, d, e and f. LCMS: Method B, 2.36 min, MS: ES+ 363.39. $^1$H NMR (400 MHz, DMSO-d6) δ ppm 8.07 (dd, J=1.2 Hz, J=4.8 Hz, 1H), 7.47-7.52 (m, 1H), 6.57 (q, J=5.2 Hz, 1H), 6.45 (d, J=8.4 Hz, 1H), 3.97-4.89 (m, 1H), 3.86-3.92 (m, 1H), 3.75-3.79 (m, 1H), 3.57-3.67 (m, 5H), 3.36-3.51 (m, 6H), 2.31-2.43 (m, 2H), 2.23-2.30 (m, 2H).

Example 10 (R)-3-(5-(2'-methoxy-[1,1'-biphenyl]-3-yl)-1,1-dioxido-1,2,5-thiadiazolidin-2-yl)pyrrolidine-1-carbonitrile

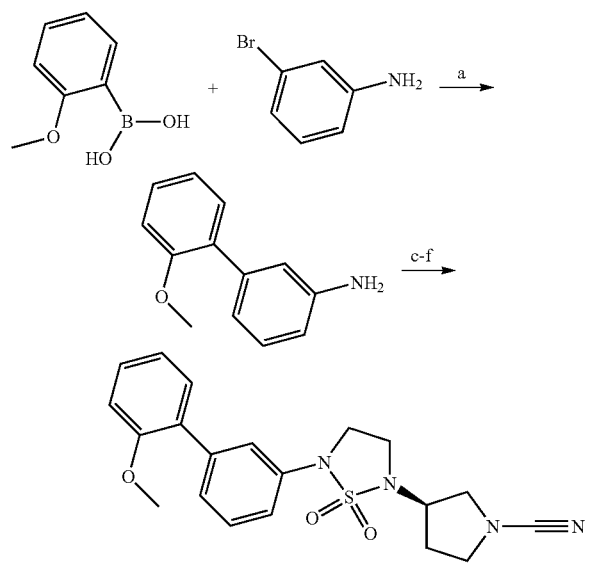

Step a. A solution of 3-bromoaniline (0.70 g, 4.07 mmol) and 2-methoxyphenylboronic acid (0.618 g, 4.07 mmol) in DMF:water (5:1, 18 ml) was prepared in a glass vial. The reaction mixture was treated with Na$_2$CO$_3$ (1.29 g, 12.21 mmol) and degassed for 30 min before adding Pd(PPh$_3$)$_4$ (0.470 g, 0.41 mmol). The glass vial was sealed and subjected to heating at 80° C. for 16 h. The resulting reaction mixture was poured into water (200 ml) and extracted with EtOAc (2×100 ml). The combined organic phase was collected, dried over Na$_2$SO$_4$, filtered and concentrated under reduced pressure yielding 2'-methoxy-[1,1'-biphenyl]-3-amine (0.90 g, quantitative). This material was used directly for the next step without further purification. LCMS: Method C, 1.81 min, MS: ES+ 200.5.

The following procedure was conducted according to General Scheme 1, steps c, d, e and f.

Step c. To a solution of (R)-1-Boc-3-aminopyrrolidine (0.50 g, 2.69 mmol) in DCM (15 ml) was added imidazole (0.21 g, 3.22 mmol) at −78° C. and stirred for 10 min. TEA (0.96 ml, 6.72 mmol) and SO$_2$Cl$_2$ (0.32 ml, 4.03 mmol) were added to the reaction mixture at −78° C. and stirred for 1 hr. The reaction mixture was treated with 2'-methoxy-[1,1'-biphenyl]-3-amine (0.53 ml, 2.69 mmol) at −78° C. and stirred at rt for 16 h. The resulting reaction mixture was poured into saturated citric acid solution (150 ml) and extracted with DCM (3×50 ml). The organic layer was washed with saturated NaHCO$_3$ solution (100 ml). The combined organic phase was collected, dried over Na$_2$SO$_4$, filtered and concentrated under reduced pressure yielding a tert-butyl (R)-3-((N-(2'-methoxy-[1,1'-biphenyl]-3-yl)sulfamoyl)amino)-pyrrolidine-1-carboxylate (0.70 g, 1.56 mmol). This material was used directly for the next step without further purification. LCMS: Method B, 4.87 min, MS: ES+ 418.3 (M−56).

Steps d-f. The title compound was synthesised from the intermediate above using a procedure similar to that described for steps d-f of Example 1. LCMS: Method B, 4.27 min, MS: ES+ 399.2. $^1$H NMR (400 MHz, DMSO-d6) δ ppm 7.44 (t, J=8.0 Hz, 1H), 7.35-7.40 (m, 1H), 7.27-7.34 (m, 3H), 7.21 (dd, J=1.6 Hz, J=7.2 Hz, 1H), 7.13 (d, J=8.0 Hz, 1H), 7.03-7.07 (m, 1H), 3.95-3.99 (m, 1H), 3.88-3.93 (m, 2H), 3.38-3.65 (m, 7H), 3.33 (s, 2H), 2.16-2.22 (m, 2H).

Compounds in Table 1 were synthesised using a procedure similar to that described for Example 10, steps c-f, using (R)-1-Boc-3-aminopyrrolidine.

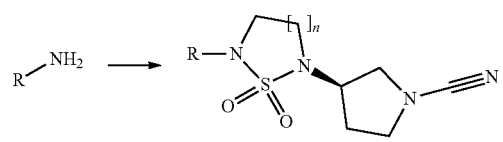

TABLE 1

| Ex | R | n | Name | LCMS Method | LCMS RT (min) | MS ES + |
| --- | --- | --- | --- | --- | --- | --- |
| 11 | ![biphenyl] | 1 | (R)-3-(5-([1,1'-biphenyl]-4-yl)-1,1-dioxido-1,2,5-thiadiazolidin-2-yl)pyrrolidine-1-carbonitrile | B | 4.35 | 369.23 |

TABLE 1-continued

| Ex | R | n | Name | LCMS Method | LCMS RT (min) | MS ES + |
|---|---|---|---|---|---|---|
| 12 | | 2 | (R)-3-(6-([1,1'-biphenyl]-4-yl)-1,1-dioxido-1,2,6-thiadiazinan-2-yl)pyrrolidine-1-carbonitrile | B | 4.39 | 383.24 |
| 13 | | 1 | (R)-3-(5-([1,1'-biphenyl]-3-yl)-1,1-dioxido-1,2,5-thiadiazolidin-2-yl)pyrrolidine-1-carbonitrile | B | 4.35 | 369.38 |
| 14 | | 2 | (R)-3-(6-([1,1'-biphenyl]-3-yl)-1,1-dioxido-1,2,6-thiadiazinan-2-yl)pyrrolidine-1-carbonitrile | B | 4.36 | 383.19 |
| 15 | | 1 | (R)-3-(5-(4-methoxy-[1,1'-biphenyl]-3-yl)-1,1-dioxido-1,2,5-thiadiazolidin-2-yl)pyrrolidine-1-corbonitrile | B | 4.18 | 399.23 |
| 16 | | 1 | (R)-3-(5-(3'-methoxy-[1,1'-biphenyl]-3-yl)-1,1-dioxido-1,2,5-thiadiazolidin-2-yl)pyrrolidine-1-carbonitrile | B | 4.28 | 399.2 |
| 17 | | 1 | (R)-3-(5-(2'-methoxy-[1,1'-biphenyl]-4-yl)-1,1-dioxido-1,2,5-thiadiazolidin-2-yl)pyrrolidine-l-carbonitrile | B | 4.32 | 399.23 |
| 18 | | 1 | (R)-3-(1,1-dioxido-5-(4-(pyridin-4-yl)phenyl)-1,2,5-thiadiazolidin-2-yl)pyrrolidine-1-carbonitrile | B | 2.64 | 370.19 |
| 19 | | 1 | (R)-3-(1,1-dioxido-5-(3-(pyridin-4-yl)phenyl)-1,2,5-thiadiazolidin-2-yl)pyrrolidine-1-carbonitrile | B | 2.74 | 370.19 |

TABLE 1-continued

| Ex | R | n | Name | LCMS Method | LCMS RT (min) | MS ES + |
|---|---|---|---|---|---|---|
| 20 | 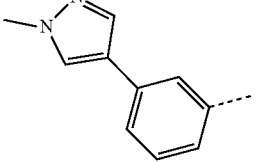 | 1 | (R)-3-(5-(3-(1-methyl-1H-pyrazol-4-yl)phenyl)-1,1-dioxido-1,2,5-thiadiazolidin-2-yl)pyrrolidine-1-corbonitrile | A | 3.60 | 372.93 |
| 21 | 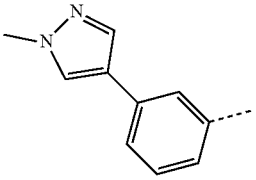 | 2 | (R)-3-(6-(3-(1-methyl-1H-pyrazol-4-yl)phenyl)-1,1-dioxido-1,2,6-thiadiazinan-2-yl)pyrrolidine-1-carbonitrile | A | 3.77 | 386.90 |
| 22 | 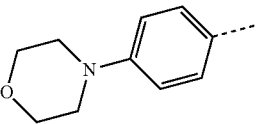 | 1 | (R)-3-(5-(4-morpholinophenyl)-1,1-dioxido-1,2,5-thiadiazolidin-2-yl)pyrrolidine-1-carbonitrile | B | 3.41 | 378.54 |
| 23 | 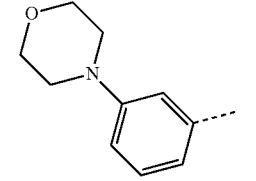 | 1 | (R)-3-(5-(3-chloro-4-morpholinophenyl)-1,1-dioxido-1,2,5-thiadiazolidin-2-yl)pyrrolidine-1-carbonitrile | B | 3.88 | 412.44 |
| 24 | 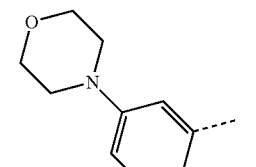 | 1 | (R)-3-(5-(3-morpholinophenyl)-1,1-dioxido-1,2,5-thiadiazolidin-2-yl)pyrrolidine-1-carbonitrile | B | 3.55 | 378.44 |
| 25 | 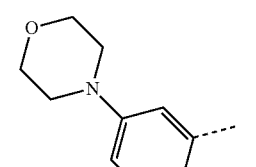 | 2 | (R)-3-(6-(3-morpholinophenyl)-1,1-dioxido-1,2,6-thiadiazinan-2-yl)pyrrolidine-1-carbonitrile | B | 3.76 | 392.52 |
| 26 | 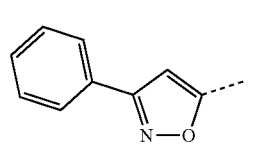 | 1 | (R)-3-(1,1-dioxido-5-(3-phenylisoxazol-5-yl)-1,2,5-thiadiazolidin-2-yl)pyrrolidine-1-carbonitrile | B | 4.13 | 360.51 |
| 27 | 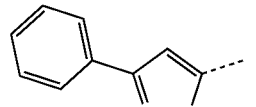 | 2 | (R)-3-(1,1-dioxido-6-(3-phenylisoxazol-5-yl)-1,2,6-thiadiazinan-2-yl)pyrrolidine-1-carbonitrile | B | 4.28 | 374.39 |
| 28 | 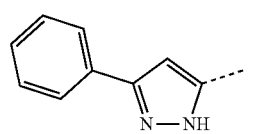 | 1 | (R)-3-(1,1-dioxido-5-(3-phenyl-1H-pyrazol-5-yl)-1,2,5-thiadiazolidin-2-yl)pyrrolidine-1-carbonitrile | B | 3.62 | 359.41 |

TABLE 1-continued

| Ex | R | n | Name | LCMS Method | LCMS RT (min) | MS ES+ |
|---|---|---|---|---|---|---|
| 29 | 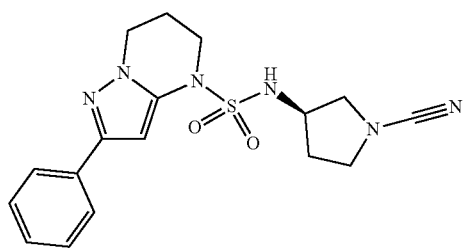 | 2 | (R)-3-(1,1-dioxido-6-(3-phenyl-1H-pyrazol-5-yl)-1,2,6-thiadiazinan-2-yl)pyrrolidine-1-carbonitrile | B | 3.78 | 373.44 |

Example 30 (R)—N-(1-cyanopyrrolidin-3-yl)-2-phenyl-6,7-dihydropyrazolo[1,5-a]pyrimidine-4(5H)-sulfonamide Synthesised using a procedure similar to that described for Example 10, steps c-f, using 3-amino-5-phenyl-1H-pyrazole, formed as a by-product during the synthesis of Example 29 upon addition of 1,3-dibromopropane in step d. LCMS: Method B, 3.74 min, MS: ES+ 373.39. $^1$H NMR (400 MHz, DMSO-d6) δ ppm 8.49 (d, J=6.4 Hz, 1H), 7.73 (d, J=7.2 Hz, 2H), 7.40 (t, J=8 Hz, 2H), 7.30 (t, J=7.3 Hz, 1H), 6.50 (s, 1H), 4.15 (t, J=6.4 Hz, 2H), 3.88-3.92 (m, 1H), 3.74 (t, J=5.6 Hz, 2H), 3.41-3.49 (m, 2H), 3.36-3.38 (m, 1H), 3.16-3.19 (m, 1H), 2.17-2.20 (m, 2H), 1.97-2.01 (m, 1H), 1.78-1.81 (m, 1H).

Compounds in Table 1.1 were synthesised using a procedure similar to that described for Example 10, steps c-f, using tert-butyl (S)-3-aminopyrrolidine-1-carboxylate as starting material.

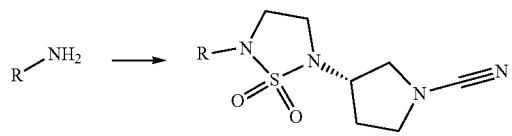

TABLE 2

| Ex | R | Name | LCMS Method | LCMS RT (min) | MS ES+ | $^1$H NMR (400 MHz, DMSO-d6) δ ppm |
|---|---|---|---|---|---|---|
| 31 | phenyl | (S)-3-(1,1-dioxido-5-phenyl-1,2,5-thiadiazolidin-2-yl)pyrrolidine-1-carbonitrile | B | 3.42 | 293.12 | 7.40-7.44 (m, 2 H), 7.23-7.25 (m, 2 H), 7.17 (t, J = 7.2 Hz, 14.8 Hz, 1 H), 3.92-3.97 (m, 1 H), 3.84-3.87 (m, 2 H), 3.60-3.64 (m, 1 H), 3.5-3.58 (m, 3 H), 3.34-3.49 (m, 2 H), 2.15-2.21 (m, 2 H) |
| 32 | 4-(pyridin-4-yl)phenyl | (S)-3-(1,1-dioxido-5-(4-(pyridin-4-yl)phenyl)-1,2,5-thiadiazolidin-2-yl)pyrrolidine-1-carbonitrile | B | 2.60 | 370.2 | 8.63 (dd, J = 1.2 Hz, 4.8 Hz, 2 H), 7.90 (d, J = 8.8 Hz, 2 H), 7.72 (dd, J = 1.2 Hz, 4.8 Hz, 2 H), 7.36 (d, J = 8.8 Hz, 2 H), 3.96-4.0 (m, 1 H), 3.91-3.95 (m, 2 H), 3.54-3.66 (m, 4 H), 3.44-3.52 (m, 2 H), 2.17-2.23 (m, 2 H) |
| 33 | 3-(pyridin-4-yl)phenyl | (S)-3-(1,1-dioxido-5-(3-(pyridin-4-yl)phenyl)-1,2,5-thiadiazolidin-2-yl)pyrrolidine-1-carbonitrile | B | 2.70 | 370.25 | 8.68 (d, J = 6.0 Hz, 2 H), 7.72 (dd, J = 1.2 Hz, 4.8 Hz, 2 H), 7.54-7.64 (m, 3 H), 7.38-7.40 (m, 1 H), 3.95-4.0 (m, 3 H), 3.57-3.66 (m, 4 H), 3.44-3.55 (m, 2H), 2.18-2.23 (m, 2 H) |

TABLE 2-continued

| Ex | R | Name | LCMS Method | LCMS RT (min) | MS ES + | 1H NMR (400 MHz, DMSO-d6) δ ppm |
|---|---|---|---|---|---|---|
| 34 | | (S)-3-(5-([1,1'-biphenyl-4-yl)-1,1-dioxido-1,2,5-thiadiazolidin-2-yl)pyrrolidine-1-carbonitrile | B | 4.30 | 369.3 | 7.73 (d, J = 8.8 Hz, 2 H), 7.67 (dd, J = 1.2 Hz, 7.2 Hz, 2 H), 7.47 (t, J = 7.2 Hz, 14.4 Hz, 2 H), 7.36 (d, J = 7.2 Hz, 1 H), 7.33 (d, J = 8.8 Hz, 2 H), 3.95-4.0 (m, 1 H), 3.89-3.92 (m, 2 H), 3.44-3.66 (m, 6 H), 2.13-2.26 (m, 2 H) |
| 35 | | (S)-3-(5-([1,1'-biphenyl]-3-yl)-1,1-dioxido-1,2,5-thiadiozolidin-2-yl)pyrrolidine-1-carbonitrile | B | 4.34 | 369.27 | 7.67 (d, J = 8.8 Hz, 2 H), 7.39-7.53 (m, 6 H), 7.26-7.29 (m, 1 H), 3.91-3.94 (m, 3 H), 3.44-3.66 (m, 6 H), 2.15-2.24 (m, 2 H) |
| 36 | | (S)-3-(1,1-dioxido-5-(6-phenylpyridin-2-yl)-1,2,5-thiadiazolidin-2-yl)pyrrolidine-1-carbonitrile | B | 4.40 | 370.55 | 8.12 (d, J = 8.8 Hz, 2H), 7.93 (t, J = 8 Hz, 1 H), 7.73 (d, J = 7.6 Hz, 1 H), 7.43-7.52 (m, 3 H), 7.09 (d, J = 8 Hz, 1 H), 4.08 (t, J = 6 Hz, 2H), 3.98-4.01 (m, 1 H), 3.44-3.67 (m, 6 H), 2.18-2.24 (m, 2 H) |

Example 37 3-(1,1-dioxido-5-phenyl-1,2,5-thiadiazolidin-2-yl)pyrrolidine-1-carbonitrile

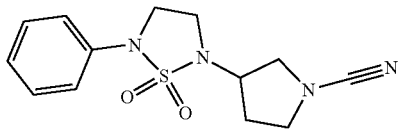 [SMILES: N#CN1CCC(N2CCN(c3ccccc3)S2(=O)=O)C1]

Synthesised using a procedure similar to that described for Example 10 starting from aniline. LCMS: Method A, 3.84 min, MS: ES+ 292.92; 1H NMR (400 MHz, DMSO-d6) δ ppm 7.40-7.44 (m, 2H), 7.23-7.26 (m, 2H), 7.16-7.19 (m, 1H), 3.94-3.97 (m, 1H), 3.85 (t, J=12.8 Hz, 2H), 3.43-3.64 (m, 6H), 2.15-2.21 (m, 2H)

Example 38 3-(1,1-dioxido-6-phenyl-1,2,6-thiadiazinan-2-yl)pyrrolidine-1-carbonitrile

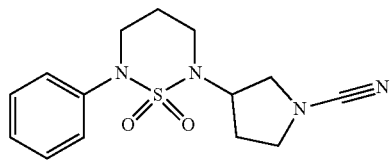 [SMILES: N#CN1CCC(N2CCCN(c3ccccc3)S2(=O)=O)C1]

Synthesised using a procedure similar to that described for Example 10 starting from aniline. LCMS: Method A, 4.12 min, MS: ES+ 306.99; 1H NMR (400 MHz, DMSO-d6) δ ppm 7.37-7.49 (m, 4H), 7.28-7.33 (m, 1H), 4.26-4.30 (m, 1H), 3.67-3.78 (m, 1H), 3.50-3.65 (m, 5H), 3.39-3.47 (m, 2H), 2.18-2.23 (m, 1H), 2.06-2.11 (m, 1H), 1.88-1.92 (m, 1H), 1.79-1.84 (m, 1H)

Example 39 (3R,4S)-3-(5-([1,1'-biphenyl]-4-yl)-1,1-dioxido-1,2,5-thiadiazolidin-2-yl)-4-methylpyrrolidine-1-carbonitrile

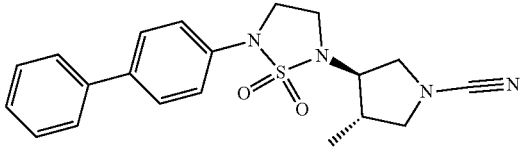 [SMILES: C[C@H]1CN(C#N)C[C@@H]1N1CCN(c2ccc(-c3ccccc3)cc2)S1(=O)=O]

Synthesised using a procedure similar to that described for Example 10 starting from 4-phenylaniline. LCMS: Method B, 4.59 min, MS: ES+ 383.04; 1H NMR (400 MHz, DMSO-d6) δ ppm 7.72-7.75 (m, 2H), 7.66-7.68 m (2H), 7.45-7.49 (m, 2H), 7.33-7.38 (m, 3H), 3.91 (t, J=6.4 Hz, 2H), 3.76-3.81 (m, 1H), 3.57-3.66 (m, 5H), 3.31-3.35 (m, 1H), 3.10 (t, J=9.2 Hz, 1H), 1.06 (d, J=6.8 Hz, 3H).

Example 40 (3S,4R)-3-methyl-4-(5-(3-(4-methylpiperazin-1-yl)phenyl)-1,1-dioxido-1,2,5-thiadiazolidin-2-yl)pyrrolidine-1-carbonitrile

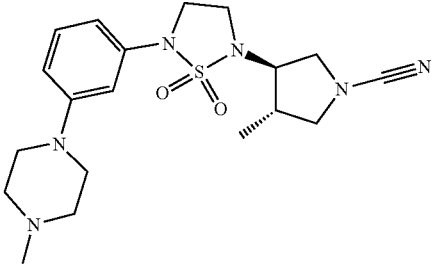 [SMILES: C[C@H]1CN(C#N)C[C@@H]1N1CCN(c2cccc(N3CCN(C)CC3)c2)S1(=O)=O]

Synthesised using a procedure similar to that described for Example 10 starting from 3-(4-methylpiperazin-1-yl) aniline. LCMS: Method A, 3.72 min, MS: ES+ 405.07; ¹H NMR (400 MHz, DMSO-d6) δ ppm 7.21 (t, J=8 Hz, 1H), 6.73-6.76 (m, 2H), 6.68 (d, J=8 Hz, 1H), 3.83 (t, J=6 Hz, 2H), 3.71-3.73 (m, 1H), 3.59-3.64 (m, 3H), 3.52-3.55 (m, 2H), 3.06-3.15 (m, 5H), 2.45-2.46 (m, 5H), 2.22 (s, 3H), 1.04 (d, J=6.4 Hz, 3H)

Example 41 (3S,4R)-3-methyl-4-(5-(3-morpholinophenyl)-1,1-dioxido-1,2,5-thiadiazolidin-2-yl)pyrrolidine-1-carbonitrile

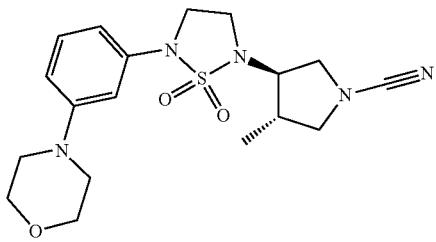 [SMILES: C[C@H]1CN(C#N)C[C@@H]1N1CCN(c2cccc(N3CCOCC3)c2)S1(=O)=O]

Synthesised using a procedure similar to that described for Example 10 starting from 3-morpholinoaniline. LCMS: Method A, 3.93 min, MS: ES+ 392.03; ¹H NMR (400 MHz, DMSO-d6) δ ppm 7.24 (t, J=8 Hz, 1H), 6.71-6.78 (m, 3H), 3.85 (t, J=12 Hz, 2H), 3.69-3.75 (m, 5H), 3.59-3.64 (m, 3H), 3.52-3.56 (m, 2H), 3.06-3.12

Example 42 (R)-3-(5-(6-methoxy-[1,1'-biphenyl]-3-yl)-1,1-dioxido-1,2,5-thiadiazolidin-2-yl)pyrrolidine-1-carbonitrile

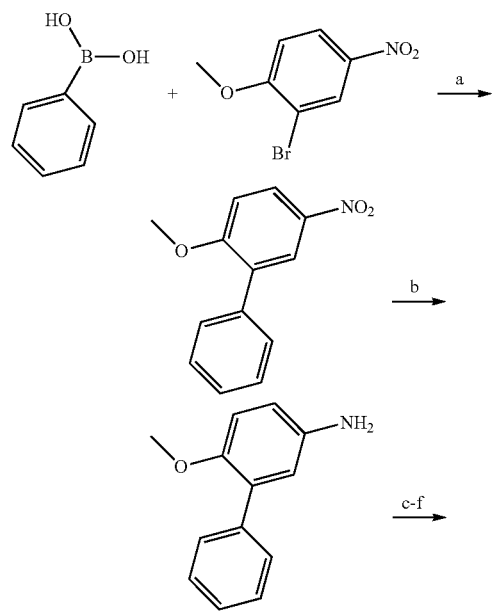

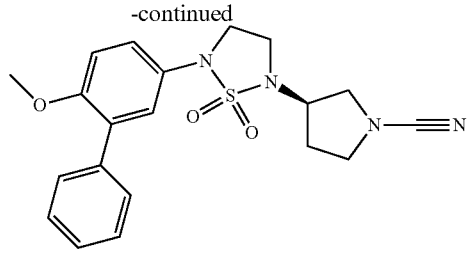

Step a. A solution of 2-bromo-4-nitroanisole (0.60 g, 2.59 mmol) and phenylboronic acid (0.315 g, 2.59 mmol) in toluene:water (5:1, 18 ml) was prepared in a glass vial. The reaction mixture was treated with K₂CO₃ (1.00 g, 7.76 mmol) and degassed for 30 min before adding Pd(PPh₃)₄ (0.298 g, 0.26 mol). The glass vial was sealed and subjected to heating at 80° C. for 16 h. The resulting reaction mixture was poured into water (200 ml) and extracted with EtOAc (3×50 ml). The combined organic phase was collected, dried over Na₂SO₄, filtered and concentrated under reduced pressure. The resulting residue was purified by column chromatography (8% EtOAc in hexane) yielding 2-methoxy-5-nitro-1,1'-biphenyl (0.53 g, 2.31 mmol). This material was used directly for the next step without further purification. ¹H NMR (400 MHz, CDCl₃) δ ppm 8.27 (dd, J=2.0 Hz, J=8.0 Hz, 2H), 7.54 (d, J=7.2 Hz, 2H), 7.42-7.49 (m, 3H), 7.06 (d, J=9.2 Hz, 1H), 3.95 (s, 3H).

Step b. To a solution of 2-methoxy-5-nitro-1,1'-biphenyl (0.53 g, 2.313 mmol) in ethanol (25 ml) was added 10% dry Pd/C (0.2 g) at rt. The reaction mixture was purged with H₂ gas at rt for 2 h. The resulting reaction mixture was carefully filtered through celite hyflow and concentrated under reduced pressure yielding 6-methoxy-[1,1'-biphenyl]-3-amine (0.44 g, 2.235 mmol). This material was used directly for the next step without further purification. LCMS: Method C, 1.58 min, MS: ES+ 199.8.

Steps c-g. The remainder of the synthesis followed a procedure similar to that described for Example 10, steps c-f. LCMS: Method B, 4.18 min, MS: ES+ 399.2. ¹H NMR (400 MHz, DMSO-d6) δ ppm 7.48 (d, J=7.2 Hz, 2H), 7.43 (t, J=7.2 Hz, 2H), 7.35 (t, J=7.2 Hz, 1H), 7.28 (dd, J=2.8 Hz, J=8.8 Hz, 1H), 7.18 (dd, J=2.4 Hz, J=11.2 Hz, 2H), 3.90-3.93 (m, 1H), 3.85 (t, J=6.4 Hz, 2H), 3.77 (s, 3H), 3.41-3.63 (m, 6H), 2.13-2.22 (m, 2H).

Example 43 (R)-3-(5-(2-methoxy-[1,1'-biphenyl]-4-yl)-1,1-dioxido-1,2,5-thiadiazolidin-2-yl)pyrrolidine-1-carbonitrile

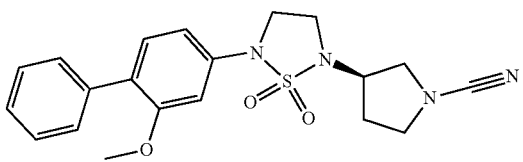 [SMILES: COc1cc(N2CCN([C@@H]3CCN(C#N)C3)S2(=O)=O)ccc1-c1ccccc1]

Synthesised using a procedure similar to that described for Example 42 starting from 2-bromo-5-nitroanisole. LCMS: Method A, 4.82 min, MS: ES+ 399.0. ¹H NMR (400 MHz, DMSO-d6) δ ppm 7.47 (d, J=1.2 Hz, 2H), 7.38-7.45 (m, 2H), 7.29-7.34 (m, 2H), 6.93 (dd, J=2.4 Hz, J=10.4 Hz, 2H), 3.91-3.99 (m, 3H), 3.78 (s, 3H), 3.56-3.66 (m, 4H), 3.46-3.55 (m, 2H), 2.19-2.23 (m, 2H).

Example 44 (R)-3-(1,1-dioxido-5-(2-(trifluoromethyl)-1H-benzo[d]imidazol-5-yl)-1,2,5-thiadiazolidin-2-yl)pyrrolidine-1-carbonitrile

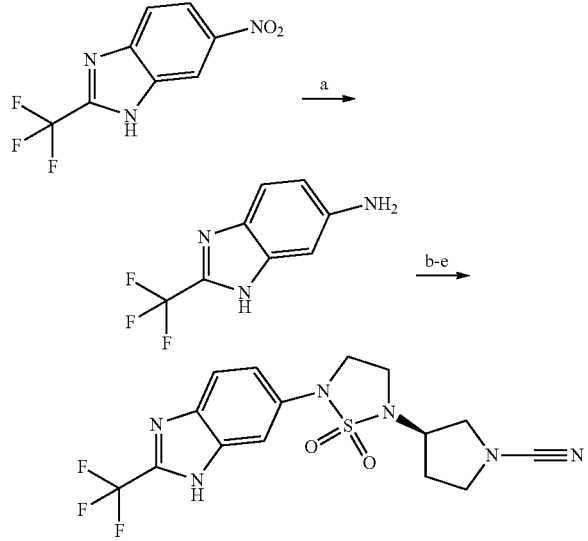

Step a. To a solution of 6-nitro-2-(trifluoromethyl)-1H-benzimidazole (1.00 g, 4.33 mmol) in THF (20 ml) was added 10% dry Pd/C (0.2 g) at rt. The reaction mixture was purged with $H_2$ gas at rt for 2 h. The resulting reaction mixture was carefully filtered through celite hyflow and concentrated under reduced pressure yielding 2-(trifluoromethyl)-1H-benzo[d]imidazol-5-amine (0.70 g, 3.48 mmol). This material was used directly for the next step without further purification. LCMS: Method C, 0.85 min, MS: ES+ 202.08; $^1$H NMR (400 MHz, DMSO-$d_6$) δ ppm 13.11 (br s, 1H), 7.35-7.42 (m, 1H), 6.60-6.71 (m, 2H), 5.25 (br s, 2H).

Steps b-e. The remainder of the synthesis followed a procedure similar to that described for Example 10, steps c-f. LCMS: Method A, 2.11 min, MS: ES+ 400.88; $^1$H NMR (80° C., 400 MHz, DMSO-d6) δ ppm 13.8 (br s, 1H), 7.22-7.79 (m, 3H), 3.92-4.03 (m, 3H), 3.42-3.67 (m, 6H), 2.17-2.28 (m, 2H).

Example 45 (R)-3-(1,1-dioxido-6-(2-(trifluoromethyl)-1H-benzo[d]imidazol-6-yl)-1,2,6-thiadiazinan-2-yl)pyrrolidine-1-carbonitrile

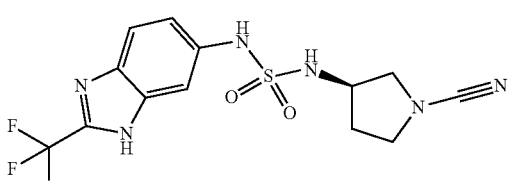

Prepared using a procedure similar to that described for Example 44 omitting step d. LCMS: Method B, 2.89 min, MS: ES+ 375.31; $^1$H NMR (60° C., 400 MHz, MeOD) δ ppm 7.66 (d, J=8.8 Hz, 1H), 7.61 (d, J=2 Hz, 1H), 7.27 (dd, J=2 Hz, 9.2 Hz, 1H), 3.97-4.02 (m, 1H), 3.30-3.55 (m, 3H), 3.20-3.24 (m, 1H), 2.03-2.14 (m, 1H), 1.80-1.89 (m, 1H).

Example 46 (R)-3-(1,1-dioxido-6-(2-(trifluoromethyl)-1H-benzo[d]imidazol-6-yl)-1,2,6-thiadiazinan-2-yl)pyrrolidine-1-carbonitrile Prepared using a procedure similar to that described for Example 44 using 1,3-dibromopropane in step d. LCMS: Method A, 2.33 min, MS: ES+ 414.99. $^1$H NMR (80° C., 400 MHz, DMSO-d6) δ ppm 13.85 (s, 1H), 7.70-7.80 (m, 2H), 7.40-7.43 (m, 1H), 4.31-4.35 (m, 1H), 3.50-3.84 (m, 8H), 2.24-2.88 (m, 1H), 2.09-2.18 (m, 1H), 1.90-1.97 (m, 2H).

Example 47 (S)-3-(1,1-dioxido-5-(3-(pyridin-2-yl)phenyl)-1,2,5-thiadiazolidin-2-yl)pyrrolidine-1-carbonitrile

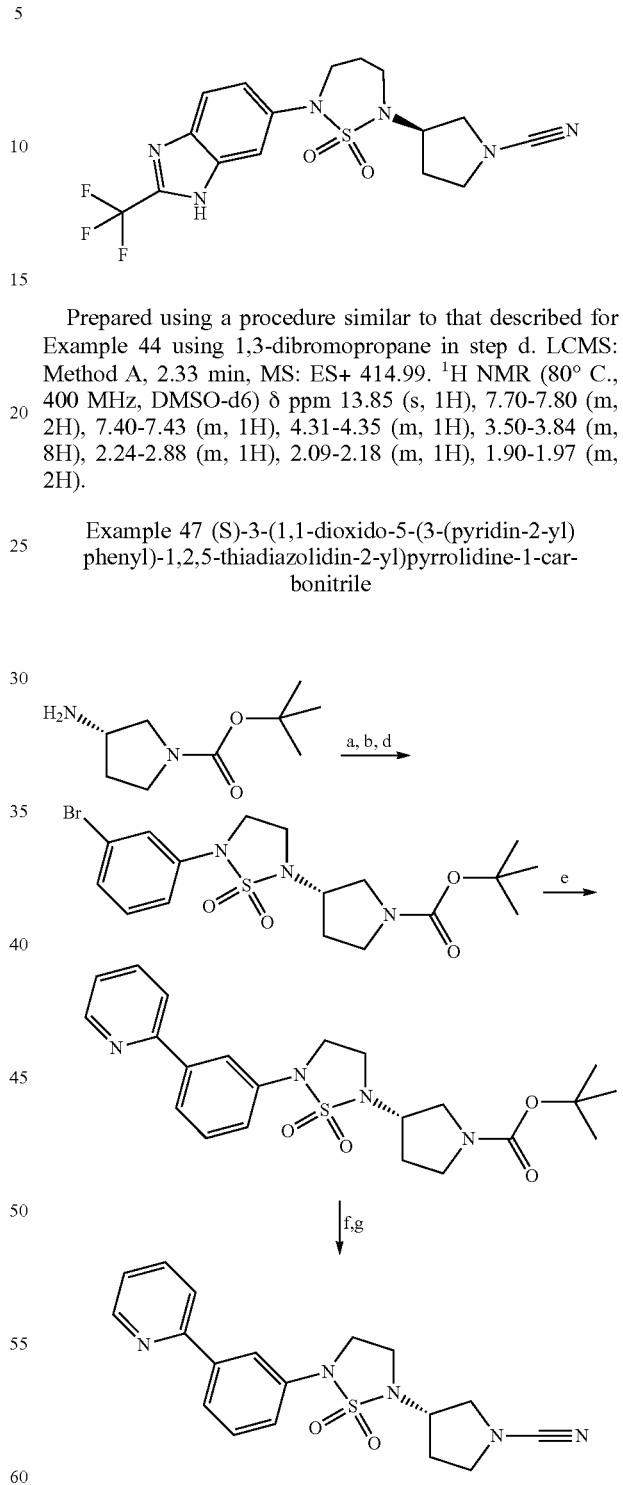

Steps a, b, d. Following a procedure similar to that described for Example 1, step a, b and d, using 3-bromoaniline in step b.

Step e. A solution of tert-butyl (S)-3-(5-(3-bromophenyl)-1,1-dioxido-1,2,5-thiadiazolidin-2-yl)pyrrolidine-1-carboxylate (0.3 g, 0.67 mmol) and 2-(tributylstannyl)pyridine (0.25 g, 0.67 mmol) in 1,4-dioxane (12 ml) was prepared in a glass tube at rt. The reaction mixture was degassed for 30 min before adding Pd(PPh₃)₄ (0.08 g, 0.067 mmol). The glass tube was sealed and subjected to heating 100° C. (external temperature) for 4 h. The resulting reaction mixture was poured in to water (100 ml) and extracted with EtOAc (3×50 ml). The combined organic phase was washed with brine (50 ml), dried over Na₂SO₄, filtered and concentrated under reduced pressure. The resulting residue was purified by column chromatography (100% EtOAc) yielding tert-butyl (S)-3-(1,1-dioxido-5-(3-(pyridin-2-yl)phenyl)-1,2,5-thiadiazolidin-2-yl)pyrrolidine-1-carboxylate (0.35 g, quantitative). LCMS: Method C, 2.31 min, MS: ES+ 445.65.

Steps f, g. The title compound was synthesised from the intermediate above using a procedure similar to that described for Example 1, steps e and f. LCMS: Method A, 3.90 min, MS: ES+ 369.9; ¹H NMR (400 MHz, DMSO-d6) δ ppm 8.70 (d, J=4.0 Hz, 1H), 8.00 (s, 1H), 7.97-7.98 (m, 1H), 7.89-7.94 (m, 1H), 7.86 (d, 8.4 Hz, 1H), 7.54 (t, J=8.0 Hz, 16 Hz, 1H), 7.38-7.41 (m, 1H), 7.32 (dd, J=1.2 Hz, 7.6 Hz, 1H), 3.94-4.00 (m, 3H), 3.59-3.66 (m, 4H), 3.44-3.55 (m, 2H), 2.16-2.23 (m, 2H).

Example 48 (S)-3-(1,1-dioxido-5-(3-(pyridin-3-yl)phenyl)-1,2,5-thiadiazolidin-2-yl)pyrrolidine-1-carbonitrile

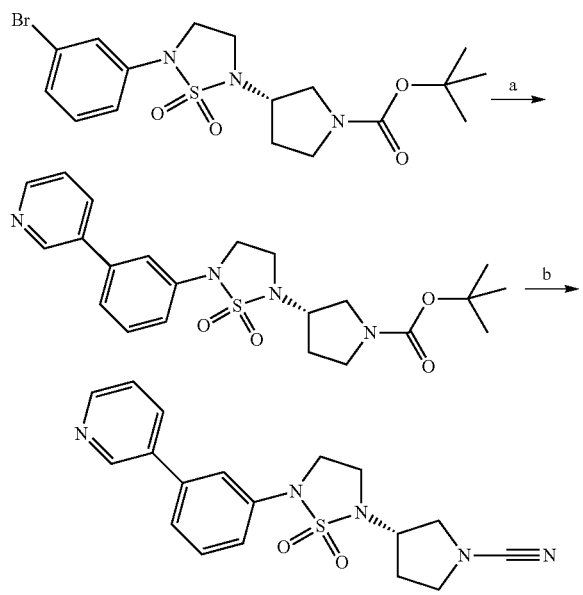

Step a. Following a procedure similar to that described for Example 10, step i, using tert-butyl (S)-3-(5-(3-bromophenyl)-1,1-dioxido-1,2,5-thiadiazolidin-2-yl)pyrrolidine-1-carboxylate from the synthesis of Example 47.

Step b. The title compound was synthesised from the intermediate above using a procedure similar to that described for Example 1, steps e and f. LCMS: Method A, 3.68 min, MS: ES+ 369.9; ¹H NMR (400 MHz, DMSO-d6) δ ppm 8.90 (d, J=1.6 Hz, 1H), 8.60 (dd, J=1.2 Hz, 4.4 Hz, 1H), 8.07-8.10 (m, 1H), 7.50-7.57 (m, 3H), 7.47 (s, 1H), 7.35 (dd, J=2.0 Hz, 7.2 Hz, 1H), 3.96-3.99 (m, 3H), 3.44-3.66 (m, 4H), 3.33-3.39 (m, 2H), 2.17-2.23 (m, 2H).

Example 49 (R)-3-(5-(9-methyl-9H-carbazol-3-yl)-1,1-dioxido-1,2,5-thiadiazolidin-2-yl)pyrrolidine-1-carbonitrile

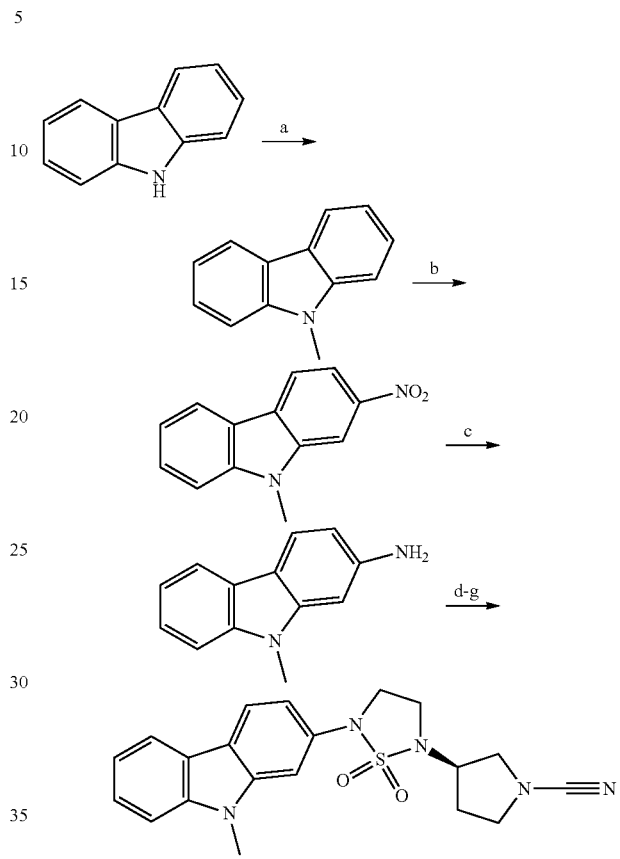

Step a. To a solution of carbazole (3.00 g, 17.96 mmol) in DMF (25 ml) was added NaH (1.72 g, 71.85 mmol) portion wise at 0° C. The reaction mixture was stirred at rt for 30 min. Methyl iodide (5.0 g, 35.92 mmol) was added to the reaction mixture at 0° C. The reaction mixture was stirred at rt for 2 h. The resulting reaction mixture was poured into water (100 ml) and the obtained solids were collected by filtration. The resulting solid was dried under vacuum yielding 9-methyl-9H-carbazole (3.3 g, quantitative). This material was used directly for the next step without further purification.

Step b. To a solution of 9-methyl-9H-carbazole (2.00 g, 11.05 mmol) in acetic acid (20 ml) was added HNO₃ (1.39 g, 22.10 mmol) at 0° C. The reaction mixture was stirred at rt for 16 h. The resulting reaction mixture was poured in to ice cold water (100 ml) and the obtained solids were collected by filtration. The resulting solid was dried under vacuum yielding 9-methyl-3-nitro-9H-carbazole (2.5 g, 11.06 mmol). LCMS: Method C, 2.40 min, MS: ES+ 227.14.

Step c. To a solution of 9-methyl-3-nitro-9H-carbazole (2.5 g, 11.06 mmol) in MeOH (30 ml) was added 10% dry Pd/C (1.0 g) at rt. The reaction mixture was purged with H₂ gas at rt for 3 h. The resulting reaction mixture was carefully filtered through celite hyflow, washed with EtOAc (30 ml) and concentrated under reduced pressure yielding 9-methyl-9H-carbazol-3-amine (2.00 g, 10.20 mmol). LCMS: Method C, 1.69 min, MS: ES+ 197.14.

Steps d-g. The title compound was synthesised from the intermediate above using a procedure similar to that described for Example 10, steps c-f. LCMS: Method B, 4.22 min, MS: ES+ 413.39 (M+18); ¹H NMR (400 MHz, DMSO-d6) δ ppm 8.19 (d, J=7.6 Hz, 1H), 8.13 (d, J=2.4 Hz, 1H), 7.63 (dd, J=8.8 Hz, J=17.2 Hz, 2H), 7.47-7.52 (m, 2H), 7.23 (dd, J=7.2 Hz, J=14.4 Hz, 1H), 3.94-4.00 (m, 3H), 3.89 (s, 3H), 3.51-3.72 (m, 5H), 3.33-3.49 (m, 1H), 2.17-2.25 (m, 2H).

Example 50 (R)-3-(5-(2-morpholinopyridin-4-yl)-1,1-dioxido-1,2,5-thiadiazolidin-2-yl)pyrrolidine-1-carbonitrile

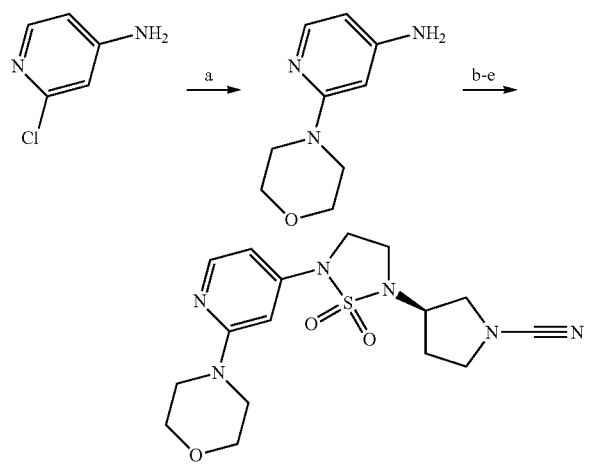

Step a. A neat mixture of 2-chloropyridin-4-amine (1.0 g, 7.81 mmol) in morpholine (1 ml) was heated at 170° C. for 16 h. The resulting mixture was poured into water (10 ml) and extracted with EtOAc (4×10 ml). The collected organic phase was dried over Na₂SO₄, filtered and concentrated under reduced pressure yielding 2-morpholinopyridin-4-amine (1.0 g, 5.5 mmol). This material was used directly for the next step without further purification. LCMS: Method C, 0.64 min, MS: ES+ 180.21.

Steps b-e. The title compound was synthesised from the intermediate above using a procedure similar to that described for Example 10, steps c-f. LCMS Method A, 3.31 min, MS: ES+ 378.99, ¹H NMR (400 MHz, DMSO-d6) δ ppm 8.04 (d, J=5.6 Hz, 1H), 6.57 (dd, J=2, 6 Hz, 1H), 6.35 (s, 1H), 3.93-4.05 (m, 1H), 3.89 (t, J=6.4 Hz, 2H), 3.69 (t, J=4.8 Hz, 4H), 3.56-3.64 (m, 5H), 3.42-3.54 (m, 5H), 2.15-2.24 (m, 2H).

Example 51 (R)-3-(5-(4-morpholinopyrimidin-2-yl)-1,1-dioxido-1,2,5-thiadiazolidin-2-yl)pyrrolidine-1-carbonitrile

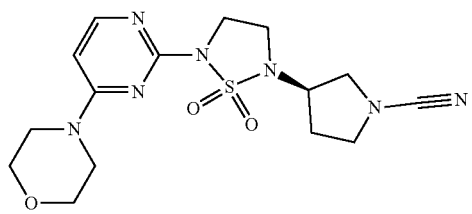 [SMILES: N#CN1CC[C@@H](N2CCN(c3nccc(N4CCOCC4)n3)S2(=O)=O)C1]

Prepared using a procedure similar to that described for Example 50 starting from 2-amino-4-chloropyrimidine. LCMS: Method B, 2.91 min, MS: ES+ 380.31. ¹H NMR (400 MHz, DMSO-d6) δ ppm 8.07 (d, J=6.0 Hz, 1H), 6.54 (d, J=6.0 Hz, 1H), 3.87-3.93 (m, 3H), 3.64 (t, J=4.8 Hz, 4H), 3.59 (d, J=6.0 Hz, 4H), 3.55 (t, J=2.8 Hz, 2H), 3.52 (t, J=5.6 Hz, 1H), 3.41-3.49 (m, 3H), 2.11-2.20 (m, 2H).

Example 52 (R)-3-(5-(2-(4-methylpiperazin-1-yl)pyridin-4-yl)-1,1-dioxido-1,2,5-thiadiazolidin-2-yl)pyrrolidine-1-carbonitrile

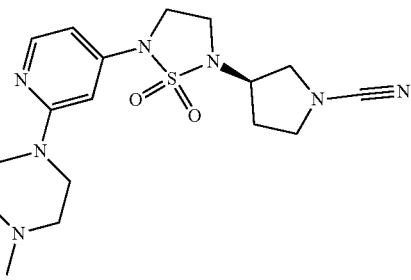

Synthesised using a procedure similar to that described for Example 50 starting from 1-methylpiperazine. LCMS: Method A, 3.23 min, MS: ES+ 392.10. ¹H NMR (400 MHz, DMSO-d6) δ ppm 8.01 (d, J=5.6 Hz, 1H), 6.53 (dd, J=1.6 Hz, J=5.6 Hz, 1H), 6.34 (d, J=2.0 Hz, 1H), 3.95-3.98 (m, 1H), 3.88 (t, J=6.0 Hz, 2H), 3.53-3.64 (m, 5H), 3.42-3.49 (m, 5H), 2.39 (s, 4H), 2.15-2.21 (m, 5H).

Example 53 (R)-3-(5-(3-((R)-3-methoxypyrrolidin-1-yl)phenyl)-1,1-dioxido-1,2,5-thiadiazolidin-2-yl)pyrrolidine-1-carbonitrile

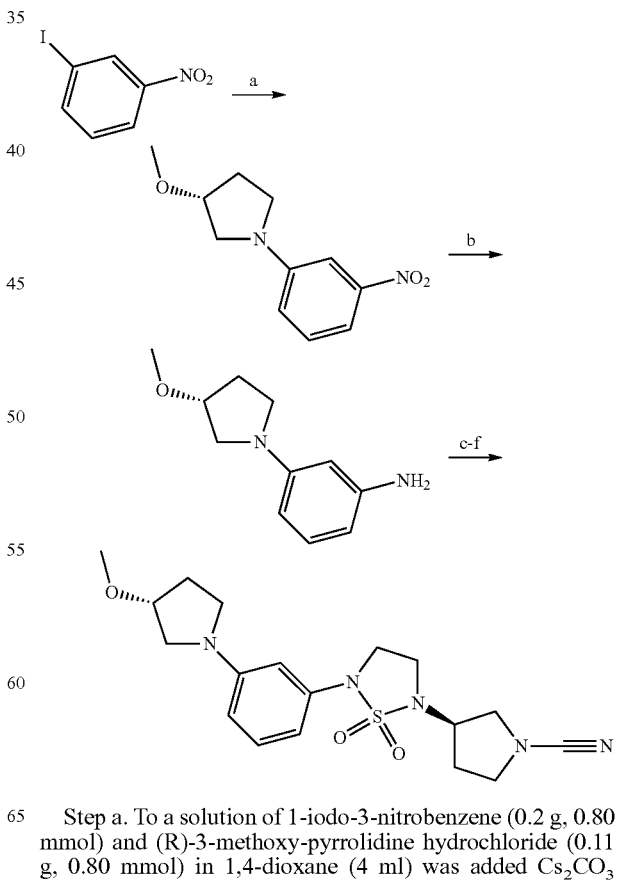

Step a. To a solution of 1-iodo-3-nitrobenzene (0.2 g, 0.80 mmol) and (R)-3-methoxy-pyrrolidine hydrochloride (0.11 g, 0.80 mmol) in 1,4-dioxane (4 ml) was added Cs₂CO₃

(0.65 g, 2.0 mmol) at rt. The reaction mixture was degassed for 10 min before adding Pd$_2$(dba)$_3$ (0.037 g, 0.04 mmol) and Xantphos (0.023 g, 0.04 mmol) and then heating at 110° C. for 16 h. The resulting mixture was poured into water (40 ml) and extracted with EtOAc (2×15 ml). The combined organic phase was collected, dried over Na$_2$SO$_4$, filtered and concentrated under reduced pressure to yielding (R)-3-methoxy-1-(3-nitrophenyl)pyrrolidine (0.2 g, quantitative). This material was used directly for the next step without further purification. LCMS: Method C, 2.24 min, MS: ES+ 223.16.

Step b. To a solution of (R)-3-methoxy-1-(3-nitrophenyl)pyrrolidine (0.2 g, 0.90 mmol) in methanol (5 ml) was added 10% Pd/C (dry basis) (0.02 g) at rt. The reaction mixture was purged with H$_2$ gas at rt for 1 h. The resulting reaction mixture was carefully filtered through celite hyflow and concentrated under reduced pressure to yielding (R)-3-(3-methoxypyrrolidin-1-yl) aniline (0.11 g, 0.57 mmol). This material was used directly for the next step without further purification. LCMS: Method C, 1.56 min, MS: ES+ 193.17.

Steps c-f. The title compound was synthesised from the intermediate above using a procedure similar to that described for Example 10, steps c-f. LCMS: Method A, 4.20 min, MS: ES+ 392.0; $^1$H NMR (400 MHz, DMSO-d6) δ ppm 7.16 (t, J=8 Hz, 1H), 6.5 (dd, J=1.2 Hz, 7.6 Hz, 1H), 6.33-6.36 (m, 2H), 4.06-4.09 (m, 1H), 3.89-3.95 (m, 1H), 3.86-3.78 (m, 2H), 3.59-3.63 (m, 2H), 3.45-3.58 (m, 5H), 3.21-3.36 (m, 6H), 2.14-2.22 (m, 2H), 2.04-2.08 (m, 2H).

Example 54 (R)-3-(5-(2-((R)-3-methoxypyrrolidin-1-yl)pyridin-4-yl)-1,1-dioxido-1,2,5-thiadiazolidin-2-yl)pyrrolidine-1-carbonitrile

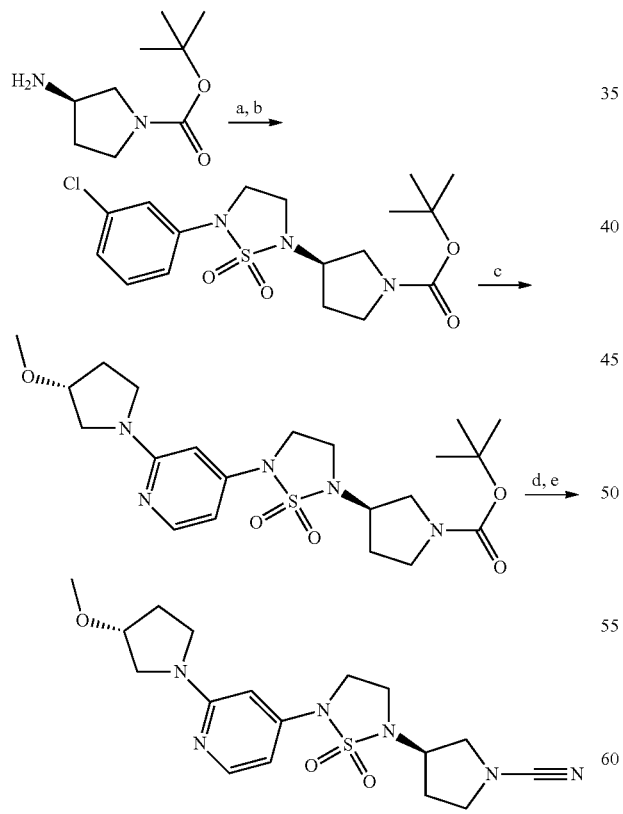

Steps a, b. Following a procedure similar to that described for Example 10, steps c and d, starting with 2-chloropyridin-4-amine.

Step c. To a solution of tert-butyl (R)-3-(5-(2-chloropyridin-4-yl)-1,1-dioxido-1,2,5-thiadiazolidin-2-yl)pyrrolidine-1-carboxylate (0.10 g, 0.24 mmol) in toluene (3 ml) was added (R)-3-methoxy-pyrrolidine hydrochloride (0.07 g, 0.50 mmol) at rt. NaOtBu (0.04 g, 0.49 mmol) and RuPhose (0.01 g, 0.02 mmol) was added in to reaction mixture and degassed for 15 min. Pd$_2$(dba)$_3$ (0.02 g, 0.02 mmol) was added in to reaction mixture and heated at 110° C. for 48 hrs. The resulting reaction mixture was poured into water (50 ml) and extracted with EtOAc (3×15 ml). The combined organic layer was washed with brine solution (50 ml). The organic phase was collected, dried over Na$_2$SO$_4$, filtered and concentrated under reduced pressure. The resulting residue was purified by column chromatography (5% MeOH in DCM) yielding tert-butyl (R)-3-(5-(2-((R)-3-methoxypyrrolidin-1-yl)pyridin-4-yl)-1,1-dioxido-1,2,5-thiadiazolidin-2-yl)pyrrolidine-1-carboxylate (0.20 g, quantitative). LCMS: Method C, 1.87 min, MS: ES+ 468.61.

Steps d, e. The title compound was synthesised from the intermediate above using a procedure similar to that described for Example 10, steps e and f. LCMS: Method A, 3.30 min, MS: ES+ 393.09; $^1$H NMR (400 MHz, DMSO-d6) δ ppm 7.97 (d, J=5.6 Hz, 1H), 6.47 (d, J=4.8 Hz, 1H), 6.01 (s, 1H), 4.06-4.07 (m, 1H), 3.90-3.96 (m, 1H), 3.87-3.91 (m, 2H), 3.54-3.64 (m, 5H), 3.43-3.53 (m, 5H), 3.26 (s, 3H), 2.15-2.21 (m, 2H), 2.02-2.05 (m, 2H).

Example 55 (R)-3-(5-(2-(3-methoxyazetidin-1-yl)pyridin-4-yl)-1,1-dioxido-1,2,5-thiadiazolidin-2-yl)pyrrolidine-1-carbonitrile

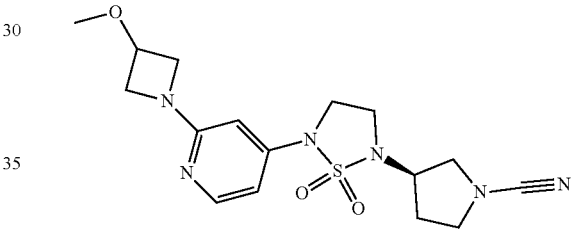

Synthesised using a procedure similar to that described for Example 54, using 3-methoxyazetidine hydrochloride in step c. LCMS: Method A, 3.24 min, MS: ES+ 379.05; $^1$H NMR (400 MHz, DMSO-d6) δ ppm 7.97 (d, J=6 Hz, 1H), 6.50 (d, J=7.6 Hz, 1H), 5.95 (s, 1H), 4.28-4.35 (m, 1H), 4.10-4.14 (m, 2H), 3.95-3.98 (m, 1H), 3.84-3.87 (m, 2H), 3.70-3.74 (m, 2H), 3.44-3.64 (m, 6H), 3.24 (s, 3H), 2.14-2.21 (m, 2H).

Example 56 (R)-3-(5-(2-(bis(2-methoxyethyl)amino)pyridin-4-yl)-1,1-dioxido-1,2,5-thiadiazolidin-2-yl)pyrrolidine-1-carbonitrile

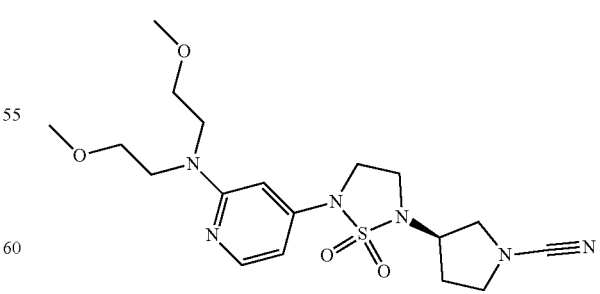

Synthesised using a procedure similar to that described for Example 54, using bis(2-methoxyethyl) amine in step c. LCMS: Method B, 2.88 min, MS: ES+ 425.35; $^1$H NMR (400 MHz, DMSO-d6) δ ppm 7.96 (d, J=6 Hz, 1H), 6.43 (dd, J=1.6 Hz, J=5.6 Hz, 1H), 6.22 (s, 1H), 3.95-3.98 (m, 1H), 3.86 (t, J=6 Hz, 2H), 3.62-3.65 (m, 4H), 3.53-3.60 (m, 4H), 3.42-3.51 (m, 6H), 3.25 (s, 6H), 2.15-2.21 (m, 2H).

Example 57 N-biphenyl-3-yl-N'-(1-cyanopyrrolidin-3-yl)sulfuric diamide

Synthesis According to Scheme 1 Steps c, e, f.

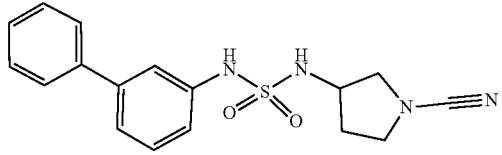 [SMILES: N#CN1CCC(NS(=O)(=O)Nc2cccc(-c3ccccc3)c2)C1]

Step c. To a solution of 3-phenylaniline (0.2 g, 1.18 mmol) in DCM (5 ml) was added imidazole (0.24 g, 3.55 mmol) at −78° C. and stirred for 5 min. $SO_2Cl_2$ (0.16 g, 1.18 mmol) was added drop wise to the reaction mixture and stirred for a further 20 min at −78° C. Precipitation of white solid was observed. Tert-butyl 3-aminopyrrolidine-1-carboxylate (0.22 g, 1.18 mmol) was added to the reaction mixture at −78° C. The reaction mixture was allowed to warm at rt and it was then heated at 80° C. for 1 hr. The resulting reaction mixture was poured into water (50 ml) and extracted with EtOAc (2×50 ml). The combined organic layer was washed with citric acid solution (50 ml). The organic phase was collected, dried over $Na_2SO_4$, filtered and concentrated under reduced pressure. The resulting residue was purified by column chromatography (25% EtOAc in Hexane) yielding tert-butyl 3-((N-([1,1'-biphenyl]-3-yl)sulfamoyl)amino)pyrrolidine-1-carboxylate (0.16 g, 0.38 mmol), LCMS: Method C, 2.32 min, MS: ES-416.38.

Steps e, f. The remainder of the synthesis followed a procedure similar to that described for Example 1 steps e and f. LCMS: Method B, 3.95 min, MS: ES+ 343.4; $^1$H NMR (400 MHz, DMSO-$d_6$) δ ppm 1H NMR (400 MHz, DMSO-d6) δ ppm 9.94 (s, 1H), 8.05 (d, J=6.8 Hz, 1H), 7.62 (d, J=7.6 Hz, 2H), 7.48 (t, J=7.6 Hz, 15.2 Hz, 2H), 7.43 (s, 1H), 7.41-7.43 (m, 2H), 7.30 (d, J=8.0 Hz 1H), 7.14 (d, J=7.2 Hz, 1H), 3.82-3.86 (m, 1H), 3.46-3.50 (m, 1H), 3.31-3.37 (m, 2H), 3.10-3.13 (m, 1H), 1.95-2.00 (m, 1H), 1.70-1.75 (m, 1H).

Example 58 N-biphenyl-4-yl-N'-(1-cyanopyrrolidin-3-yl)sulfuric diamide

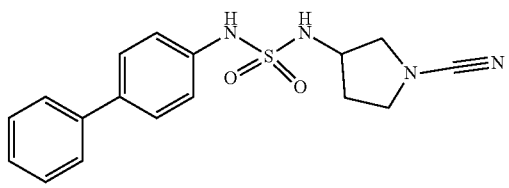 [SMILES: N#CN1CCC(NS(=O)(=O)Nc2ccc(-c3ccccc3)cc2)C1]

Synthesised using a procedure similar to that described for Example 57, using [1,1'-biphenyl]-4-amine. LCMS: Method A, 3.58 min, MS: ES+ 343.1; $^1$H NMR (400 MHz, DMSO-d6) δ ppm 9.33 (s, 1H), 7.99 (d, J=6.4 Hz, 1H), 7.61-7.64 (m, 4H), 7.44 (t, J=8.0 Hz, 16.0 Hz, 2H), 7.33 (t, J=7.2 Hz, 10.8 Hz, 1H), 7.25 (d, J=7.2 Hz, 2H), 3.82-3.86 (m, 1H), 3.47-3.51 (m, 1H), 3.31-3.39 (m, 2H), 3.10-3.14 (m, 1H), 1.95-2.03 (m, 1H), 1.70-1.78 (m, 1H).

Example 59 N-(1-cyanopyrrolidin-3-yl)-4-phenylpiperidine-1-sulfonamide

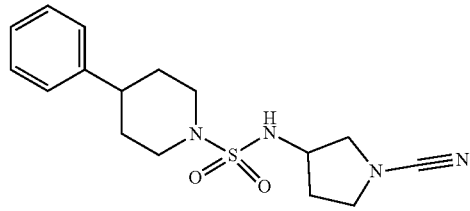 [SMILES: N#CN1CCC(NS(=O)(=O)N2CCC(c3ccccc3)CC2)C1]

Synthesised using a procedure similar to that described for Example 57, using 4-phenylpiperidine. LCMS: Method A, 4.40 min, MS: ES+ 335.10; $^1$H NMR (400 MHz, DMSO-d6) δ ppm 7.67 (d, J=6.4 Hz, 1H), 7.25-7.33 (m, 4H), 7.19-7.22 (m, 1H), 3.85-3.90 (m, 1H), 3.62 (d, J=12 Hz, 2H), 3.55-3.57 (m, 1H), 3.43-3.49 (m, 1H), 3.37-3.41 (m, 1H), 3.24-3.28 (m, 1H), 2.76 (t, J=7.6 Hz, 23.6 Hz, 2H), 2.65 (t, J=12 Hz, 24, Hz, 1H), 2.06-2.19 (m, 1H), 1.83-1.89 (m, 3H), 1.67-1.71 (m, 2H).

Example 60 N-(1-cyanopyrrolidin-3-yl)-4-phenylpiperazine-1-sulfonamide

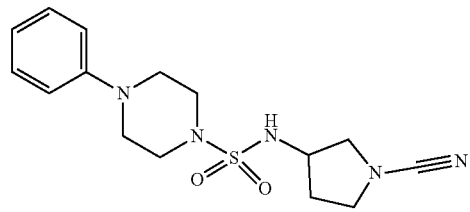 [SMILES: N#CN1CCC(NS(=O)(=O)N2CCN(c3ccccc3)CC2)C1]

Synthesised using a procedure similar to that described for Example 57, using 1-phenylpiperazine.

LCMS: Method A, 3.92 min, MS: ES+ 336.09; $^1$H NMR (400 MHz, DMSO-d6) δ ppm 7.80 (d, J=6.4 Hz, 1H), 7.22-7.26 (m, 2H), 6.97 (d, J=8 Hz, 2H), 6.82 (t, 7.2 Hz, 14.8 Hz, 1H), 3.87-3.91 (m, 1H), 3.34-3.56 (m, 3H), 3.17-3.27 (m, 9H), 2.03-2.10 (m, 1H), 1.84-1.90 (m, 1H).

Example 61 N-(1-cyanopyrrolidin-3-yl)indoline-1-sulfonamide

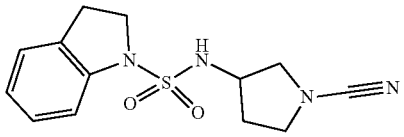 [SMILES: N#CN1CCC(NS(=O)(=O)N2CCc3ccccc32)C1]

Synthesised using a procedure similar to that described for Example 57, using indoline. LCMS: Method C, 2.00 min, MS: ES+ 293.47; $^1$H NMR (400 MHz, DMSO-d6) δ ppm 7.80 (d, J=6.4 Hz, 1H), 7.22-7.26 (m, 2H), 6.97 (d, J=8 Hz, 2H), 6.82 (t, 7.2 Hz, 14.8 Hz, 1H), 3.87-3.91 (m, 1H), 3.34-3.56 (m, 3H), 3.17-3.27 (m, 9H), 2.03-2.10 (m, 1H), 1.84-1.90 (m, 1H).

Example 62 (R)—N-(1-cyanopyrrolidin-3-yl)-3,4-dihydroisoquinoline-2(1H)-sulfonamide

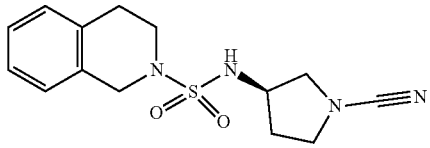 [SMILES: N#CN1CC[C@@H](NS(=O)(=O)N2CCc3ccccc3C2)C1]

Synthesised using a procedure similar to that described for Example 57, using 1,2,3,4-tetrahydroisoquinoline. LCMS: Method A, 3.95 min, MS: ES+ 306.93; $^1$H NMR (400 MHz, DMSO-d6) δ ppm 7.82 (d, J=6.4 Hz, 1H), 7.15-7.20 (m, 4H), 4.29 (s, 2H), 3.83-3.87 (m, 1H), 3.33-3.51 (m, 5H), 3.19-3.23 (m, 1H), 2.89 (t, J=11.6 Hz, 2H), 1.99-2.04 (m, 1H), 1.80-1.85 (m, 1H).

Example 63 (R)—N-(1-cyanopyrrolidin-3-yl)-5-phenylindoline-1-sulfonamide

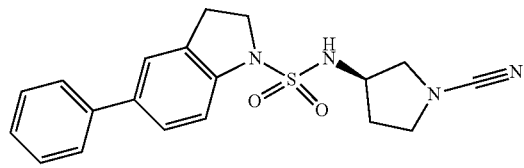 [SMILES: N#CN1CC[C@@H](NS(=O)(=O)N2CCc3cc(-c4ccccc4)ccc32)C1]

Synthesised using a procedure similar to that described for Example 57, using 5-phenyl-2,3-dihydro-1H-indole. LCMS: Method B, 4.48 min, MS: ES+ 369.35; $^1$H NMR (400 MHz, DMSO-d6) δ ppm 8.31 (d, J=6.8 Hz, 1H), 7.62 (d, J=7.6 Hz, 2H), 7.55 (s, 1H), 7.41-7.49 (m, 3H), 7.30-7.35 (m, 2H), 3.85-3.95 (m, 3H), 3.30-3.45 (m, 3H), 3.10-3.19 (m, 3H), 1.92-1.97 (m, 1H), 1.72-1.77 (m, 1H).

Example 64 (R)—N-(1-cyanopyrrolidin-3-yl)-4-phenylindoline-1-sulfonamide

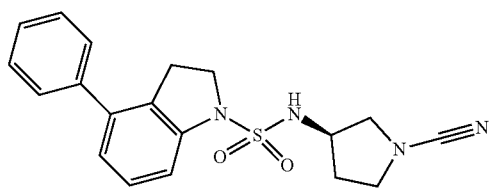 [SMILES: N#CN1CC[C@@H](NS(=O)(=O)N2CCc3c(-c4ccccc4)cccc32)C1]

Synthesised using a procedure similar to that described for Example 57, using 4-phenyl-2,3-dihydro-1H-indole. LCMS: Method A, 4.61 min, MS: ES+ 368.94; $^1$H NMR (400 MHz, DMSO-d6) δ ppm 8.29 (br s, 1H), 7.44-7.49 (m, 4H), 7.36-7.42 (m, 1H), 7.26-7.32 (m, 2H), 7.32 (dd, J=1.6 Hz, 6.8 Hz, 1H), 3.85-3.92 (m, 3H), 3.28-3.46 (m, 3H), 3.08-3.21 (m, 3H), 1.92-2.00 (m, 1H), 1.72-1.80 (m, 1H).

Example 65 (R)—N-(1-cyanopyrrolidin-3-yl)-6-methoxy-3,4-dihydroisoquinoline-2(1H)-sulfonamide

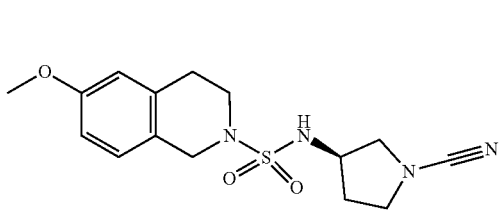 [SMILES: COc1ccc2c(c1)CCN(S(=O)(=O)N[C@@H]1CCN(C#N)C1)C2]

Synthesised using a procedure similar to that described for Example 57, using 6-methoxy-1,2,3,4-tetrahydroisoquinoline. LCMS: Method A, 3.87 min, MS: ES+ 337.00; $^1$H NMR (400 MHz, DMSO-d6) δ ppm 7.79 (d, J=6.8 Hz, 1H), 7.08 (d, J=8 Hz, 1H), 6.73-6.81 (m, 2H), 4.21 (s, 2H), 3.80-3.90 (m, 1H), 3.72 (s, 3H), 3.46-3.62 (m, 2H), 3.34-3.39 (m, 3H), 3.19-3.22 (m, 1H), 2.86 (t, J=6 Hz, 2H), 1.97-2.06 (m, 1H), 1.79-1.86 (m, 1H).

Example 66 (R)-3-(3-methyl-2,2-dioxidobenzo[c][1,2,5]thiadiazol-1(3H)-yl)pyrrolidine-1-carbonitrile

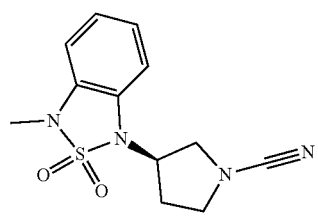 [SMILES: CN1c2ccccc2N([C@@H]2CCN(C#N)C2)S1(=O)=O]

Synthesis According to Scheme 2 Steps a-f.

Step a. To a solution of (R)-1-Boc-3-aminopyrrolidine (3.90 g, 21.28 mmol) in DMF (50 ml) was added K$_2$CO$_3$ (8.80 g, 63.83 mmol) at rt. The reaction mixture was stirred for 20 min and then treated with 1-fluoro-2-nitrobenzene (3.00 g, 21.28 mmol). The reaction mixture was heated at 80° C. for 16 h. The resulting reaction mixture was poured into water (500 ml) and extracted with EtOAc (2×200 ml). The combined organic phase was collected, dried over Na$_2$SO$_4$, filtered and concentrated under reduced pressure yielding tert-butyl (R)-3-((2-nitrophenyl)amino) pyrrolidine-1-carboxylate (8.00 g, quantitative). This material was used directly for the next step without further purification. LCMS: Method C, 2.37 min, MS: ES+ 252.1 (M−56).

Step b. To a solution of tert-butyl (R)-3-((2-nitrophenyl)amino)-pyrrolidine-1-carboxylate (8.00 g, 26.04 mmol) in ethanol (50 ml) was added 10% dry Pd/C (2.0 g) at rt. The reaction mixture was purged with H$_2$ gas at rt for 16 h. The resulting reaction mixture was carefully filtered through celite hyflow and concentrated under reduced pressure yielding tert-butyl (R)-3-((2-aminophenyl)amino)pyrrolidine-1-carboxylate (2.70 g, 9.74 mmol). This material was used directly for the next step without further purification. LCMS: Method C, 1.92 min, MS: ES+ 278.2.

Step c. To a solution of tert-butyl (R)-3-((2-aminophenyl)amino)pyrrolidine-1-carboxylate (0.5 g, 1.80 mmol) in pyridine (10 ml) was added sulfamide (1.20 g, 12.62 mmol) at rt. The reaction mixture was heated at 100° C. for 16 h. The resulting reaction mixture was combined with 3 other batches on the same scale, prepared by an identical method. The resulting reaction mixture was concentrated under reduced pressure. The obtained residue was quickly poured into water (500 ml) and acidified with citric acid solution (50 ml). The resulting acidic aqueous was extracted with EtOAc (3×200 ml). The combined organic phase was collected, dried over $Na_2SO_4$, filtered and concentrated under reduced pressure. The resulting residue was purified by column chromatography (25% EtOAc in hexane) yielding a tert-butyl (R)-3-(2,2-dioxidobenzo[c][1,2,5]thiadiazol-1(3H)-yl) pyrrolidine-1-carboxylate (0.11 g, 0.32 mmol). LCMS: Method C, 2.21 min, MS: ES-338.34.

Step d. To a solution of tert-butyl (R)-3-(2,2-dioxidobenzo[c][1,2,5]thiadiazol-1(3H)-yl)pyrrolidine-1-carboxylate (0.10 g, 0.29 mmol) in THF (10 ml) was added NaH (0.035 g, 1.47 mmol) at 0° C. The reaction mixture was stirred at rt for 20 min. Methyl iodide (0.02 ml, 0.44 mmol) was added to the reaction mixture at 0° C. The reaction mixture was heated at 80° C. for 1 h. The resulting reaction mixture was poured into water (100 ml) and extracted with EtOAc (2×50 ml). The combined organic layer was collected, dried over $Na_2SO_4$, filtered and concentrated under reduced pressure to afford tert-butyl (R)-3-(3-methyl-2,2-dioxidobenzo[c][1,2,5]thiadiazol-1(3H)-yl)pyrrolidine-1-carboxylate (0.15 g, quantitative). This material was used directly for the next step without further purification. LCMS: Method C, 2.40 min, MS: ES+ 354.3.

Steps e, f. The title compound was synthesised from the intermediate above using a procedure similar to that described for steps e and f of Example 1. LCMS: Method B, 3.64 min, MS: ES+ 279.2. $^1$H NMR (400 MHz, DMSO-d6) δ ppm 7.10-7.13 (m, 1H), 7.02-7.07 (m, 3H), 4.83-4.88 (m, 1H), 3.86 (q, J=7.6 Hz, 1H), 3.62-3.71 (m, 2H), 3.50 (t, J=7.6 Hz, 1H), 3.22 (s, 3H), 2.34-2.46 (m, 2H).

Example 67 (R)-3-(3-benzyl-2,2-dioxidobenzo[c][1,2,5]thiadiazol-1(3H)-yl)pyrrolidine-1-carbonitrile

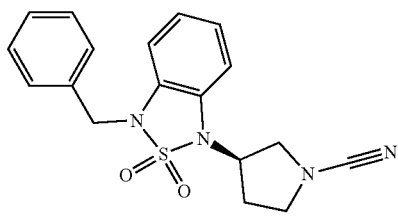 [SMILES: N#CN1CC[C@@H](N2c3ccccc3N(Cc3ccccc3)S2(=O)=O)C1]

Synthesised using a procedure similar to that described for Example 66, using benzyl bromide in step d. LCMS: Method B, 4.42 min, MS: ES+ 355.0. $^1$H NMR (400 MHz, DMSO-d6) δ ppm 7.44 (d, J=6.8 Hz, 2H), 7.39 (dd, J=2.0 Hz, J=7.2 Hz, 2H), 7.29-7.33 (m, 1H), 7.13 (dd, J=1.2 Hz, J=8.0 Hz, 1H), 6.93-7.03 (m, 2H), 6.82 (dd, J=1.2 Hz, J=7.6 Hz, 1H), 4.98 (s, 2H), 4.87-4.95 (m, 1H), 3.88 (q, J=7.6 Hz, 1H), 3.65-3.73 (m, 2H), 3.50 (q, J=8.0 Hz, 1H), 2.32-2.47 (m, 2H).

Example 68 (R)-3-(2,2-dioxido-3-(pyridin-3-ylmethyl)benzo[c][1,2,5]thiadiazol-1(3H)-yl)pyrrolidine-1-carbonitrile

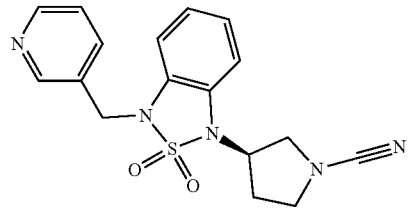 [SMILES: N#CN1CC[C@@H](N2c3ccccc3N(Cc3cccnc3)S2(=O)=O)C1]

Synthesised using a procedure similar to that described for Example 66, using 3-(bromomethyl)-pyridine in step d. LCMS: Method B, 3.17 min, MS: ES+ 356.35. H NMR (400 MHz, DMSO-d6) δ ppm 8.67 (d, J=2.0 Hz, 1H), 8.52 (dd, J=1.6 Hz, J=4.8 Hz, 1H), 7.80-7.83 (m, 1H), 7.42 (dd, J=4.8 Hz, J=8.0 Hz, 1H), 7.14 (t, J=1.2 Hz, 1H), 6.94-7.05 (m, 3H), 5.07 (s, 2H), 4.87-4.94 (m, 1H), 3.88 (q, J=7.6 Hz, 1H), 3.65-3.73 (m, 2H), 3.48 (q, J=7.6 Hz, 1H), 2.33-2.46 (m, 2H).

Example 69 (R)-3-(1-benzyl-2,2-dioxido-1,4-dihydro-3H-benzo[c][1,2,6]thiadiazin-3-yl)pyrrolidine-1-carbonitrile

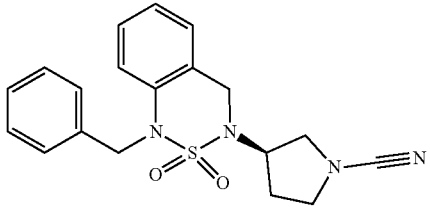 [SMILES: N#CN1CC[C@@H](N2Cc3ccccc3N(Cc3ccccc3)S2(=O)=O)C1]

Synthesis According to Scheme 3 Steps a, b, d-g.

Step a. A solution of (R)-1-Boc-3-aminopyrrolidine (2.00 g, 10.75 mmol) and 2-nitrobenzaldehyde (1.62 g, 10.75 mmol) in MeOH (20 ml) was stirred at rt for 5 hr. Sodium borohydride (0.406 g, 10.75 mmol) was added to the reaction mixture at 0° C. The reaction mixture was stirred at rt for overnight. The mixture was concentrated under reduced pressure and the resulting residue was purified by column chromatography (35% EtOAc in hexane) yielding a tert-butyl (R)-3-((2-nitrobenzyl)amino)pyrrolidine-1-carboxylate (1.6 g, 4.98 mmol). LCMS: Method C, 1.72 min, MS: ES+ 322.4.

Step b. To a solution of tert-butyl (R)-3-((2-nitrobenzyl)amino)pyrrolidine-1-carboxylate (0.20 g, 0.62 mmol) in MeOH (10 ml) was added 10% dry Pd/C (0.02 g) at rt. The reaction mixture was purged with $H_2$ gas at rt for 3 h. The resulting reaction mixture was carefully filtered through celite hyflow and concentrated under reduced pressure yielding tert-butyl (R)-3-((2-aminobenzyl)amino)pyrrolidine-1-carboxylate (0.15 g, 0.51 mmol). This material was used directly for the next step without further purification. LCMS: Method C, 1.69 min, MS: ES+ 292.3.

Step d. To a solution of tert-butyl (R)-3-((2-aminobenzyl)amino)pyrrolidine-1-carboxylate (0.15 g, 0.51 mmol) in pyridine (10 ml) was added sulfamide (0.494 g, 5.15 mmol) at rt. The reaction mixture was heated at 110° C. for 5 h. The resulting reaction mixture was concentrated under reduced pressure. The resulting residue was purified by column chromatography (45% EtOAc in hexane) yielding a tert-butyl (R)-3-(2,2-dioxido-1,4-dihydro-3H-benzo[c][1,2,6]thiadiazin-3-yl)pyrrolidine-1-carboxylate (0.10 g, 0.28 mmol). LCMS: Method C, 2.26 min, MS: ES+ 354.5.

Step e. To a solution of tert-butyl (R)-3-(2,2-dioxido-1,4-dihydro-3H-benzo[c][1,2,6]thiadiazin-3-yl)pyrrolidine-1-carboxylate (0.10 g, 0.28 mmol) in THF (5 ml) was added NaH (0.041 g, 1.70 mmol) at 0° C. The reaction mixture was stirred at rt for 1 h. Benzyl bromide (0.07 g, 0.42 mmol) was added to the reaction mixture at rt. The reaction mixture was heated at 50° C. for overnight. The resulting reaction mixture was poured into saturated NaHCO₃ solution (20 ml) and extracted with EtOAc (4×10 ml). The combined organic layer was collected, dried over Na₂SO₄, filtered and concentrated under reduced pressure. The resulting residue was purified by column chromatography (10% EtOAc in hexane) yielding tert-butyl (R)-3-(1-benzyl-2,2-dioxido-1,4-dihydro-3H-benzo[c][1,2,6]thiadiazin-3-yl)pyrrolidine-1-carboxylate (0.06 g, 0.135 mmol). LCMS: Method C, 2.73 min, MS: ES+ 444.5.

Steps f, g. The title compound was synthesised from the intermediate above using a procedure similar to that described for steps e and f of Example 1. LCMS: Method B, 4.50 min, MS: ES+ 369.6. ¹H NMR (400 MHz, DMSO-d6) δ ppm 7.36-7.43 (m, 4H), 7.29 (t, J=7.2 Hz, 1H), 7.19-7.25 (m, 2H), 7.05 (t, J=6.8 Hz, 1H), 6.84 (d, J=8.4 Hz, 1H), 5.03 (s, 2H), 4.80 (s, 2H), 4.18-4.23 (m, 1H), 3.41-3.47 (m, 2H), 3.29-3.33 (m, 2H), 1.88-2.00 (m, 2H).

Example 70 (R)-3-(1-methyl-2,2-dioxido-1,4-dihydro-3H-benzo[c][1,2,6]thiadiazin-3-yl)pyrrolidine-1-carbonitrile

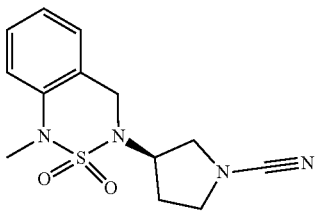 [SMILES: CN1c2ccccc2CN([C@@H]2CCN(C#N)C2)S1(=O)=O]

Synthesised using a procedure similar to that described for Example 69, using methyl iodide in step e. LCMS: Method B, 4.42 min, MS: ES+ 355.0. ¹H NMR (400 MHz, DMSO-d6) δ ppm 7.44 (d, J=6.8 Hz, 2H), 7.39 (dd, J=2.0 Hz, J=7.2 Hz, 2H), 7.29-7.33 (m, 1H), 7.13 (dd, J=1.2 Hz, J=8.0 Hz, 1H), 6.93-7.03 (m, 2H), 6.82 (dd, J=1.2 Hz, J=7.6 Hz, 1H), 4.98 (s, 2H), 4.87-4.95 (m, 1H), 3.88 (q, J=7.6 Hz, 1H), 3.65-3.73 (m, 2H), 3.50 (q, J=8.0 Hz, 1H), 2.32-2.47 (m, 2H).

Example 71 (R)-3-(7-(1-methyl-1H-pyrazol-4-yl)-2,2-dioxido-1,4-dihydro-3H-benzo[c][1,2,6]thiadiazin-3-yl)pyrrolidine-1-carbonitrile

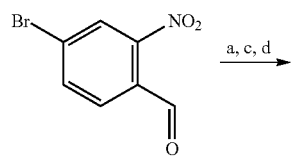

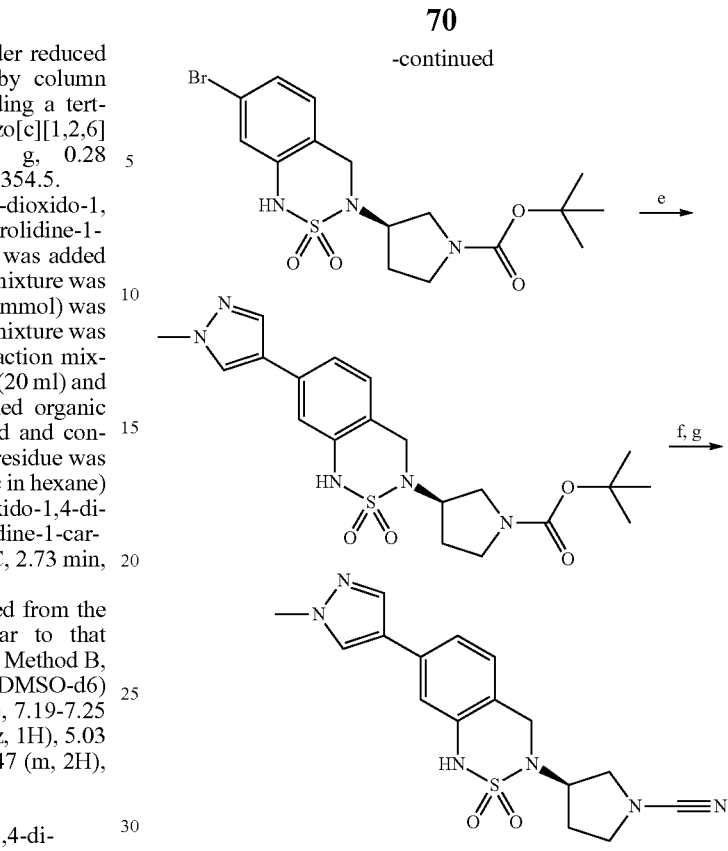

The first three steps were conducted according to General Scheme 3, steps a, c, d.

Step a. A solution of (R)-1-Boc-3-aminopyrrolidine (0.81 g, 4.35 mmol) and 4-bromo-2-nitrobenzaldehyde (1.00 g, 4.35 mmol) in MeOH (15 ml) was stirred at rt for 2 hr. Sodium borohydride (0.33 g, 8.69 mmol) was added to the reaction mixture at 0° C. The reaction mixture was stirred at rt for 24 h. The reaction mixture was concentrated under reduced pressure. The resulting reaction mixture was poured into water (100 ml) and extracted with EtOAc (3×50 ml). The combined organic layer was washed with brine solution (50 ml), dried over Na₂SO₄, filtered and concentrated under reduced pressure. The resulting residue was purified by column chromatography (20% EtOAc in hexane) yielding a tert-butyl (R)-3-((4-bromo-2-nitrobenzyl)amino)pyrrolidine-1-carboxylate (0.48 g, 1.20 mmol). LCMS: Method C, 1.82 min, MS: ES+ 400.2.

Step c. To a solution of tert-butyl (R)-3-((4-bromo-2-nitrobenzyl)amino)pyrrolidine-1-carboxylate (0.48 g, 1.20 mmol) in THF:water (4.8 ml:4.8 ml) were added Fe powder (0.20 g, 3.60 mmol) and acetic acid (0.34 ml, 6.00 mmol) at rt. The reaction mixture was heated at 75° C. for 1 h. The resulting reaction mixture was diluted with EtOAc (10 ml) and filtered through celite hyflow. The filtrate was poured into saturated NaHCO₃ solution (50 ml) and extracted with EtOAc (3×30 ml). The combined organic layer was washed with brine solution (50 ml), dried over Na₂SO₄, filtered and concentrated under reduced pressure yielding tert-butyl (R)-3-((2-amino-4-bromobenzyl)amino)pyrrolidine-1-carboxylate (0.40 g, 1.08 mmol). This material was used directly for the next step without further purification. LCMS: Method C, 1.82 min, MS: ES+ 370.3.

Step d. To a solution of tert-butyl (R)-3-((2-amino-4-bromobenzyl)amino)pyrrolidine-1-carboxylate (0.40 g, 1.08 mmol) in pyridine (10 ml) was added sulfamide (1.04 g, 10.83 mmol) at rt. The reaction mixture was heated at 125° C. for 36 h. The resulting reaction mixture was concentrated under reduced pressure. The resulting residue was purified by column chromatography (20% EtOAc in hexane) yielding a tert-butyl (R)-3-(7-bromo-2,2-dioxido-1,4-dihydro-3H-benzo[c][1,2,6]thiadiazin-3-yl)pyrrolidine-1-carboxylate (0.17 g, 0.39 mmol). This material was used directly for the next step without further purification. LCMS: Method C, 2.35 min, MS: ES-430.4.

Step e. A solution of tert-butyl (R)-3-(7-bromo-2,2-dioxido-1,4-dihydro-3H-benzo[c][1,2,6]thiadiazin-3-yl)pyrrolidine-1-carboxylate (0.17 g, 0.39 mmol) and 1-methyl-4-pyrazole boronic acid pinacol ester (0.09 g, 0.47 mmol) in dioxane:water (4:1, 5 ml) was prepared in a glass vial. The reaction mixture was treated with $Cs_2CO_3$ (0.26 g, 0.79 mmol) and degassed for 30 min before adding $Pd(PPh_3)_4$ (0.02 g, 0.019 mol). The glass vial was sealed and subjected to heating at 90° C. for 1 h. The resulting reaction mixture was poured into water (50 ml) and extracted with EtOAc (3×25 ml). The combined organic layer was washed with brine solution (25 ml). The organic phase was collected, dried over $Na_2SO_4$, filtered and concentrated under reduced pressure. The resulting residue was purified by column chromatography (80% EtOAc in hexane) yielding a tert-butyl (R)-3-(7-(1-methyl-1H-pyrazol-4-yl)-2,2-dioxido-1,4-dihydro-3H-benzo[c][1,2,6]thiadiazin-3-yl)pyrrolidine-1-carboxylate (0.18 g, quantitative). LCMS: Method C, 2.16 min, MS: ES+ 434.3.

Steps f, g. The title compound was synthesised from the intermediate above using a procedure similar to that described for steps e and f of Example 1. LCMS: Method A, 2.11 min, MS: ES+ 359.02. $^1$H NMR (400 MHz, DMSO-d6) δ ppm 10.50 (s, 1H), 8.08 (s, 1H), 7.77 (s, 1H), 7.16-7.27 (m, 2H), 6.88 (d, J=1.2 Hz, 1H), 4.66 (s, 2H), 3.98-4.02 (m, 1H), 3.86 (s, 3H), 3.55 (q, J=7.6 Hz, 1H), 3.30-3.45 (m, 1H), 3.28-3.33 (m, 2H), 1.95-2.02 (m, 1H), 1.87-1.93 (m, 1H).

Example 72 (R)-3-(2,2-dioxido-7-phenyl-1,4-dihydro-3H-benzo[c][1,2,6]thiadiazin-3-yl)pyrrolidine-1-carbonitrile

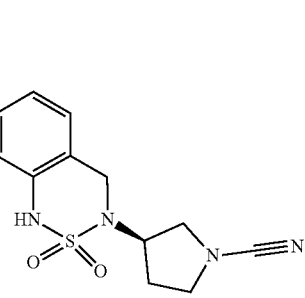

Synthesised using a procedure similar to that described for Example 71. LCMS: Method B, 4.14 min, MS: ES+ 355.31. $^1$H NMR (400 MHz, DMSO-d6) δ ppm 10.65 (s, 1H), 7.59-7.61 (m, 2H), 7.46-7.49 (m, 2H), 7.37-7.40 (m, 1H), 7.28-7.34 (m, 2H), 7.01 (d, J=1.6 Hz, 1H), 4.74 (s, 2H), 3.99-4.07 (m, 1H), 3.58 (q, J=7.6 Hz, 1H), 3.42-3.47 (m, 1H), 3.30-3.36 (m, 2H), 1.99-2.06 (m, 1H), 1.88-1.96 (m, 1H).

Example 73 (R)-3-(1-methyl-2,2-dioxido-7-phenyl-1,4-dihydro-3H-benzo[c][1,2,6]thiadiazin-3-yl)pyrrolidine-1-carbonitrile

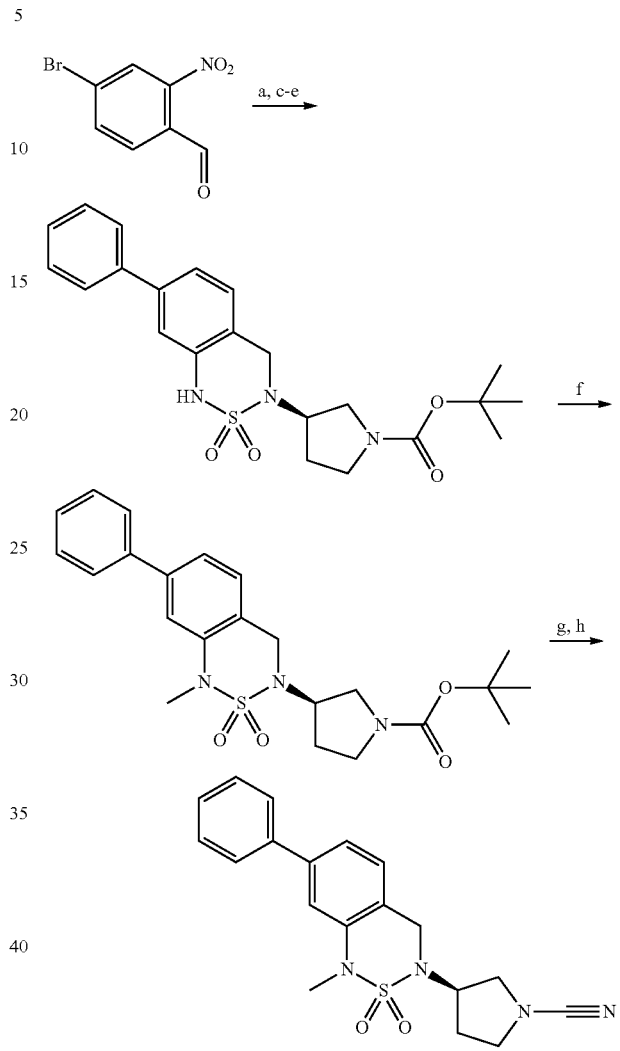

Steps a, c-e. Synthesis was Conducted According to Example 72, Steps a, c-e.

Step f. To a solution of tert-butyl (R)-3-(2,2-dioxido-7-phenyl-1,4-dihydro-3H-benzo[c][1,2,6]thiadiazin-3-yl)pyrrolidine-1-carboxylate (0.30 g, 0.70 mmol) in THF (10 ml) was added NaH (0.101 g, 4.20 mmol) at 0° C. The reaction mixture was stirred at rt for 30 min. Methyl iodide (0.19 g, 1.40 mmol) was added to the reaction mixture at 0° C. and stirred at rt for 1.5 h. The resulting reaction mixture was poured into water (30 ml) and extracted with EtOAc (2×35 ml). The combined organic layer was collected, dried over $Na_2SO_4$, filtered and concentrated under reduced pressure. The resulting residue was purified by column chromatography (17% EtOAc in hexane) yielding tert-butyl (R)-3-(1-methyl-2,2-dioxido-7-phenyl-1,4-dihydro-3H-benzo[c][1,2,6]thiadiazin-3-yl)pyrrolidine-1-carboxylate (0.13 g, 0.29 mmol). LCMS: Method C, 2.77 min, MS: ES+ 388.45 (M−56).

Steps g-h. The title compound was synthesised from the intermediate above using a procedure similar to that described for steps e and f of Example 1. LCMS: Method B, 4.46 min, MS: ES+ 369.31. $^1$H NMR (400 MHz, CDCl$_3$) δ ppm 7.57 (dd, J=1.6 Hz, J=8.8 Hz, 2H), 7.46-7.50 (m, 2H), 7.39-7.43 (m, 1H), 7.29-7.31 (m, 1H), 7.18 (d, J=8.0 Hz, 1H), 7.11 (d, J=1.2 Hz, 1H), 4.82 (d, J=17.2 Hz, 1H), 4.68 (d, J=17.6 Hz, 1H), 4.19-4.23 (m, 1H), 3.68 (q, J=7.6 Hz, 1H), 3.54-3.59 (m, 1H), 3.34-3.43 (m, 5H), 2.15-2.21 (m, 1H), 2.05-2.12 (m, 1H).

Example 74 (R)-3-(1-methyl-2,2-dioxido-6-phenyl-1,4-dihydro-3H-benzo[c][1,2,6]thiadiazin-3-yl)pyrrolidine-1-carbonitrile

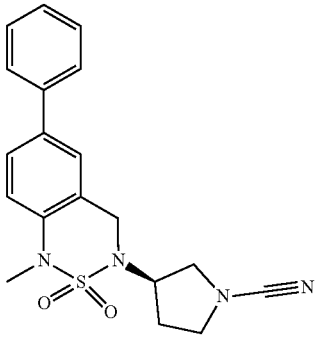 [SMILES: CN1c2ccc(-c3ccccc3)cc2CN([C@@H]2CCN(C#N)C2)S1(=O)=O]

Synthesised using a procedure similar to that described for Example 73 using 5-bromo-2-nitrobenzaldehyde. LCMS: Method B, 4.30 min, MS: ES+ 355.46. $^1$H NMR (400 MHz, DMSO-d6) δ ppm 10.74 (s, 1H), 7.63 (d, J=7.2 Hz, 2H), 7.54 (d, J=8 Hz, 2H), 7.44 (t, J=7.6 Hz, 2H), 7.33 (t, J=7.2 Hz, 1H), 6.84 (d, J=8.4 Hz, 1H), 4.75 (s, 2H), 3.98-4.02 (m, 1H), 3.55-3.6 (m, 1H), 3.41-3.46 (m, 1H), 3.29-3.34 (m, 2H), 2.0-2.05 (m, 1H), 1.9-1.95 (m, 1H).

Example 75 (R)-3-(2,2-dioxido-6-phenyl-1,4-dihydro-3H-benzo[c][1,2,6]thiadiazin-3-yl)pyrrolidine-1-carbonitrile

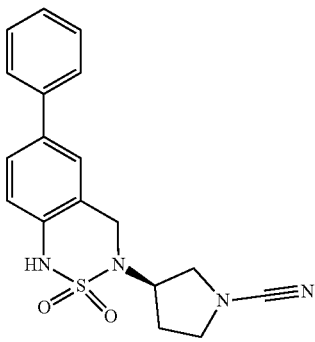 [SMILES: N#CN1CC[C@@H](N2Cc3cc(-c4ccccc4)ccc3NS2(=O)=O)C1]

Synthesised using a procedure similar to that described for Example 72 using 3-nitro-[1,1'-biphenyl]-4-carbaldehyde and omitting step f (BOC deprotection occurred during step d). LCMS: Method B, 4.42 min, MS: ES+ 355.0. $^1$H NMR (400 MHz, DMSO-d6) δ ppm 7.44 (d, J=6.8 Hz, 2H), 7.39 (dd, J=2.0 Hz, J=7.2 Hz, 2H), 7.29-7.33 (m, 1H), 7.13 (dd, J=1.2 Hz, J=8.0 Hz, 1H), 6.93-7.03 (m, 2H), 6.82 (dd, J=1.2 Hz, J=7.6 Hz, 1H), 4.98 (s, 2H), 4.87-4.95 (m, 1H), 3.88 (q, J=7.6 Hz, 1H), 3.65-3.73 (m, 2H), 3.50 (q, J=8.0 Hz, 1H), 2.32-2.47 (m, 2H).

Example 76 N-(1-cyanopyrrolidin-3-yl)-N,N'-dimethyl-N'-phenylsulfuric diamide

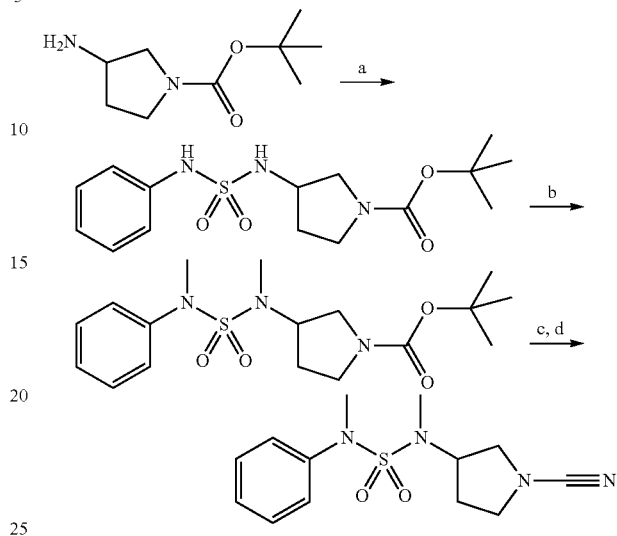

Step a. A solution of tert-butyl 3-aminopyrrolidine-1-carboxylate (1.00 g, 5.37 mmol) and imidazole (1.09 g, 16.12 mmol) in DCM (30 ml) was cooled at −78° C. SO$_2$Cl$_2$ (0.44 ml, 5.37 mmol) was added to the reaction mixture at −78° C. and stirred for 20 min. The reaction mixture was stirred for a further 30 min at rt and then treated with aniline (0.50 g, 5.37 mmol). The reaction mixture was was heated at 70° C. for 1 h and then poured into 1 M citric acid solution (100 ml) and extracted with EtOAc (2×100 ml). The combined organic phase was collected, dried over Na$_2$SO$_4$, filtered and concentrated under reduced pressure. The resulting residue was purified by flash chromatography (12% EtOAc in hexane) yielding tert-butyl 3-((N-phenylsulfamoyl)amino)pyrrolidine-1-carboxylate (0.75 g, 2.20 mmol). LCMS: Method C, 2.11 min, MS: ES+ 342.2.

Step b. To a suspension of tert-butyl 3-((N-phenylsulfamoyl)amino)pyrrolidine-1-carboxylate (0.25 g, 0.73 mmol) and K$_2$CO$_3$ (0.4 g, 2.93 mmol) in MeCN (15 ml) was added CH$_3$I (0.14 ml, 2.20 mmol) at rt. The reaction mixture was stirred at 70° C. for 3 h. The resulting reaction mixture was allowed to cool to rt and quickly poured into water (100 ml). The resulting aqueous was extracted with EtOAc (2×100 ml). The combined organic phase was collected, dried over Na$_2$SO$_4$, filtered and concentrated under reduced pressure yielding tert-butyl 3-(methyl(N-methyl-N-phenylsulfamoyl)amino)pyrrolidine-1-carboxylate (0.20 g, 0.54 mmol). LCMS: Method C, 2.32 min, MS: ES+ 314.18 (M−56).

Step c. To tert-butyl 3-(methyl(N-methyl-N-phenylsulfamoyl)amino)pyrrolidine-1-carboxylate (0.20 g, 0.542 mmol) was added 4 M HCl in 1,4-dioxane (10 ml)) at rt and stirred for 1 h. The resulting reaction mixture was concentrated under reduced pressure. The resulting residue was triturated with diethyl ether (20 ml) yielding N,N'-dimethyl-N-phenyl-N'-pyrrolidin-3-ylsulfuric diamide HCl salt (0.114 g, 0.37 mmol). This material was used directly for the next step without further purification. LCMS: Method C, 1.63 min, MS: ES+ 270.21; $^1$H NMR (400 MHz, DMSO-d6) δ ppm 9.24 (br s, 1H), 8.97 (br s, 1H), 7.40-7.43 (m, 4H), 7.29-7.34 (m, 1H), 4.27-4.51 (m, 1H), 3.36-3.49 (m, 1H), 3.18 (S, 3H), 3.06-3.14 (m, 2H), 2.92-2.98 (m, 1H), 2.75 (s, 3H), 1.84-1.90 (m, 2H).

Step d. To a solution of N,N'-dimethyl-N-phenyl-N'-pyrrolidin-3-ylsulfuric diamide HCl salt (0.114 g, 0.42 mmol) in THF (3 ml) was added K$_2$CO$_3$ (0.18 g, 1.27 mmol) at 0° C. Cyanogen bromide (0.045 g, 0.42 mmol) was added to the reaction mixture at 0° C. The reaction mixture was stirred at 0° C. for 10 min then allowed to stir at rt for 2 h. The resulting reaction mixture was poured into water (100 ml) and extracted with EtOAc (2×75 ml). The combined organic phase was washed with brine solution (50 ml), dried over Na$_2$SO$_4$, filtered and concentrated under reduced pressure. The resulting residue was purified by flash chromatography (0.5% MeOH in DCM) yielding the title compound (0.060 g, 0.20 mmol). LCMS: Method A, 4.08 min, MS: ES+ 295; $^1$H NMR (400 MHz, DMSO-d6) δ ppm 7.39-7.42 (m, 4H), 7.27-7.32 (m, 1H), 4.32-4.38 (m, 1H), 3.43-3.47 (m, 1H), 3.19-3.33 (m, 3H), 3.17 (s, 3H), 2.72 (s, 3H), 1.84-1.90 (m, 2H).

Example 77 (R)-3-(8-morpholino-2,2-dioxido-1,4-dihydro-3H-benzo[c][1,2,6]thiadiazin-3-yl)pyrrolidine-1-carbonitrile min, MS: ES+ 407.38; $^1$H NMR (400 MHz, DMSO-d6) δ ppm 7.50-7.52 (m, 1H), 7.36-7.41 (m, 2H), 3.62-3.64 (m, 6H), 3.25-3.30 (m, 3H), 3.12-3.18 (m, 2H), 2.91-2.95 (m, 1H), 2.86-2.88 (m, 4H), 1.82-1.84 (m, 1H), 1.58-1.60 (m, 1H), 1.37 (s, 9H).

Step c. To a solution of tert-butyl (R)-3-((3-morpholino-2-nitrobenzyl)amino) pyrrolidine-1-carboxylate (0.41 g, 1.01 mmol) in THF:Water (1:1, 10 ml) was added Fe power (0.17 g, 3.03 mmol) and acetic acid (0.56 g, 5.05 mmol) at rt. The reaction mixture was heated at 100° C. for 1 h. The resulting mixture was allowed to cool at rt and neutralized by saturated aqueous NaHCO$_3$ solution (100 ml). The resulting mixture was extracted with EtOAc (4×25 ml). The combined organic phase was collected, dried over Na$_2$SO$_4$, filtered and concentrated under reduced yielding tert-butyl (R)-3-((2-amino-3-morpholinobenzyl)amino)pyrrolidine-1-carboxylate (0.375 g, 1.00 mmol). The material was used directly for the next step without further purification. LCMS: Method C, 1.79 min, MS: ES+ 377.48; $^1$H NMR (400 MHz, DMSO-d6) δ ppm 6.89 (dd, J=7.60, 1.20 Hz,

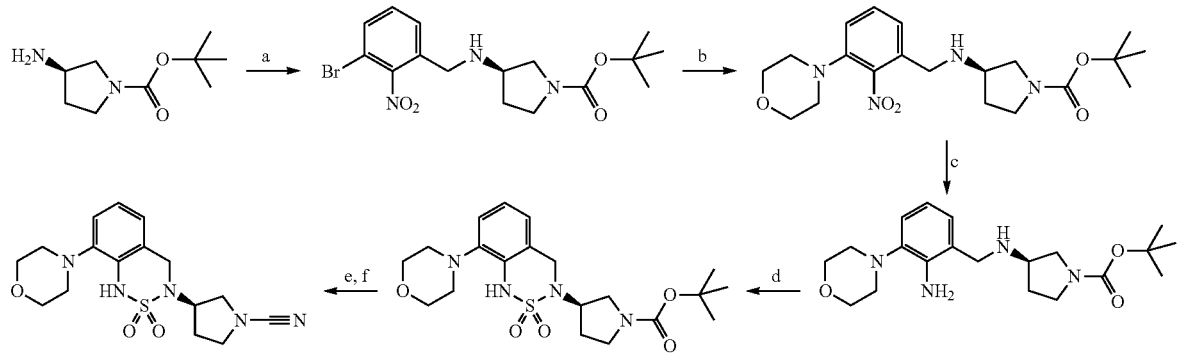

Step a. To a solution of 3-bromo-2-nitrobenzaldehyde (0.35 g, 1.52 mmol) in DCM (15 ml) was added acetic acid (10 drop) and tert-butyl (R)-3-aminopyrrolidine-1-carboxylate (0.28 g, 1.52 mmol) at rt and stirred for 30 min. The resulting reaction mixture was cooled to 0° C. and treated with sodium triacetoxyborohydride (0.97 g, 4.58 mmol) in equal portions. The reaction mixture was stirred at rt for 16 h. The resulting mixture was neutralized by saturated aqueous NaHCO$_3$ solution (100 ml) and extracted with DCM (3×30 ml). The combined organic phase was collected, dried over Na$_2$SO$_4$, filtered and concentrated under reduced pressure. The resulting residue was purified by column chromatography (50-100% EtOAc in hexane) yielding tert-butyl (R)-3-((3-bromo-2-nitrobenzyl)amino) pyrrolidine-1-carboxylate (0.53 g, 1.32 mmol). LCMS: Method C, 1.93 min, MS: ES+ 344.6, 346.30 [M−56].

Step b. A mixture of tert-butyl (R)-3-((3-bromo-2-nitrobenzyl)amino) pyrrolidine-1-carboxylate (0.50 g, 1.25 mmol) and morpholine (5 ml) was heated at 110° C. for 16 h. The resulting reaction mixture was poured into water (125 ml) and extracted with EtOAc (4×25 ml). The combined organic phase was washed with brine solution (30 ml), dried over Na$_2$SO$_4$, filtered and concentrated under reduced pressure. The resulting residue was purified by column chromatography (50-60% EtOAc in hexane) yielding tert-butyl (R)-3-((3-morpholino-2-nitrobenzyl)amino) pyrrolidine-1-carboxylate (0.47 g, 1.15 mmol). LCMS: Method C, 1.84

1H), 6.82 (d, J=7.60 Hz, 1H), 6.55 (t, J=7.60 Hz, 1H), 5.01 (br s, 2H), 3.73-3.75 (m, 4H), 3.64-3.66 (m, 2H), 3.32-3.36 (m, 3H), 3.18-3.21 (m, 2H), 3.02-3.05 (m, 1H), 2.75-2.77 (m, 4H), 1.91-1.92 (m, 1H), 1.64-1.70 (m, 1H), 1.38 (s, 9H).

Step d. To a solution of tert-butyl (R)-3-((2-amino-3-morpholinobenzyl)amino) pyrrolidine-1-carboxylate (0.375 g, 1.00 mmol) in pyridine (8 ml) was added sulfamide (0.96 g, 10.00 mmol) at rt. The reaction mixture was heated at 125° C. for 48 h. The resulting reaction mixture was poured into water (120 ml) and extracted with EtOAc (4×30 ml). The combined organic phase was washed with brine solution (2×20 ml), dried over Na$_2$SO$_4$, filtered and concentrated under reduced pressure. The resulting residue was purified by column chromatography (30-40% EtOAc in hexane) yielding tert-butyl (R)-3-(8-morpholino-2,2-dioxido-1,4-dihydro-3H-benzo[c][1,2,6]thiadiazin-3-yl)pyrrolidine-1-carboxylate (0.21 g, 0.47 mmol). LCMS: Method C, 2.24 min, MS: ES+ 439.70 Steps e, f. The title compound was synthesised from the intermediate above using a procedure similar to that described for steps e and f of Example 1. LCMS: Method A, 2.25 min, MS: ES+ 364.08; $^1$H NMR (400 MHz, DMSO-d$_6$) δ ppm 9.51 (s, 1H), 7.01-7.05 (m, 2H), 6.92-6.94 (m, 1H), 4.67 (s, 2H), 4.00-4.04 (m, 1H), 3.78-3.80 (m, 4H), 3.55-3.59 (m, 1H), 3.40-3.45 (m, 1H), 3.25-3.35 (m, 2H), 2.77-2.86 (m, 4H), 1.90-2.01 (m, 1H), 1.84-1.87 (m, 1H).

Example 78 (R)-3-(8-morpholino-2,2-dioxido-1,4-dihydro-3H-pyrido[3,4-c][1,2,6]thiadiazin-3-yl)pyrrolidine-1-carbonitrile

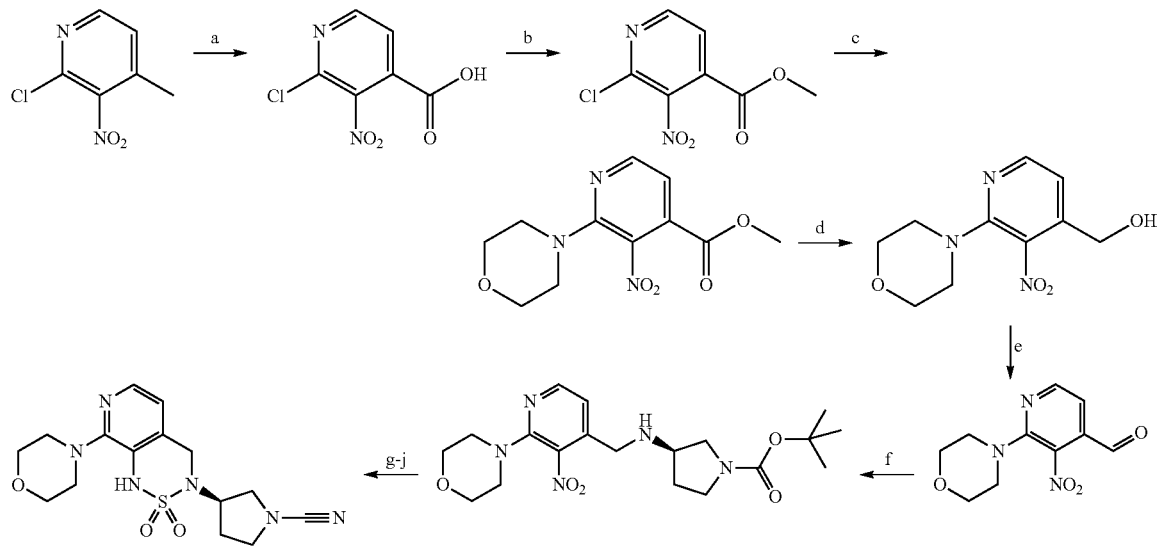

Step a. To a solution of 2-chloro-4-methyl-3-nitropyridine (4.00 g, 23.00 mmol) in H$_2$SO$_4$ (40 ml) was added K$_2$Cr$_2$O$_7$ (8.85 g, 30.00 mmol) portion wise at 0° C. The reaction mixture was heated at 60° C. for 8 h. The resulting mixture was allowed to cool at rt and slowly poured onto ice. The mixture was extracted with EtOAc (5×30 ml). The combined organic phase was collected, dried over Na$_2$SO$_4$, filtered and concentrated under reduced pressure. The resulting residue was triturated with n-pentane (3×5 ml) yielding 2-chloro-3-nitroisonicotinic acid (4.00 g, 19.70 mmol). The material was used directly for the next step without further purification. LCMS: Method C, 1.51 min, MS: ES-201.1 [M−1]; $^1$H NMR (400 MHz, DMSO-d6) δ ppm 8.83 (d, J=5 Hz, 1H), 8.03 (d, J=5 Hz, 1H).

Step b. To a solution of 2-chloro-3-nitroisonicotinic acid (2.60 g, 12.80 mmol) in MeOH (30 ml) was added H$_2$SO$_4$ (4 ml) at rt. The reaction mixture was heated at 60° C. for 16 h. The resulting mixture was concentrated under reduced pressure, neutralized with saturated aqueous NaHCO$_3$ solution (100 ml) and extracted with EtOAc (3×30 ml). The combined organic phase was collected, dried over Na$_2$SO$_4$, filtered and concentrated under reduced pressure yielding methyl 2-chloro-3-nitroisonicotinate (2.60 g, 11.98 mmol). The material was used directly for the next step without further purification. $^1$H NMR (400 MHz, DMSO-d6) δ ppm 8.88 (d, J=4.80 Hz, 1H), 8.08 (d, J=4.80 Hz, 1H), 3.88 (s, 3H).

Step c. To a solution of methyl 2-chloro-3-nitroisonicotinate (1.00 g, 4.60 mmol) in THF (10 ml) were added K$_2$CO$_3$ (1.27 g, 9.20 mmol) and morpholine (0.50 g, 5.50 mmol) at rt. The resulting reaction mixture was heated at 60° C. for 16 h. The resulting reaction mixture was allowed to cool at rt and poured into brine solution (100 ml). The resulting mixture was extracted with EtOAc (4×20 ml). The combined organic phase was dried over Na$_2$SO$_4$, filtered and concentrated under reduced pressure. The resulting residue was triturated with n-pentane (3×2 ml) yielding methyl 2-morpholino-3-nitroisonicotinate (0.75 g, 2.80 mmol). The material was used directly for the next step without further purification. LCMS: Method C, 2.12 min, MS: ES+ 268.18; $^1$H NMR (400 MHz, DMSO-d6) δ ppm 8.54 (d, J=4.80 Hz, 1H), 7.18 (d, J=4.80 Hz, 1H), 3.85 (s, 3H), 3.64-3.66 (m, 4H), 3.30-3.34 (m, 4H).

Step d. To a solution of methyl 2-morpholino-3-nitroisonicotinate (0.74 g, 2.77 mmol) in toluene (10 ml) was added 1M solution of DIBAL-H in toluene (5.54 ml, 5.50 mmol) at −50° C. The resulting reaction mixture was stirred at −50° C. for 1 h. The resulting reaction mixture was allowed to warm at rt and poured brine solution (100 ml). The resulting mixture was extracted with EtOAc (3×20 ml). The combined organic phase was dried over Na$_2$SO$_4$, filtered and concentrated under reduced pressure yielding (2-morpholino-3-nitropyridin-4-yl)methanol (0.70 g, quantitative). The material was used directly for the next step without further purification. LCMS: Method C, 1.62 min, MS: ES+ 240.35; $^1$H NMR (400 MHz, DMSO-d6) δ ppm 8.37 (d, J=5.20, 1H), 7.13 (d, J=5.20 Hz, 1H), 5.66 (br s, 1H), 4.51 (s, 2H), 3.63-3.65 (m, 4H), 3.24-3.26 (m, 4H).

Step e. To a solution of (2-morpholino-3-nitropyridin-4-yl)methanol (0.69 g, 2.80 mmol) in DCM (10 ml) was added MnO$_2$ (3.76 g, 43.00 mmol) at rt and stirred for 20 h. The resulting reaction mixture was filtered through celite hyflow. The filtrate was concentrated under reduced pressure yielding 2-morpholino-3-nitroisonicotinaldehyde (0.61 g, 2.57 mmol). The material was used directly for the next step without further purification. LCMS: Method C, 2.02 min, MS: ES+ 238.20; $^1$H NMR (400 MHz, DMSO-d6) δ ppm 10.02 (s, 1H), 8.63 (d, 1H), 7.21 (d, 1H), 3.63-3.68 (m, 4H), 3.34-3.36 (m, 4H).

Step f. To a solution of 2-morpholino-3-nitroisonicotinaldehyde (0.60 g, 2.50 mmol) in DCM (15 ml) was added acetic acid (0.1 ml) and tert-butyl (R)-3-aminopyrrolidine-1-carboxylate (0.46 g, 2.50 mmol) at rt and stirred for 40 min. The resulting reaction mixture was cooled to 0° C. and treated with sodium triacetoxyborohydride (1.50 g, 7.50 mmol) in equal portions. The reaction mixture was stirred at rt for 16 h. The resulting mixture was poured into water (100 ml) and extracted with DCM (3×30 ml). The combined organic phase was collected, dried over Na₂SO₄, filtered and concentrated under reduced pressure. The resulting residue was purified by column chromatography (0-35% EtOAc in hexane) yielding tert-butyl (R)-3-(((2-morpholino-3-nitropyridin-4-yl)methyl)amino)pyrrolidine-1-carboxylate (0.32 g, 0.78 mmol). LCMS: Method C, 1.81 min, MS: ES+ 408.48; $^1$H NMR (400 MHz, DMSO-d6) δ ppm 8.33 (d, J=5 Hz, 1H), 7.15 (d, J=5 Hz, 1H), 3.67-3.71 (m, 2H), 3.63-3.65 (t, J=4.40 Hz, 4H), 3.34-3.41 (m, 1H), 3.26-3.32 (m, 2H), 3.21-3.23 (t, J=4.40, 4H), 3.10-3.18 (m, 2H), 2.91-2.95 (m, 1H), 1.81-1.91 (m, 1H), 1.57-1.62 (m, 1H), 1.38 (m, 9H).

Steps g-j. The title compound was synthesised from the intermediate above using a procedure similar to that described for steps c-f of Example 77. LCMS: Method A, 1.93 min, MS: ES+ 365.74; $^1$H NMR (400 MHz, DMSO-d6) δ ppm 9.78 (s, 1H), 7.97 (d, J=5.20 Hz, 1H), 6.89 (d, J=5.20 Hz, 1H), 4.68 (s, 2H), 4.02-4.06 (m, 1H), 3.76-3.80 (m, 4H), 3.46-3.61 (m, 1H), 3.39-3.46 (m, 1H), 3.26-3.32 (m, 2H), 3.04-3.16 (m, 4H), 1.99-2.04 (m, 1H), 1.81-1.87 (m, 1H).

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue In Vitro USP30 Inhibition Assay USP30 biochemical kinetic assay. Reactions were performed in duplicate in black 384 well plates (small volume, Greiner 784076) in a final reaction volume of 21 μl. USP30 CD (57-517, #64-0057-050 Ubiquigent) was diluted in reaction buffer (40 mM Tris, pH 7.5, 0.005% Tween 20, 0.5 mg/ml BSA, 5 mM—beta-mercaptoethanol) to the equivalent of 0, 0.005, 0.01, 0.05, 0.1 and 0.5 l/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 μM for a final concentration of 100 μM) in 50% DMSO in a 96-well polypropylene V-bottom plate (Greiner #651201). A typical 8-point dilution series to be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. USP30 was diluted in reaction buffer (40 mM Tris, pH 7.5, 0.005% Tween 20, 0.5 mg/ml BSA, 5 mM—beta-mercaptoethanol) to the equivalent of 0.05 μl/well and 10 μl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in USP30 Biochemical IC50 Assay

Ranges:
A<0.1 μM;
0.1<B<1 μM;
1<C<10 μM

| Example | IC50 range |
|---------|------------|
| 1 | B |
| 2 | A |
| 3 | B |
| 4 | A |
| 5 | A |
| 6 | B |
| 7 | A |
| 8 | B |
| 9 | B |
| 10 | A |
| 11 | A |
| 12 | B |
| 13 | A |
| 14 | B |
| 15 | A |
| 16 | A |
| 17 | A |
| 18 | A |
| 19 | A |
| 20 | A |
| 21 | B |
| 22 | B |
| 23 | A |
| 24 | A |
| 25 | C |
| 26 | A |
| 27 | B |
| 28 | A |
| 29 | B |
| 30 | B |
| 31 | C |
| 32 | A |
| 33 | A |
| 34 | A |
| 35 | A |
| 36 | A |
| 37 | B |
| 38 | B |
| 39 | A |
| 40 | B |
| 41 | B |
| 42 | A |
| 43 | A |
| 44 | B |
| 45 | C |
| 46 | C |
| 47 | B |
| 48 | B |
| 49 | A |
| 50 | A |
| 51 | B |
| 52 | B |
| 53 | B |
| 54 | B |
| 55 | B |
| 56 | B |
| 57 | B |
| 58 | B |
| 59 | B |
| 60 | B |
| 61 | C |
| 62 | C |
| 63 | B |
| 64 | B |
| 65 | B |

-continued

| Example | IC50 range |
|---|---|
| 66 | C |
| 67 | B |
| 68 | C |
| 69 | B |
| 70 | C |
| 71 | B |
| 72 | B |
| 73 | B |
| 74 | B |
| 75 | C |
| 76 | C |
| 77 | C |
| 78 | C |

The invention claimed is:
1. A compound of formula (I):

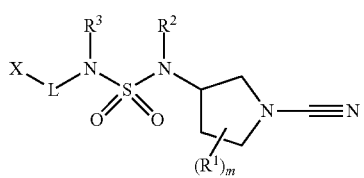

a tautomer thereof, or a pharmaceutically acceptable salt of said compound or tautomer, wherein:
m is an integer from 0 to 3;
each occurrence of $R^1$ is independently selected from the group consisting of fluorine, cyano, hydroxyl, amino, $C_1$-$C_6$ alkyl, $C_1$-$C_6$ alkoxy, or a 3 to 6-membered cycloalkyl, heterocyclyl, aryl or heteroaryl ring;
$R^2$ represents hydrogen, $C_1$-$C_6$ alkyl, a 3 to 10-membered cycloalkyl, heterocyclyl, aryl or heteroaryl ring, or $R^2$ together with $R^3$ forms a 4 to 10-membered heterocyclic ring;
$R^3$ represents hydrogen, $C_1$-$C_6$ alkyl, or a 3 to 10-membered cycloalkyl, heterocyclyl, aryl or heteroaryl ring, or $R^3$ together with $R^2$ forms a 4 to 10-membered heterocyclic ring, or $R^3$ together with X forms an optionally substituted 3 to 10-membered heterocyclyl or heteroaryl ring;
L represents a bond, a $C_1$-$C_6$ alkylene or a $C_2$-$C_6$ alkenylene linker;
X represents hydrogen, $C_1$-$C_6$ alkyl, an optionally substituted 3 to 14-membered cycloalkyl, heterocyclyl, aryl or heteroaryl ring, or X together with $R^3$ forms an optionally substituted 3 to 10-membered heterocyclyl or heteroaryl ring;
wherein when group X is a ring, said ring is optionally substituted with one or more -$Q^1$-$(R^4)_n$, wherein each -$Q^1$-$(R^4)_n$ is the same or different;
wherein the ring formed by $R^2$ together with $R^3$ is optionally substituted with one or more -$Q^2$-$(R^5)_p$, wherein each $Q^2$-$(R^5)_p$ is the same or different;
wherein the ring formed by group X together with $R^3$ is optionally substituted with one or more $Q^3$-$(R^6)_q$, wherein each $Q^3$-$(R^6)_q$ is the same or different;
n is 0 or 1;
p is 0 or 1;
q is 0 or 1;
$Q^1$, $Q^2$ and $Q^3$ each independently represent halogen, cyano, oxo, nitro, —OR', —SR', —NR'R", —CONR'R", —NR'COR", —NR'CONR"R'", —COR', —C(O)OR', —SO$_2$R', —SO$_2$NR'R", —NR'SO$_2$R", NR'SO$_2$NR"R'", —NR'C(O)OR", $C_1$-$C_6$ alkyl, $C_1$-$C_6$ alkoxy, $C_2$-$C_6$ alkenyl, alkynyl, a covalent bond, an oxygen atom, a sulphur atom, —SO—, —SO$_2$—, —CO—, C(O)O, —CONR'—, —NR'—, —NR'CO—, —NR'CONR"—, —SO$_2$NR'—, NR'SO$_2$—, —NR'SO$_2$NR"—, —NR'C(O)O—, —NR'C(O)OR", $C_1$-$C_6$ alkylene, or $C_2$-$C_6$ alkenylene;
R', R" and R'" each independently represent hydrogen, $C_1$-$C_6$ alkyl, $C_1$-$C_6$ alkoxy or $C_1$-$C_6$ alkylene;
$R^4$, $R^5$ and $R^6$ each independently represent a 3 to 10-membered heterocyclyl, cycloalkyl, heteroaryl or aryl ring;
$R^4$ is optionally substituted with one or more substituents selected from halogen, cyano, oxo, nitro —OR$^a$, —SR$^a$, —NR$a$R$^b$, —CONR$^a$R$^b$, —NR$^a$COR$^b$, —NR$^a$CONR$^b$R$^c$, —COR$^a$, —C(O)OR$^a$, —SO$_2$R$^a$, —SO$_2$NR$^a$R$^b$, —NR$^a$SO$_2$R$^b$, —NR$^a$SO$_2$NR$^b$R$^c$, —NR$^a$C(O)OR$^b$, $C_1$-$C_6$ alkyl, $C_1$-$C_6$ alkoxy, $C_2$-$C_6$ alkenyl, $C_2$-$C_6$ alkynyl, -$Q^4$-$R^a$, -$Q^4$-NR$^a$CONR$^b$R$^c$, -$Q^4$-NR$^a$R$^b$, -$Q_4$-COR$^a$, -$Q^4$-NR$^a$COR$^b$, -$Q^4$-NR$^a$C(O)OR$^b$, -$Q^4$-SO$_2$R$^a$, $Q^4$-CONR$^a$R$^b$, -$Q^4$-CO$_2$R$^a$, -$Q^4$-SO$_2$NR$^a$R$^b$, -$Q^4$-NR$^a$SO$_2$R$^b$ and -$Q^4$-NR$^a$SO$_2$NR$^b$R$^c$;
$Q^4$ represents a covalent bond, an oxygen atom, a sulphur atom, —SO—, —SO$_2$—, —CO—, $C_1$-$C_6$ alkylene or $C_2$-$C_6$ alkenylene;
$R^a$, $R^b$ and $R^c$ each independently represent hydrogen, $C_1$-$C_6$ alkyl, heterocyclyl, cycloalkyl, heteroaryl or aryl ring;
$R^5$ is optionally substituted with one or more substituents selected from halogen, cyano, oxo, nitro —OR$^d$, —SR$^d$, —NR$^d$R$^e$, —CONR$^d$R$^e$, —NR$^d$COR$^e$, —NR$^d$CONR$^e$R$^f$, —COR$^d$, —C(O)OR$^d$, —SO$_2$R$^d$, —SO$_2$NR$^d$R$^e$, —NR$^d$SO$_2$R$^e$, NR$^d$SO$_2$NR$^e$R$^f$, —NR$^d$C(O)OR$^e$, $C_1$-$C_6$ alkyl, $C_1$-$C_6$ alkoxy, $C_2$-$C_6$ alkenyl, $C_2$-$C_6$ alkynyl, -$Q^5$-$R^d$, -$Q^5$-NR$^d$CONR$^e$R$^f$, -$Q^5$-NR$^d$R$^e$, -$Q^5$-COR$^d$, -$Q^5$-NR$^d$COR$^e$, -$Q^5$-NR$^d$C(O)OR$^e$, -$Q^5$-SO$_2$R$^d$, $Q^5$-CONR$^d$R$^e$, -$Q^5$-CO$_2$R$^d$, -$Q^5$-SO$_2$NR$^d$R$^e$, -$Q^5$-NR$^d$SO$_2$R$^e$ and -$Q^5$-NR$^d$SO$_2$NR$^e$R$^f$;
$Q^5$ represents a covalent bond, an oxygen atom, a sulphur atom, —SO—, —SO$_2$—, —CO—, $C_1$-$C_6$ alkylene or $C_2$-$C_6$ alkenylene;
$R^d$, $R^e$ and $R^f$ each independently represent hydrogen, $C_1$-$C_6$ alkyl, heterocyclyl, cycloalkyl, heteroaryl or aryl ring;
$R^6$ is optionally substituted with one or more substituents independently selected from halogen, cyano, oxo, nitro —OR$^g$, —SR$^g$, —NR$^g$R$^h$, —CONR$^g$R$^h$, —NR$^g$COR$^h$, —NR$^g$CONR$^h$R$^i$, —COR$^g$, —C(O)OR$^g$, —SO$_2$R$^g$, —SO$_2$NR$^g$R$^h$, —NR$^g$SO$_2$R$^h$, NR$^g$SO$_2$NR$^h$R$^i$, —NR$^g$C(O)OR$^h$, $C_1$-$C_6$ alkyl, $C_1$-$C_6$ alkoxy, $C_2$-$C_6$ alkenyl, $C_2$-$C_6$ alkynyl, -$Q^6$-$R^g$, -$Q^6$-NR$^g$CONR$^h$R$^i$, -$Q^6$-NR$^g$R$^h$, -$Q^6$-COR$^g$, -$Q^6$-NR$^g$COR$^h$, -$Q^6$-NR$^g$C(O)OR$^h$, -$Q^6$-SO$_2$R$^g$, -$Q^6$-CONR$^g$R$^h$, -$Q^6$-CO$_2$R$^g$, -$Q^6$-SO$_2$NR$^g$R$^h$, -$Q^6$-NR$^g$SO$_2$R$^h$ and -$Q^6$-NR$^g$SO$_2$NR$^h$R$^i$;
$Q^6$ represents a covalent bond, an oxygen atom, a sulphur atom, —SO—, —SO$_2$—, —CO—, $C_1$-$C_6$ alkylene or $C_2$-$C_6$ alkenylene; and
$R^g$, $R^h$ and $R^i$ each independently represent hydrogen, $C_1$-$C_6$ alkyl, heterocyclyl, cycloalkyl, heteroaryl or aryl ring; and
wherein said $C_1$-$C_6$ alkyl, $C_1$-$C_6$ alkoxy, $C_2$-$C_6$ alkenyl, $C_2$-$C_6$ alkynyl, $C_1$-$C_6$ alkylene and $C_2$-$C_6$ alkenylene groups, are each independently optionally substituted with one or more substituents selected from halogen, hydroxyl, thiol, cyano, amino, nitro and $SF_5$.

2. The compound of claim 1, wherein $R^1$ is independently selected from the group consisting of fluorine, cyano, hydroxyl, amino, optionally substituted $C_1$-$C_6$ alkyl and optionally substituted $C_1$-$C_6$ alkoxy.

3. The compound of claim 2, wherein $R^1$ is methyl.

4. The compound of claim 1, wherein L represents a covalent bond or methylene.

5. The compound of claim 1, wherein m is 0 or 1.

6. The compound of claim 1, wherein the ring formed by $R^2$ together with $R^3$ is selected from 1,1-dioxido-1,2,5-thiadiazolidin-2-yl, 1,1-dioxido-1,2,6-thiadiazinan-2-yl, 2,2-dioxidobenzo[c][1,2,5]thiadiazol-1(3H)-yl, 1,4-dihydro-3H-pyrido[3,4-c][1,2,6]thiadiazin-3-yl and 1,4-dihydro-3H-benzo[c][1,2,6]thiadiazin-3-yl.

7. The compound of claim 1, wherein the ring formed by $R^2$ together with $R^3$ is substituted by phenyl, pyrazole or morpholinyl, each of which is optionally substituted with $C_1$-$C_6$ alkyl or $C_1$-$C_6$ alkoxy.

8. The compound of claim 1, wherein X is selected from hydrogen, methyl, and an optionally substituted ring selected from phenyl, 9H-carbazole, isoxazole, pyrazole, pyridine, benzimidazole, pyrimidine, benzomorpholine and pyrrolidine.

9. The compound of claim 1, wherein the ring of group X is substituted by 1 or 2 groups independently selected from oxo, $C_1$-$C_6$ alkyl and $C_1$-$C_6$ alkoxy, wherein said alkyl and alkoxy are optionally substituted with one or more groups selected from halogen, hydroxyl, thiol, cyano, amino, nitro and $SF_5$.

10. The compound of claim 1, wherein the ring of group X is substituted by a ring selected from phenyl, pyridinyl, pyrazolyl, morpholinyl, isozazolyl, azetidinyl, pyrrolidinyl and piperazinyl, each of which is optionally substituted with $C_1$-$C_6$ alkyl or $C_1$-$C_6$ alkoxy.

11. The compound of claim 1, wherein the ring formed by X together with $R^3$ is selected from piperidinyl, piperazinyl, indolinyl, benzopiperidinyl, dihydroisoquinolinyl and dihydropyrazolo[1,5-a]pyrimidinyl.

12. The compound of claim 1, wherein the ring formed by X together with $R^3$ is substituted by methoxy or phenyl.

13. The compound according to claim 1, having the structure of formula (II)

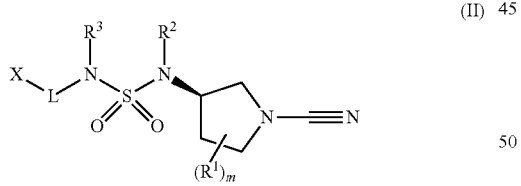

(II)

a tautomer thereof, or a pharmaceutically acceptable salt of said compound or tautomer.

14. The compound according to claim 1, having the structure of formula (IIA)

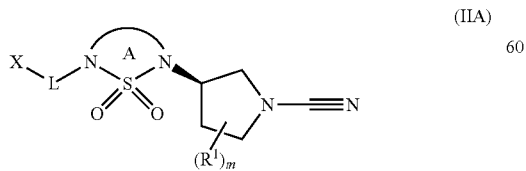

(IIA)

a tautomer thereof, or a pharmaceutically acceptable salt of said compound or tautomer, wherein: ring A represents an optionally substituted 4 to 10 membered heterocyclyl ring formed by $R^2$ together with $R^3$ of formula (I).

15. A compound, selected from the group consisting of:
(S)-3-(5-(3-(isoxazol-5-yl)phenyl)-1,1-dioxido-1,2,5-thiadiazolidin-2-yl)pyrrolidine-1-carbonitrile;
(R)-3-(5-(4-methyl-3-oxo-3,4-dihydro-2H-benzo[b][1,4]oxazin-7-yl)-1,1-dioxido-1,2,5-thiadiazolidin-2-yl)pyrrolidine-1-carbonitrile;
(R)-3-(1,1-dioxido-5-(3-oxo-3,4-dihydro-2H-benzo[b][1,4]oxazin-7-yl)-1,2,5-thiadiazolidin-2-yl)pyrrolidine-1-carbonitrile;
(R)-3-(5-(4-methyl-3-oxo-3,4-dihydro-2H-benzo[b][1,4]oxazin-6-yl)-1,1-dioxido-1,2,5-thiadiazolidin-2-yl)pyrrolidine-1-carbonitrile;
(R)-3-(1,1-dioxido-5-(3-oxo-3,4-dihydro-2H-benzo[b][1,4]oxazin-6-yl)-1,2,5-thiadiazolidin-2-yl)pyrrolidine-1-carbonitrile;
(R)-3-(5-(4-(2-hydroxyethyl)-3-oxo-3,4-dihydro-2H-benzo[b][1,4]oxazin-6-yl)-1,1-dioxido-1,2,5-thiadiazolidin-2-yl)pyrrolidine-1-carbonitrile;
3-(5-(4-methyl-3-oxo-3,4-dihydro-2H-benzo[b][1,4]oxazin-6-yl)-1,1-dioxido-1,2,5-thiadiazolidin-2-yl)pyrrolidine-1-carbonitrile;
(R)-3-(5-(4-methoxy-3-morpholinophenyl)-1,1-dioxido-1,2,5-thiadiazolidin-2-yl)pyrrolidine-1-carbonitrile;
(3R)-3-(1,1-dioxido-5-(1-(pyridin-2-yl)pyrrolidin-3-yl)-1,2,5-thiadiazolidin-2-yl)pyrrolidine-1-carbonitrile;
(R)-3-(5-(2'-methoxy-[1,1'-biphenyl]-3-yl)-1,1-dioxido-1,2,5-thiadiazolidin-2-yl)pyrrolidine-1-carbonitrile;
(R)-3-(5-([1,1'-biphenyl]-4-yl)-1,1-dioxido-1,2,5-thiadiazolidin-2-yl)pyrrolidine-1-carbonitrile;
(R)-3-(6-([1,1'-biphenyl]-4-yl)-1,1-dioxido-1,2,6-thiadiazinan-2-yl)pyrrolidine-1-carbonitrile;
(R)-3-(5-([1,1'-biphenyl]-3-yl)-1,1-dioxido-1,2,5-thiadiazolidin-2-yl)pyrrolidine-1-carbonitrile;
(R)-3-(6-([1,1'-biphenyl]-3-yl)-1,1-dioxido-1,2,6-thiadiazinan-2-yl)pyrrolidine-1-carbonitrile;
(R)-3-(5-(4-methoxy-[1,1'-biphenyl]-3-yl)-1,1-dioxido-1,2,5-thiadiazolidin-2-yl)pyrrolidine-1-carbonitrile;
(R)-3-(5-(3'-methoxy-[1,1'-biphenyl]-3-yl)-1,1-dioxido-1,2,5-thiadiazolidin-2-yl)pyrrolidine-1-carbonitrile;
(R)-3-(5-(2'-methoxy-[1,1'-biphenyl]-4-yl)-1,1-dioxido-1,2,5-thiadiazolidin-2-yl)pyrrolidine-1-carbonitrile;
(R)-3-(1,1-dioxido-5-(4-(pyridin-4-yl)phenyl)-1,2,5-thiadiazolidin-2-yl)pyrrolidine-1-carbonitrile;
(R)-3-(1,1-dioxido-5-(3-(pyridin-4-yl)phenyl)-1,2,5-thiadiazolidin-2-yl)pyrrolidine-1-carbonitrile;
(R)-3-(5-(3-(1-methyl-1H-pyrazol-4-yl)phenyl)-1,1-dioxido-1,2,5-thiadiazolidin-2-yl)pyrrolidine-1-carbonitrile;
(R)-3-(6-(3-(1-methyl-1H-pyrazol-4-yl)phenyl)-1,1-dioxido-1,2,6-thiadiazinan-2-yl)pyrrolidine-1-carbonitrile;
(R)-3-(5-(4-morpholinophenyl)-1,1-dioxido-1,2,5-thiadiazolidin-2-yl)pyrrolidine-1-carbonitrile;
(R)-3-(5-(3-chloro-4-morpholinophenyl)-1,1-dioxido-1,2,5-thiadiazolidin-2-yl)pyrrolidine-1-carbonitrile;
(R)-3-(5-(3-morpholinophenyl)-1,1-dioxido-1,2,5-thiadiazolidin-2-yl)pyrrolidine-1-carbonitrile;
(R)-3-(6-(3-morpholinophenyl)-1,1-dioxido-1,2,6-thiadiazinan-2-yl)pyrrolidine-1-carbonitrile;
(R)-3-(1,1-dioxido-5-(3-phenylisoxazol-5-yl)-1,2,5-thiadiazolidin-2-yl)pyrrolidine-1-carbonitrile;
(R)-3-(1,1-dioxido-6-(3-phenylisoxazol-5-yl)-1,2,6-thiadiazinan-2-yl)pyrrolidine-1-carbonitrile;
(R)-3-(1,1-dioxido-5-(3-phenyl-1H-pyrazol-5-yl)-1,2,5-thiadiazolidin-2-yl)pyrrolidine-1-carbonitrile;

(R)-3-(1,1-dioxido-6-(3-phenyl-1H-pyrazol-5-yl)-1,2,6-thiadiazinan-2-yl)pyrrolidine-1-carbonitrile;
(R)-N-(1-cyanopyrrolidin-3-yl)-2-phenyl-6,7-dihydropyrazolo[1,5-a]pyrimidine-4(5H)-sulfonamide;
(S)-3-(1,1-dioxido-5-phenyl-1,2,5-thiadiazolidin-2-yl)pyrrolidine-1-carbonitrile;
(S)-3-(1,1-dioxido-5-(4-(pyridin-4-yl)phenyl)-1,2,5-thiadiazolidin-2-yl)pyrrolidine-1-carbonitrile;
(S)-3-(1,1-dioxido-5-(3-(pyridin-4-yl)phenyl)-1,2,5-thiadiazolidin-2-yl)pyrrolidine-1-carbonitrile;
(S)-3-(5-([1,1'-biphenyl]-4-yl)-1,1-dioxido-1,2,5-thiadiazolidin-2-yl)pyrrolidine-1-carbonitrile;
(S)-3-(5-([1,1'-biphenyl]-3-yl)-1,1-dioxido-1,2,5-thiadiazolidin-2-yl)pyrrolidine-1-carbonitrile;
(S)-3-(1,1-dioxido-5-(6-phenylpyridin-2-yl)-1,2,5-thiadiazolidin-2-yl)pyrrolidine-1-carbonitrile;
3-(1,1-dioxido-5-phenyl-1,2,5-thiadiazolidin-2-yl)pyrrolidine-1-carbonitrile;
3-(1,1-dioxido-6-phenyl-1,2,6-thiadiazinan-2-yl)pyrrolidine-1-carbonitrile;
(3R,4S)-3-(5-([1,1'-biphenyl]-4-yl)-1,1-dioxido-1,2,5-thiadiazolidin-2-yl)-4-methylpyrrolidine-1-carbonitrile;
(3S,4R)-3-methyl-4-(5-(3-(4-methylpiperazin-1-yl)phenyl)-1,1-dioxido-1,2,5-thiadiazolidin-2-yl)pyrrolidine-1-carbonitrile;
(3S,4R)-3-methyl-4-(5-(3-morpholinophenyl)-1,1-dioxido-1,2,5-thiadiazolidin-2-yl)pyrrolidine-1-carbonitrile;
(R)-3-(5-(6-methoxy-[1,1'-biphenyl]-3-yl)-1,1-dioxido-1,2,5-thiadiazolidin-2-yl)pyrrolidine-1-carbonitrile;
(R)-3-(5-(2-methoxy-[1,1'-biphenyl]-4-yl)-1,1-dioxido-1,2,5-thiadiazolidin-2-yl)pyrrolidine-1-carbonitrile;
(R)-3-(1,1-dioxido-5-(2-(trifluoromethyl)-1H-benzo[d]imidazol-5-yl)-1,2,5-thiadiazolidin-2-yl)pyrrolidine-1-carbonitrile;
(R)-3-(1,1-dioxido-6-(2-(trifluoromethyl)-1H-benzo[d]imidazol-6-yl)-1,2,6-thiadiazinan-2-yl)pyrrolidine-1-carbonitrile;
(R)-3-(1,1-dioxido-6-(2-(trifluoromethyl)-1H-benzo[d]imidazol-6-yl)-1,2,6-thiadiazinan-2-yl)pyrrolidine-1-carbonitrile;
(S)-3-(1,1-dioxido-5-(3-(pyridin-2-yl)phenyl)-1,2,5-thiadiazolidin-2-yl)pyrrolidine-1-carbonitrile;
(S)-3-(1,1-dioxido-5-(3-(pyridin-3-yl)phenyl)-1,2,5-thiadiazolidin-2-yl)pyrrolidine-1-carbonitrile;
(R)-3-(5-(9-methyl-9H-carbazol-3-yl)-1,1-dioxido-1,2,5-thiadiazolidin-2-yl)pyrrolidine-1-carbonitrile;
(R)-3-(5-(2-morpholinopyridin-4-yl)-1,1-dioxido-1,2,5-thiadiazolidin-2-yl)pyrrolidine-1-carbonitrile;
(R)-3-(5-(4-morpholinopyrimidin-2-yl)-1,1-dioxido-1,2,5-thiadiazolidin-2-yl)pyrrolidine-1-carbonitrile;
(R)-3-(5-(2-(4-methylpiperazin-1-yl)pyridin-4-yl)-1,1-dioxido-1,2,5-thiadiazolidin-2-yl)pyrrolidine-1-carbonitrile;
(R)-3-(5-(3-((R)-3-methoxypyrrolidin-1-yl)phenyl)-1,1-dioxido-1,2,5-thiadiazolidin-2-yl)pyrrolidine-1-carbonitrile;
(R)-3-(5-(2-((R)-3-methoxypyrrolidin-1-yl)pyridin-4-yl)-1,1-dioxido-1,2,5-thiadiazolidin-2-yl)pyrrolidine-1-carbonitrile;
(R)-3-(5-(2-(3-methoxyazetidin-1-yl)pyridin-4-yl)-1,1-dioxido-1,2,5-thiadiazolidin-2-yl)pyrrolidine-1-carbonitrile;
(R)-3-(5-(2-(bis(2-methoxyethyl)amino)pyridin-4-yl)-1,1-dioxido-1,2,5-thiadiazolidin-2-yl)pyrrolidine-1-carbonitrile;
N-biphenyl-3-yl-N'-(1-cyanopyrrolidin-3-yl)sulfuric diamide;
N-biphenyl-4-yl-N'-(1-cyanopyrrolidin-3-yl)sulfuric diamide;
N-(1-cyanopyrrolidin-3-yl)-4-phenylpiperidine-1-sulfonamide;
N-(1-cyanopyrrolidin-3-yl)-4-phenylpiperazine-1-sulfonamide;
N-(1-cyanopyrrolidin-3-yl)indoline-1-sulfonamide;
(R)-N-(1-cyanopyrrolidin-3-yl)-3,4-dihydroisoquinoline-2(1H)-sulfonamide;
(R)-N-(1-cyanopyrrolidin-3-yl)-5-phenylindoline-1-sulfonamide;
(R)-N-(1-cyanopyrrolidin-3-yl)-4-phenylindoline-1-sulfonamide;
(R)-N-(1-cyanopyrrolidin-3-yl)-6-methoxy-3,4-dihydroisoquinoline-2(1H)-sulfonamide;
(R)-3-(3-methyl-2,2-dioxidobenzo[c][1,2,5]thiadiazol-1(3H)-yl)pyrrolidine-1-carbonitrile;
(R)-3-(3-benzyl-2,2-dioxidobenzo[c][1,2,5]thiadiazol-1(3H)-yl)pyrrolidine-1-carbonitrile;
(R)-3-(2,2-dioxido-3-(pyridin-3-ylmethyl)benzo[c][1,2,5]thiadiazol-1(3H)-yl)pyrrolidine-1-carbonitrile;
(R)-3-(1-benzyl-2,2-dioxido-1,4-dihydro-3H-benzo[c][1,2,6]thiadiazin-3-yl)pyrrolidine-1-carbonitrile;
(R)-3-(1-methyl-2,2-dioxido-1,4-dihydro-3H-benzo[c][1,2,6]thiadiazin-3-yl)pyrrolidine-1-carbonitrile;
(R)-3-(7-(1-methyl-1H-pyrazol-4-yl)-2,2-dioxido-1,4-dihydro-3H-benzo[c][1,2,6]thiadiazin-3-yl)pyrrolidine-1-carbonitrile;
(R)-3-(2,2-dioxido-7-phenyl-1,4-dihydro-3H-benzo[c][1,2,6]thiadiazin-3-yl)pyrrolidine-1-carbonitrile;
(R)-3-(1-methyl-2,2-dioxido-7-phenyl-1,4-dihydro-3H-benzo[c][1,2,6]thiadiazin-3-yl)pyrrolidine-1-carbonitrile;
(R)-3-(1-methyl-2,2-dioxido-6-phenyl-1,4-dihydro-3H-benzo[c][1,2,6]thiadiazin-3-yl)pyrrolidine-1-carbonitrile;
(R)-3-(2,2-dioxido-6-phenyl-1,4-dihydro-3H-benzo[c][1,2,6]thiadiazin-3-yl)pyrrolidine-1-carbonitrile
N-(1-cyanopyrrolidin-3-yl)-N,N'-dimethyl-N'-phenylsulfuric diamide;
(R)-3-(8-morpholino-2,2-dioxido-1,4-dihydro-3H-benzo[c][1,2,6]thiadiazin-3-yl)pyrrolidine-1-carbonitrile;
(R)-3-(8-morpholino-2,2-dioxido-1,4-dihydro-3H-pyrido[3,4-c][1,2,6]thiadiazin-3-yl)pyrrolidine-1-carbonitrile;
a tautomer thereof, or a pharmaceutically acceptable salt of said compound or tautomer.

16. A method for treating Parkinson's Disease, comprising the step of administering an effective amount of a compound according to claim 1, a tautomer thereof, or a pharmaceutically acceptable salt of said compound or tautomer, to a patient in need thereof.

17. A method for treating multiple myeloma, comprising the step of administering an effective amount of a compound according to claim 1, a tautomer thereof, or a pharmaceutically acceptable salt of said compound or tautomer, to a patient in need thereof.

18. A pharmaceutical composition, comprising a compound of formula (I) as defined in claim 1, a tautomer thereof, or a pharmaceutically acceptable salt of said compound or tautomer, together with one or more pharmaceutically acceptable excipients.

* * * * *

UNITED STATES PATENT AND TRADEMARK OFFICE
CERTIFICATE OF CORRECTION

PATENT NO. : 11,091,488 B2
APPLICATION NO. : 15/776149
DATED : August 17, 2021
INVENTOR(S) : Kemp et al.

It is certified that error appears in the above-identified patent and that said Letters Patent is hereby corrected as shown below:

In the Claims

At Column 82, Line 17, "-NRaRb" should be printed as "-NR$^a$R$^b$."

At Column 82, Line 22, "-Q4-CORa" should be printed as "-Q$^4$-COR$^a$."

Signed and Sealed this
Third Day of May, 2022

Katherine Kelly Vidal
*Director of the United States Patent and Trademark Office*